(12) United States Patent
Takayama et al.

(10) Patent No.: US 6,489,155 B1
(45) Date of Patent: Dec. 3, 2002

(54) ENZYMES CAPABLE OF DEGRADING A SULFATED-FUCOSE-CONTAINING POLYSACCHARIDE AND THEIR ENCODING GENES

(75) Inventors: Masanori Takayama, Otsu (JP); Nobuto Koyama, Otsu (JP); Takeshi Sakai, Hirosaki (JP); Ikunoshin Kato, Otsu (JP)

(73) Assignee: Takara Shuzo Co., Ltd., Osaka (JP)

( * ) Notice: Subject to any disclaimer, the term of this patent is extended or adjusted under 35 U.S.C. 154(b) by 0 days.

(21) Appl. No.: 09/486,072

(22) PCT Filed: May 26, 1998

(86) PCT No.: PCT/JP98/02310

§ 371 (c)(1),
(2), (4) Date: Feb. 22, 2000

(87) PCT Pub. No.: WO99/11797

PCT Pub. Date: Mar. 11, 1999

(30) Foreign Application Priority Data

Sep. 3, 1997 (JP) ................................................ 9-252624

(51) Int. Cl.⁷ ............................ C12N 9/24; C07H 21/04
(52) U.S. Cl. .................... 435/200; 435/183; 435/252.3; 435/320.1; 435/325; 530/350; 536/23.1; 536/23.2
(58) Field of Search ................................. 435/200, 183, 435/252.3, 320.1, 325; 530/350; 536/23.1, 23.2

(56) References Cited

FOREIGN PATENT DOCUMENTS

| EP | 0 870771 A1 | 10/1996 |
| EP | 0 870 771 | 10/1998 |

OTHER PUBLICATIONS

Sasaki, et al., *Partial Purification and Characterization of an Enzyme Releasing 2–Sulfo–α–L–fucopyranose from 2–Sulfo–α–L–fucopyranosyl–(1–2) Pyridylaminated Fucose from a Sea Urchin, Strongylocentrotus nudus*, 1996, Biosci. Biotech. Biochem., 60:4, pp. 666–668.

Yu, et al., *Apoptosis of Human Carcinoma Cell Lines Induced by Fucoidan (Sulfated Fucose–Containing Polysaccharide) and its Degraded Fragments by Fucoidanase and Endo–Fucoidan Lyase*, 1996, Abstracts of 18th Symposium of Carbohydrates, Nihon Toshitsu Gakkai, pp. 93–94.

Ken Sakai et al.: Partial Purification and Characterization of an Enzyme Releasing 2–Sulfo–α–L–fucopyranose from 2–Sulfo–α–L–fucopyranosyl–(1–2) Pyridylaminated Fucose from a Sea Urchin, *Strongylocentrotus nudus* Biosci. Biotech. Biochem. (1996) vol. 60, No. 4, pp. 666–668.

Fu–gong, Y. et al., "Apoptosis of human carcinoma cell lines in duced by fucoidan (Sulfated fucoce–containing polysaccharide) and its degraded fragments by fucoidanase and endo–fucoidanlyase" Abstracts of 18$^{th}$ Symposium of Carbohydrates, Nihon Toshitsu Gakkai (1996) p. 93–94.

*Primary Examiner*—Rebecca E. Prouty
*Assistant Examiner*—Richard Hutson
(74) *Attorney, Agent, or Firm*—Kenyon & Kenyon

(57) ABSTRACT

An isolated gene having a DNA sequence coding for the polypeptide having a degrading activity of the sulfated-fucose-containing polysaccharide or having the functionally identical activity as above.

9 Claims, 5 Drawing Sheets

ENZYMES CAPABLE OF DEGRADING A SULFATED-FUCOSE-CONTAINING POLYSACCHARIDE AND THEIR ENCODING GENES

TECHNICAL FIELD OF THE INVENTION

The present invention relates to genes which codes for polypeptide having a degrading activity of the sulfated-fucose-containing polysaccharide useful for Structural analysis of sulfated-fucose-containing polysaccharide and also for preparation of degraded products of the said polysaccharide; to a method for manufacturing the said polypeptide by means of genetic engineering; and to a polypeptide obtained by the said method.

PRIOR ART

The sulfated-fucose-containing polysaccharide derived from marine algae is a mixture of sulfated polysaccharides which is called fucoidan as a whole mainly consisting of fucose and that which contains galactose, glucuronic acid, xylose, mannose, glucose, etc. as well has been known. Types and amounts of such constituting sugars vary depending upon the type of the marine algae used as a material. For examples, there is a report where commercially available fucoidan manufactured by Sigma is divided into molecular species of as much as 13 [Carbohydrate Research, 255, 213~224 (1994)]. They are roughly classified into two types where one is that where uronic acid is not substantially contained but most of the constituting sugar is fucose and another is that where uronic acid is contained but fucose and mannose are contained as constituting sugars.

With regard to the biological activities of sulfated-fucose-containing polysaccharide, various activities such as potentiation of macrophage activity, inhibition of metastasis of cancer and anti-coagulation of blood have been reported. However, since sulfated-fucose-containing polysaccharide has several molecular species, it is necessary to investigate after separating and purifying the sulfated-fucose-containing polysaccharide for checking which molecular species have the real activity. However, in the conventional methods, it is not possible to separate sufficiently and, therefore, it is difficult to prepare a large amount of the product to be used as a pharmaceutical. In addition, sulfated-fucose-containing polysaccharide is a sulfated polysaccharide having a high molecular weight and, when it is used as a pharmaceutical as it is, there are problems in view of antigenicity, homogeneity, anticoagulant activity, etc. whereby it is said to be necessary that the sulfated-fucose-containing polysaccharide is to be degraded to some extent.

A method where sulfated-fucose-containing polysaccharide is enzymatically decomposed to prepare a low molecular products is advantageous since the reaction can be carried out under mild conditions and uniformly degraded products are obtained due to a substrate specificity of the enzyme. It has been reported already that awabi (ear shell or abalone), scallop, sea urchin, marine microbes, etc. produce the enzyme which degrades the sulfated-fucose-containing polysaccharide. However, such an enzyme is usually contained in living organisms only in small quantities and, in addition, there are plural sulfated-fucose-containing polysaccharide degrading enzymes therein whereby it is necessary to conduct various purifying steps for preparing a single enzyme. Moreover, amino acid sequences and genetic structures of those enzymes have not been clarified at all.

PROBLEMS TO BE SOLVED BY THE INVENTION

An object of the present invention is to offer the gene which codes for polypeptide having a degrading activity of the sulfated-fucose-containing polysaccharide which is useful for preparation and structural analysis of sulfated-fucose-containing polysaccharide and also for preparation of degraded sulfated-fucose-containing polysaccharide. It is also to offer a polypeptide being able to be manufactured by a genetic engineering means using the said gene and having a degrading activity of the sulfated-fucose-containing polysaccharide.

MEANS TO SOLVE THE PROBLEMS

The present inventors have carried out an intensive investigation for the gene of microorganisms which produce the sulfated-fucose-containing polysaccharide degrading enzymes in order to clarify the amino acid sequence and base sequence of the polypeptide having a degrading activity of the sulfated-fucose-containing polysaccharide. As a result, they have clarified that there are each two types of gene coding for polypeptide, having a degrading activity of the sulfated-fucose-containing polysaccharide, derived from bacteria belonging to genus Alteromonas and Flavobacterium, respectively, elucidated their total base sequences, firstly clarified the amino acid sequence of the said polypeptide and succeeded in developing a method for an industrially advantageous manufacture of the polypeptide having a degrading activity of the sulfated-fucose-containing polysaccharide using the said gene whereupon they have accomplished the present invention.

Outline of the present invention will be that the first feature of the present invention relates to an isolated gene having a DNA sequence coding for the polypeptide having a degrading activity of the sulfated-fucose-containing polysaccharide or having the functionally identical activity as above.

The second feature of the present invention relates to a recombinant DNA containing the gene of the first feature of the present invention.

The third feature of the present invention relates to an expression vector where microorganisms, animal cells or plant cells in which the recombinant DNA of the second feature of the present invention is inserted as host cells.

The fourth feature of the present invention relates to a transformant which is transformed by the expression vector of the third feature of the present invention.

The fifth feature of the present invention relates to a method for the manufacture of polypeptide having a degrading activity of the sulfated-fucose-containing polysaccharide or that having the functionally identical activity as that, characterized in that, the transformant according to the fourth feature of the present invention is incubated and polypeptide having a degrading activity of the sulfated-fucose-containing polysaccharide or that having the functionally identical activity as that is collected from the incubated product.

The sixth feature of the present invention relates to a polypeptide having an amino acid sequence represented by any of the SEQ ID NO:1 to NO:4 of the Sequence Listing and having a degrading activity of the sulfated-fucose-containing polysaccharide or to a polypeptide having the functionally identical activity as that.

DETAINED DESCRIPTION

Figure 1:
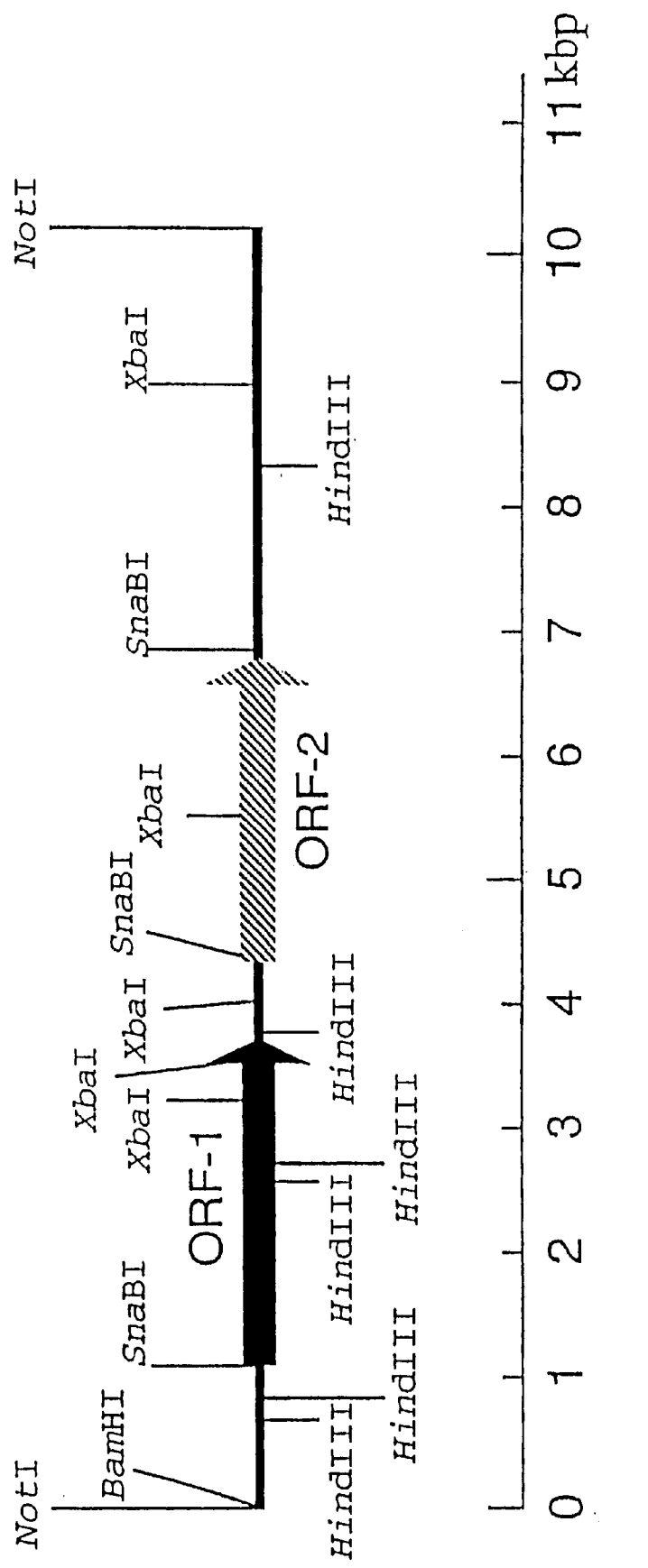
FIG. 1 shows the positions of ORF-1 and ORF-2.

The present invention will now be specifically illustrated as hereinafter.

The present invention relates to gene which codes for the polypeptide having a degrading activity of the sulfated-fucose-containing polysaccharide. An example of the polypeptide being coded by the said gene is a polypeptide, having an endo-sulfated-fucose-containing polysaccharide degrading activity, derived from the bacterium belonging to genus Alteromonas as mentioned in the following (1):

(1) acting on sulfated-fucose-containing polysaccharide having the following physicochemical properties (hereinafter, referred to as "sulfated-fucose-containing polysaccharide-F") and degrading said sulfated-fucose-containing polysaccharide:

(a) constituting saccharide: substantially being free from uronic acid; and (b) substantially incapable of being degraded by the fucoidanase produced by Flavobacterium sp. SA-0082 (FERM BP-5402).

As to the polypeptide having a degrading activity of the sulfated-fucose-containing polysaccharide, the endo-sulfated-fucose-containing polysaccharide degrading enzyme produced by Alteromonas sp. SN-1009 is available and the said enzyme can be prepared by a method mentioned in Referential Example 1-(3).

The above sulfated-fucose-containing polysaccharide-F can be prepared as mentioned in Referential Example 1.

The fucoidanase produced by Flavobacterium sp. SA-0082 (FERM BP-5402) can be prepared as mentioned in Referential Example 5.

With regard to other polypeptides, having a sulfated-fucose-containing polysaccharide degrading activity, a polypeptide having a degrading activity of the sulfated-fucose-containing polysaccharide as shown in the following (2) derived from the bacterium belonging to genus Flavobacterium is exemplified:

(2) acting on sulfated-fucose-containing polysaccharide having the following physicochemical properties (hereinafter, referred to as "sulfated-fucose-containing polysaccharide-U") and degrading the said sulfated-fucose-containing polysaccharide whereby at least one compound selected from the following formulae [I], [II], [III] and [IV] is liberated.

(c) constituting saccharide: containing uronic acid; and (d) being degraded by fucoidanase produced by Flavobacterium sp. SA-0082 (FERM BP-5402).

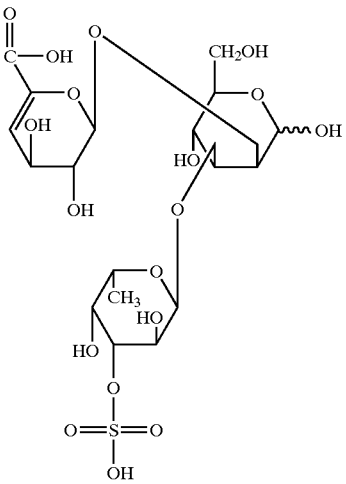

[I]

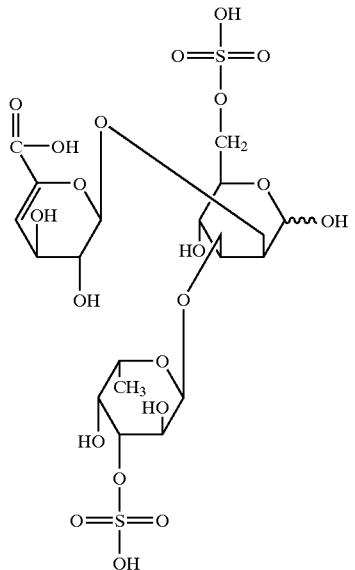

[II]

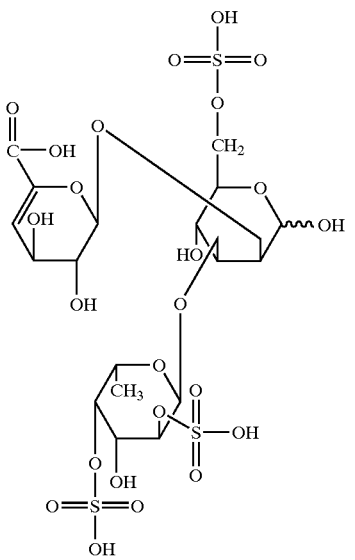

[III]

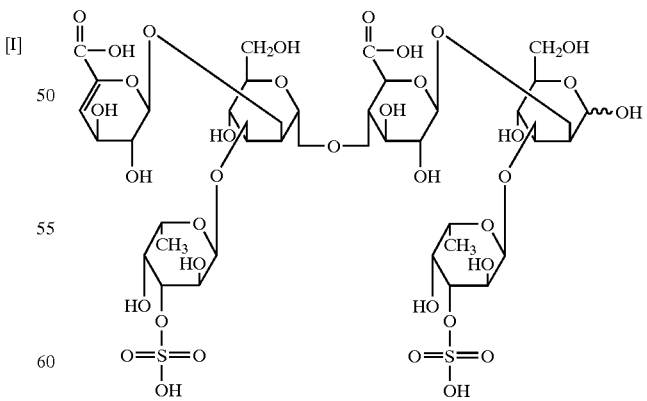

[IV]

An example of the polypeptide having a degrading activity of the sulfated-fucose-containing polysaccharide is a fucoidanase produced by Flavobacterium sp. SA-802 and the said fucoidanase can be prepared by a method described in Referential Example 5.

Hereinafter, a mixture of sulfated-fucose-containing polysaccharide-F and sulfated-fucose-containing polysaccharide-U will be referred to as a sulfated-fucose-containing polysaccharide mixture.

The polypeptide having a degrading activity of the sulfated-fucose-containing polysaccharide in the present invention means not only a sulfated-fucose-containing polysaccharide degrading enzyme of a natural type but also a polypeptide in which amino acid sequence is modified by deletion, substitution, insertion, addition, etc. of amino acids in the amino acid sequence of a natural type so far as the said polypeptide has a degrading activity of the sulfated-fucose-containing polysaccharide.

Incidentally, the sulfated-fucose-containing polysaccharide degrading enzyme of a natural type means, for example, that which is derived from bacterium belonging to genus Alteromonas and that belonging to genus Flavobacterium. However, the present invention is not limited thereto but covers those derived from other bacteria of course, from microbes such as yeast, mold, Ascomycetes, Basidiomycetes, etc. and from organisms such as plants and animals.

In the present invention, the polypeptide having a functionally identical activity means as follows.

In naturally occurring proteins, besides polymorphism and variation of gene coding for the said protein, variations such as deletion, addition, insertion, substitution, etc. of amino acid residues in the amino acid sequence as a result of modifying reaction of protein after production in vivo and during purification may take place but, in spite of that, it has been known that some of them have substantially same physiological and biological activities as the protein having no variation. Thus, a substance which has a structural difference but has no big difference in view of its function will be called a polypeptide having the functionally identical activity.

This is the same even when the above variation is artificially introduced into the amino acid sequence of the protein and, in that case, it is possible to prepare much more variants. However, such a variant will be interpreted as the polypeptide having the functionally identical activity so far as it shows substantially same physiological activity as that which has no variation.

For example, a methionine residue existing at the N-terminal of protein expressed in *Escherichia coli* is said to be removed by the action of methionine aminopeptidase in many cases but, depending upon the type of the protein, both products with and without methionine residue are produced. However, the fact that whether or not the methionine residue is present usually does not affect the activity of protein. It has been also known that a polypeptide in which a certain cysteine residue in the amino acid sequence of human interleukin 2 (IL-2) is substituted with serine maintains an interleukin 2 activity [*Science*, 224, 1431 (1984)].

Further, when production of protein is carried out by means of genetic engineering, it is often done to express as a fusion protein. For example, it has been carried out that N-terminal peptide derived from another protein is added to the N-terminal of the desired protein in order to increase the expressing amount of the desired protein or that a suitable peptide chain is added to and is expressed at the N-terminal or the C-terminal of the desired protein so as to make it easier to purify the desired protein by using a carrier having an affinity to the said added peptide chain.

Moreover, it is often noted that a polypeptide in which at least one of deletion, addition, insertion and substitution of one or more amino acid residue(s) is conducted for the amino acid sequence of the desired protein has the functionally identical activity with the desired protein. Such a polypeptide and gene which codes for the said polypeptide are also covered by the present invention regardless of a naturally-occurring and insolated one and an artificially prepared one.

It has been known that, usually, there is/are each 1~6 types of codon (a combination of three bases) which designates the amino acid on gene for each type of the amino acid. Accordingly, gene which codes for the amino acid sequence may be present abundantly although that depends upon the particular amino acid sequence. Gene is never present in a stable manner in nature but occurrence of variation in its nucleic acid is not rare. There are some cases where the variation taking place on gene does not affect the amino acid sequence which is coded thereby (this is called a silent variation) and, in that case, a different gene which codes for the same amino acid sequence is produced. Accordingly, even if the gene which codes for a specific amino acid sequence is isolated, there is still a possibility that, during the course of the passage of the living organism containing the same, many kinds of gene coding for the same amino acid sequence are generated.

Further, it is not difficult to artificially prepare many kinds of gene coding for the same amino acid sequence provided that various genetic engineering means are applied.

For example, there are some cases where the expressed amount of protein is low in the production of protein by a genetic engineering means when the codon used on the inherent gene coding for the desired protein is in a low frequency in the host which is used there. In that case, it has been carried out to attempt a high expression of the desired protein by artificially converting the codon into that which is frequently used in the said host without changing the coded amino acid sequence. It goes without saying that many kinds of gene coding for a specific amino acid sequence can be artificially prepared as such. Accordingly, even such an artificially prepared and different polynucleotide is also covered by the present invention so far as it codes for the amino acid sequence which is disclosed in the present invention.

In addition, there are many cases where, in the polypeptides having the functionally identical activity, genes coding for them have a homology. Therefore, the gene which is able to hybridize the gene used in the present invention under a strict condition and codes for a polypeptide having a degrading activity of the sulfated-fucose-containing polysaccharide is covered by the present invention as well.

As hereunder, the present invention will be specifically illustrated by taking Alteromonas sp. SN-1009 and Flavobacterium sp. SA-0082 as examples.

This Alteromonas sp. SN-1009 has been deposited at National Institute of Bioscience and Human-Technology, Agency of Industrial Science and Technology (1-3, Higashi 1-chome, Tsukuba, Ibaraki, 305-8566 JAPAN) since Feb. 13, 1996 (date of the original deposit) under the accession number FERM BP-5747 as the international deposition. On the other hand, Flavobacterium sp. SA-0082 has been deposited at National Institute of Bioscience and Human-Technology, Agency of Industrial Science and Technology since Mar. 29, 1995 (date of the original deposit) under the accession number FERM BP-5402 as the international deposition.

In order to obtain the gene coding for the polypeptide having a degrading activity of the sulfated-fucose-containing polysaccharide produced by Alteromonas sp. SN-1009 or Flavobacterium sp. SA-0082, it is possible to utilize, for example, a hybridization method, a PCR method or a combination thereof. In those methods, probe which is able to hybridize with the said gene or primer which is able to amplify the said gene or a part thereof by a PCR method is necessary but, since amino acid sequence and gene structure of the polypeptide having the sulfated-fucose-containing polysaccharide produced by those strains have not been known at all, it is not possible to prepare a synthetic oligonucleotide which is applicable as the probe or the primer. Therefore, at first, a partial amino acid sequence of the sulfated-fucose-containing polysaccharide degrading enzyme produced by the above microorganisms and preparation of the synthetic oligonucleotide applicable as the probe or the primer is investigated.

First, Alteromonas sp. SN-1009 or Flavobacterium sp. SA-0082 is cultivated and then each of the produced sulfated-fucose-containing polysaccharide degrading enzyme is isolated and purified from the medium.

Then information concerning the partial amino acid sequence is obtained for each of the purified sulfated-fucose-containing polysaccharide degrading enzyme. In order to determine the partial amino acid sequence, the sulfated-fucose-containing polysaccharide degrading enzyme is, for example, subjected to an amino acid sequence analysis by an Edman degradation according to a conventional method (Protein Sequencer 476A manufactured by Applied Biosystems may be used for example) whereupon the N-terminal amino acid sequence of the sulfated-fucose-containing polysaccharide degrading enzyme can be determined. Alternatively, purified sulfated-fucose-containing polysaccharide degrading enzyme is subjected to a limited hydrolysis by treating with a proteolytic enzyme having a high substrate specificity such as Achromobacter protease I, N-tosyl-L-phenylalanyl chloromethyl ketone (TPCK) treated-trypsin, etc., the resulting peptide fragments are separated and purified by means of a reversed HPLC and the purified peptide fragments are subjected to an amino acid sequence analysis whereupon many information on amino acid sequence is obtained.

Information concerning the partial amino acid sequence specific to the sulfated-fucose-containing polysaccharide degrading enzyme obtained as such is selected and, based upon the said information, degenerated oligonucleotide where the base sequence is designed and synthesized. At that time, it is necessary to synthesize a long oligonucleotide having a low degree of degeneration or, in other words, an oligonucleotide having a high specificity to the gene coding for the polypeptide having a degrading activity of the sulfated-fucose-containing polysaccharide. Design of the oligonucleotide is an important factor for cloning of the gene coding for the polypeptide having a degrading activity of the sulfated-fucose-containing polysaccharide.

Next, it is necessary to investigate the condition for a specific hybridization of a synthetic oligonucleotide with the gene coding for the polypeptide having a degrading activity of the sulfated-fucose-containing polysaccharide by means of a Southern hybridization.

For example, genome DNA of Alteromonas sp. SN-1009 or Flavobacterium sp. SA-0082 is completely digested by an appropriate restriction enzyme, separated by means of an agarose gel electrophoresis and subjected to a blotting on Nylon membrane or the like by a conventional method. In conducting the hybridization, the Nylon membrane is at first blocked by keeping at 65° C. for several hours in a hybridizing solution containing 6×SSC (1×SSC means a product prepared by dissolving 8.77 g of sodium chloride and 4.41 g of sodium citrate in one liter of water), 1% of sodium dodecyl sulfate (SDS), 100 µg/ml of salmon sperm DNA and 5×Denhardt's solution (containing each 0.1% of bovine serum albumin, polyvinylpyrrolidone and Ficoll), then a synthetic oligonucleotide labeled with $^{32}$P or the like is added thereto and the mixture is kept at 42° C. overnight. This Nylon membrane is washed with 1×SSC containing 0.1% of SDS at 42° C. for 30 minutes and subjected to an autoradiography to detect DNA fragments which hybridize with the synthetic oligonucleotide probe. It is effective to select the optimum condition by investigating the warming temperature, salt concentration of the washing solution, etc. taking the length of the synthetic oligonucleotide used and the complementarity with the gene coding for the polypeptide having a degrading activity of the sulfated-fucose-containing polysaccharide into consideration.

For obtaining the DNA fragments detected as such containing the gene coding for the polypeptide having a degrading activity of the sulfated-fucose-containing polysaccharide, a method where the DNA fragments corresponding to the position of the directly detected bands are extracted from the gel and purified, a library where the fragments are integrated into a commonly used vector of a host-vector type and a colony hybridization or a plaque hybridization is carried out under the same condition as in the case of a Southern hybridization to screen and isolate the clone containing the desired DNA fragments may be used. Alternatively, genome DNA of Alteromonas sp. SN-1009 or Flavobacterium sp. SA-0082 is directly digested with an appropriate restriction enzyme, a library where they are integrated into vector of the commonly used host-vector type is prepared and a hybridization is carried out by the same manner whereupon clone containing the desired DNA fragments is screened and isolated.

With regard to the host-vector system used therefor, known one may be used and its examples are plasmid vector such as pUC18 and pUC19 using *Escherichia coli* as a host or a phage vector such as a lambda phage although the present invention is not limited thereto.

With regard to the type and the handling of those host-vector systems, the commonly used type and method mentioned, for example, in "Molecular Cloning, A Laboratory Manual", Second Edition, by J. Sambrook, et al., published by Cold Spring Harbor Laboratory, 1989) may be used.

When the vector containing the desired DNA fragment can be selected, the base sequence of the desired DNA fragment inserted into the vector can be determined by a common method such as a dideoxy method [*Proceedings of the National Academy of Science, U.S.A.*, 74, 5463 (1977)]. When the determined base sequence is compared with the N-terminal analysis, partial amino acid sequence, molecular weight, etc. of the sulfated-fucose-containing polysaccharide degrading enzyme, it is now possible to be aware of the structure of the gene in the resulting DNA fragment and also the amino acid sequence of the polypeptide for which the said gene codes.

In addition, a PCR method may be used as a method for preparing the gene coding for the polypeptide having a degrading activity of the sulfated-fucose-containing polysaccharide using the oligonucleotide obtained based upon the partial amino acid sequence of the above-mentioned sulfated-fucose-containing polysaccharide degrading enzyme. Among that, a PCR method using a cassette DNA is a method whereby fragments of the desired gene applicable for a hybridization method can be obtained within a short time from a little information for the amino acid sequence.

For example, the genome DNA extracted by a conventional method from the cultivated cells of Flavobacterium sp. SA-0082 is digested by an appropriated restriction enzyme and a synthetic DNA (cassette DNA) having a known sequence is ligated thereto. The resulting mixture is used as a template and a PCR is carried out using the said gene-specific oligonucleotide primer which is designed based upon the information on the above partial amino acid sequence and an oligonucleotide primer (cassette primer) complementary to the cassette DNA whereupon the desired DNA fragments can be amplified. With regard to the cassette DNA and the cassette primer, those manufactured, for example, by Takara Shuzo may be utilized. It is preferred that the cassette DNA contains the sequence corresponding to two types of cassette primer and it is effective that, at first, the first PCR is carried out using a primer which is far from the ligated restriction enzyme site and then the second PCR is carried out using a part of the above reaction solution as a template and using the primer of the inner side. Further, with regard to the said gene-specific oligonucleotide primer, specificity of the said gene becomes high and possibility of the specific amplification of the desired DNA fragments becomes high when the two types are designed and synthesized in parallel, the upstream primer is used in the first PCR and the downstream primer is used in the second PCR.

However, since the base sequence of the desired gene is ambiguous, it is not always true that the restriction enzyme site used for the ligation of the cassette DNA is not always located at a position appropriate for the amplifying reaction by the PCR from the region coding for the partial amino acid sequence. Therefore, it is necessary to use many kinds of cassette DNAs of restriction enzymes. In addition, although the PCR may be carried out under the commonly-used condition such as that mentioned, for example, in "PCR Technology" edited by H. A. Erlich, published by Stockton Press, 1989), it is necessary to select the optimum condition for making the nonspecific amplified bands minimum by taking annealing temperature, cycle numbers, magnesium concentration, heat-resistant polymerase concentration, etc. into consideration depending upon the length of the synthetic oligonucleotide used and the complementarity with the gene coding for the polypeptide having a degrading activity of the sulfated-fucose-containing polysaccharide.

The PCR solution is subjected to an electrophoresis such as by an agarose gel to confirm the amplified DNA fragments. Those fragments are extracted and purified by a common method and inserted into a commonly used cloning vector such as pUC18 or pUC19 and the base sequence thereof can be analyzed by, for example, means of a dideoxy method. Alternatively, the recovered amplified DNA fragments may be subjected to a direct base sequence analysis using a cassette primer used for the PCR. When something coding for the already-determined partial amino acid sequence of the sulfated-fucose-containing polysaccharide degrading enzyme are obtained in addition to the sequence of the primer as a result, the conclusion is that the gene coding for the said enzyme or the fragments of the gene showing a homology thereto can be obtained.

When the DNA fragments prepared by a Southern hybridization or by a PCR is a part of the gene coding for the desired enzyme, a screening of a genome library is carried out by a hybridization using the said DNA fragments as a probe or a PCR is carried out using an oligonucleotide prepared based upon the base sequence of the said DNA fragments as a primer whereupon the DNA fragments containing the full length of the gene coding for the desired enzyme can be obtained.

Further, when the genome DNA of Alteromonas sp. SN-1009 or Flavobacterium sp. SA-0082 is analyzed by means of a Southern hybridization using the gene of the sulfated-fucose-containing polysaccharide degrading enzyme obtained as above or a part thereof, it is possible to obtain the information for the size of the genome DNA restriction enzyme fragments of Alteromonas sp. SN-1009 or Flavobacterium sp. SA-0082 containing the gene coding for the polypeptide having a degrading activity of the sulfated-fucose-containing polysaccharide from the position of the detected band. Moreover, the numbers of the gene coding for the polypeptide having a degrading activity of the sulfated-fucose-containing polysaccharide and also of the numbers of the gene complementary thereto can be presumed and the DNA fragments containing such genes can be isolated by the same method as mentioned already.

The fact that whether the DNA fragments prepared as such contain the gene coding for the desired enzyme can be confirmed by preparing an expression vector containing the said DNA fragment isolated in the final stage, conducting a transformation of the host using the said vector, incubating the said transformant and measuring the degrading activity of the expressed polypeptide for the sulfated-fucose-containing polysaccharide.

In the present invention, the gene having the amino acid sequence represented by SEQ ID NO:1 and NO:2 of the Sequence Listing and having the base sequence coding for the polypeptide having a degrading activity of the sulfated-fucose-containing polysaccharide was obtained from Alteromonas sp. SN-1009. Examples of the base sequence coding for the polypeptide having the amino acid sequence represented by SEQ ID NO:1 and NO:2 are shown in SEQ ID NO:5 and NO:6 of the Sequence Listing, respectively.

Further, the gene having the base sequence coding for the polypeptide having amino acid sequence represented by SEQ ID NO:3 and NO:4 of the Sequence Listing and having a degrading activity of the sulfated-fucose-containing polysaccharide was isolated from Flavobacterium sp. SA-0082. Examples of the base sequence coding for the polypeptide having the amino acid sequences SEQ NO:3 and NO:4 are shown in SEQ NO:7 and NO:8 of the Sequence Listing, respectively.

With regard to a method for preparing the gene coding for the polypeptide having a degrading activity of the sulfated-fucose-containing polysaccharide or having the functionally identical activity using the base sequence of the gene of the present invention, the following method may be applied for example.

Thus, at first, chromosome DNA obtained from the desired gene source or cDNA obtained from mRNA by reverse transcriptase is introduced into a host by ligation to plasmid or phage vector by a common method to prepare a library. The library is incubated on a plate and the grown colonies or plaques are transferred to a membrane of nitrocellulose or Nylon and denatured to fix the DNA to the membrane. This membrane is warmed in a solution containing a probe labeled, for example, with $^{32}P$ (with regard to the probe used here, any amino acid sequence represented by SEQ ID NO:1 to NO:4 of the Sequence Listing or the base sequence coding for a part thereof may be used and, for example, a base sequence represented by any of SEQ NO:5 to NO:8 of the Sequence Listing or a part thereof may be used) whereupon the a hybrid is formed between the probe and the DNA on the membrane. For example, the membrane where DNA is fixed is subjected to a hybridization with a probe at 65° C. for 20 hours in a solution containing 6×SSC, 1% SDS, 100 µg/ml salmon sperm DNA and 5×Denhardt's solution. After the hybridization, the probe which is non-specifically adsorbed is washed out, clone which formed the probe is identified by, for example, means of autoradiography. This operation is repeated until the hybrid-formed clone becomes a single one. Into the clone prepared as such, the gene coding for the desired polypeptide is inserted.

Base sequence of the resulting gene is determined by, for example, the following means and it is confirmed that whether the resulting gene is a gene which codes for the polypeptide having the desired degrading activity of the sulfated-fucose-containing polysaccharide or having the functionally identical activity.

When the transformant is *Escherichia coli* which is transformed by plasmid, determination of the base sequence is carried out by incubating it in a test tube or the like and extracting the plasmid by a common method. This is incised by a restriction enzyme, the inserted fragment is taken out and subcloned to an M13 phase vector or the like and a base sequence is determined by a dideoxy method. When a phase vector is used for the recombinant, the base sequence can be also determined by the fundamentally same steps. With regard to the basic experimental methods from the incubation to the base sequence determination as such, there is a description, for example, in "Molecular Cloning, A Laboratory Manual", second edition, by J. Sambrook, et al., Cold Spring Harbor Laboratory, 1989.

In order to confirm whether the resulting gene is a gene coding for the polypeptide having a degrading activity of the sulfated-fucose-containing polysaccharide or having the functionally identical activity, the determined base sequence or the amino acid sequence being coded thereby is compared with the base sequence represented by any of SEQ ID NO:5 to NO:8 or is compared with the amino acid sequence represented by any of SEQ ID NO:1 to NO:4 of the Sequence Listing of the present invention.

When the resulting gene does not contain all of the region coding for the polypeptide having a degrading activity of the sulfated-fucose-containing polysaccharide or having a functionally identical activity, a synthetic DNA library is prepared based upon the resulting gene, then the lacking region is amplified by a PCR or the fragments of the resulting gene are used as a probe to further screen the DNA library or cDNA library whereby the base sequence of total coding region of the polypeptide having a degrading activity of the sulfated-fucose-containing polysaccharide or having the functionally identical activity can be determined.

It is also possible to design the primer for the PCR from the base sequence of the gene of the present invention. When a PCR is carried out using the said primer, it is possible to detect the gene fragment having a high homology with the gene of the present invention and also to obtain the whole gene.

Then the resulting gene is expressed and a degrading activity of the sulfated-fucose-containing polysaccharide is measured whereby the function of the resulting gene is ascertained.

The following method is convenient for the production of a polypeptide having a degrading activity of the sulfated-fucose-containing polysaccharide using the gene coding for the polypeptide having a degrading activity of the sulfated-fucose-containing polysaccharide of the present invention.

First, a transformation of the host is carried out using a vector containing the gene coding for the polypeptide having a desired degrading activity of the sulfated-fucose-containing polysaccharide and then the transformant is incubated under the commonly applied conditions whereby a polypeptide having a degrading activity of the sulfated-fucose-containing polysaccharide can be produced. At that time, the said polypeptide is produced in a form of an inclusion body in some cases. As to the host, incubated cells of microorganisms, animal cells, plant cells, etc. may be used.

Confirmation of the expression is convenient by, for example, measuring the degrading activity of the sulfated-fucose-containing polysaccharide. Measurement of the activity may be carried out using, for example, an extract of recombinant *Escherichia coli* cells as an enzyme solution.

When expression of the polypeptide having the desired degrading activity of the sulfated-fucose-containing polysaccharide is noted, the optimum condition for composition of the medium, pH of the medium, incubating temperature, amount and stage of the inducer used, incubating time, etc. is determined when the transformant is *Escherichia coli* for example whereby it is possible to efficiently produce a polypeptide having a degrading activity of the sulfated-fucose-containing polysaccharide.

A common method is used for purifying the polypeptide having a degrading activity of the sulfated-fucose-containing polysaccharide from the incubated transformant. When a polypeptide having a degrading activity of the sulfated-fucose-containing polysaccharide is accumulated within the cells as in the case where the transformant is *Escherichia coli,* the transformant is collected by means of centrifugation after completion of the incubation, disintegrated by an ultrasonic wave treatment for example and centrifuged to collect the cell-free extract. When this is subjected to a common purifying means for protein such as salting out or ion-exchange, gel filtration, hydrophobic or affinity chromatography, the desired polypeptide can be purified. In some of host-vector systems used therefor, the expressed product may be secreted out of the transformant and, in that case, the supernatant liquid may be similarly purified.

When the polypeptide having a degrading activity of the sulfated-fucose-containing polysaccharide produced by the transformant is produced within the cells, various enzymes in the cells are present together but, since their amount is only too little as compared with the amount of the polypeptide having a degrading activity of the sulfated-fucose-containing polysaccharide, the purification is quite easy. In addition, if the cells used as the host are selected, amount of the enzyme derived from the host acting on the sulfated-fucose-containing polysaccharide is greatly reduced. Further, when the polypeptide having a degrading activity of the sulfated-fucose-containing polysaccharide is secreted outside of the cells, the components of the medium are present together but they can be easily separated from the polypeptide having a degrading activity of the sulfated-fucose-containing polysaccharide.

Furthermore, when the host is *Escherichia coli* for example, the expressed product may be in some cases produced as an insoluble inclusion body. In that case, the cells are collected by centrifugation or the like after completion of incubation, disintegrated by an ultrasonic wave treatment or the like and centrifuged whereupon the insoluble fractions containing the inclusion body are collected. After washing the inclusion body, it is made soluble using a commonly used solubilizer for protein such as urea or guanidine hydrochloride, purified by various chromatographic means such as ion-exchange, gel filtration, hydrophobic or affinity if necessary, and subjected to a refolding operation using, for example, dialysis or dilution whereupon a polypeptide keeping the activity and having a desired degrading activity of the sulfated-fucose-containing polysaccharide can be prepared. When the resulting sample is further purified by various chromatographic means upon necessity, it is possible to give a polypeptide having a degrading activity of the sulfated-fucose-containing polysaccharide in high purity.

Incidentally, in the case of production of a polypeptide having a functionally identical activity as the polypeptide having a degrading activity of the sulfated-fucose-containing polysaccharide, the same production method and purification method may be used.

As such, the present invention offers the primary structure and gene structure of a polypeptide having a degrading activity of the sulfated-fucose-containing polysaccharide. It is also possible to manufacture a polypeptide having a degrading activity of the sulfated-fucose-containing polysaccharide or a polypeptide having the functionally identical activity by a genetic engineering means.

When the genetic engineering manufacturing method of the present invention is used, it is now possible to prepare a polypeptide having a degrading activity of the sulfated-fucose-containing polysaccharide and also a polypeptide having a functionally identical activity of a high purity in a low cost.

Thus, in a method for the manufacture of enzymes having a degrading activity of the sulfated-fucose-containing polysaccharide by means of incubation of microorganisms belong to genus Alteromonas or Flavobacterium producing the sulfated-fucose-containing polysaccharide degrading enzyme, protease and other polysaccharide degrading enzymes are simultaneously produced and, therefore, for the isolation of the desired sulfated-fucose-containing polysaccharide degrading enzyme, separation from those enzymes and purification which are very troublesome are required and it is also necessary for inducing the production of the enzyme to add an expensive sulfated-fucose-containing polysaccharide during the incubation whereby the sulfated-fucose-containing polysaccharide degrading enzyme is induced. However, in accordance with the present invention, it is now possible to offer a highly purified polypeptide having a degrading activity of the sulfated-fucose-containing polysaccharide in a low cost.

EXAMPLES

The present invention will be further illustrated by way of the following examples although the present invention is never limited to the following examples.

Referential Example 1

(1) 2 kg of dried *Kjellmaniella crassifolia* was ground with a free mill Model M-2 (manufactured by Nara Kikai Seisakusho). The dry powder thus obtained was treated in 4.5 times as much 80% ethanol at 80° C. for 2 hours and then filtered. The obtained residue was repeatedly washed with 80% ethanol and filtered thrice in the same manner as described above to thereby give 1,870 g of the residue after ethanol-washing. To this residue was added 36 l of water and the mixture was treated at 100° C. for 2 hours to thereby give the extract. The salt concentration of the extract was adjusted to the same level as that of a 400 mM solution of sodium chloride. Then 5% cetylpyridinium chloride was added thereto until no precipitate was formed any more. After centrifuging, the precipitate was repeatedly washed with 80% ethanol to thereby completely eliminate the cetylpyridinium chloride therefrom. Next, it was dissolved in 3 l of 2 M sodium chloride. After removing the insoluble matters by centrifugation, 100 ml of DEAE-Cellulofine A-800 equilibrated with 2 M sodium chloride was suspended therein. The suspension was stirred and then filtered to thereby remove the resin. The filtrate was fed into a 100 ml DEAE-Cellulofine A-800 column equilibrated with 2 M sodium chloride and the fraction passing therethrough was desalted and low-molecular weight matters were removed therefrom by using an ultrafilter (exclusion molecular weight of membrane: 100,000). The precipitate thus formed was eliminated by centrifugation. The supernatant was freeze-dried to thereby give 82.2 g of a purified *Kjellmaniella crassifolia* sulfated-fucose-containing polysaccharide mixture.

(2) 7 g of the above-mentioned sulfated-fucose-containing polysaccharide mixture originating in *Kjellmaniella crassifolia* was dissolved in 700 ml of 20 mM of sodium acetate (pH 6.0) containing 0.2 M of calcium chloride. Then the solution was fed into a 4000 ml DEAE-Sepharose FF column preliminarily equilibrated with 20 mM of sodium acetate (pH 6.0) containing 0.2 M of calcium chloride. Then the column was thoroughly washed with 20 mM of sodium acetate (pH 6.0) containing 0.2 M of calcium chloride and developed by linear gradient elution with sodium chloride of 0 to 4 M. Then the fractions eluted at sodium chloride concentrations of 0.9~1.5 M were collected and desalted by using an ultrafilter provided with an ultrafiltration membrane of exclusion molecular weight of 100,000. After freeze-drying, 4.7 g of a freeze-dried preparation of the sulfated-fucose-containing polysaccharide-F was obtained.

The fractions eluted at sodium chloride concentrations of 0.05~0.8 M were also collected and desalted by using an ultrafilter provided with an ultrafiltration membrane of exclusion molecular weight of 100,000. After freeze-drying, 2.1 g of a freeze-dried preparation of the sulfated-fucose-containing polysaccharide-U was obtained.

(3) Alteromonas sp. SN-1009 (FERM BP-5747) was inoculated into 600 ml of a medium comprising an artificial seawater (pH 8.2, manufactured by Jamarin Laboratory) containing 0.25% of glucose, 1.0% of peptone and 0.05% of yeast extract which had been sterilized (120° C., 20 minutes) and pipetted into a 2 l Erlenmeyer flask. Then the strain was incubated therein at 25° C. for 25 hours to thereby give a seed culture. Into a 30 l jar fermenter was fed 18 l of a medium comprising an artificial seawater (pH 8.0) containing 200 g of peptone, 4 g of yeast extract and 4 ml of a defoaming agent (KM70 manufactured by Shin-Etsu Chemical Co., Ltd.) and sterilized at 120° C. for 20 minutes. After cooling, 20 g of the *Kjellmaniella carssifolia* sulfated-fucose-containing polysaccharide-F prepared by the method of Referential Example 1-(1), which had been separately dissolved in 2 l of artificial seawater sterilized at 120° C. for 15 minutes, was added to the medium and 600 ml of the above-mentioned seed culture followed by incubation at 24° C. for 20 hours under aerating at a rate of 10 l/minute and agitating at 250 rpm. After the completion of the incubation, the culture medium was centrifuged to thereby give the cells and the culture supernatant.

When measured by using the sulfated-fucose-containing polysaccharide-F as the substrate with the method described in Referential Example 2, the culture supernatant showed an activity of the endo-sulfated-fucose-containing polysaccharide degrading enzyme of 10 mU/ml of the medium.

The resulting culture supernatant was concentrated with an ultrafilter of a fractional molecular weight of 10,000 and the precipitate thus formed was eliminated by centrifugation. Then it was salted out with the use of 85% ammonium sulfate. The precipitate thus formed was taken up by centrifugation and thoroughly dialyzed against a 20 mM Tris hydrochloride buffer (pH 8.2) containing artificial seawater (Jamarin S) diluted 10-fold. Thus 400 ml of a crude enzyme was obtained.

The resulting crude enzyme solution was adsorbed by a DEAE-Cellulofine A-800 (manufactured by Seikagaku Kogyo) column which had been equilibrated with a 20 mM Tris hydrochloride buffer (pH 8.2) containing 5 mM of sodium azide and artificial seawater (Jamarin S) diluted 10-fold. Then the adsorbed matters were thoroughly washed with the same buffer and eluted into the same buffer with the use of solutions containing 100 mM, 200 mM, 300 mM, 400 mM and 600 mM of sodium chloride. The active fractions were combined.

When measured by the method described in Referential Example 2, the resulting active fraction showed an enzyme activity of 20,400 mU (20.4 U).

The resulting active fractions were concentrated by an ultrafilter having a fractionating molecular weight of 10,000 and subjected to a ultrafiltration by adding 20 mM of Tris hydrochloride buffer (pH 8.2) containing 10 mM of calcium chloride and 50 mM of sodium chloride thereto whereupon the buffer was completely substituted.

The resulting enzyme solution was adsorbed with a column of DEAE-Sepharose FF which was previously equilibrated with the same buffer, the adsorbed thing was well washed with the same buffer, then further washed with the same buffer where the sodium chloride concentration was 150 mM and subjected to a gradient elution with sodium chloride using the same buffer containing from 150 mM to 400 mM of sodium chloride.

The resulting active fractions were collected, concentrated by means of an ultrafiltration and subjected to a gel filtration using Sephacryl S-200. A 10 mM Tris hydrochloride buffer (pH 8.0) containing 5 mM of sodium azide and 1/10 concentration of Jamarin S was used as an eluent. Incidentally, the molecular weight was determined by the said chromatography and found to be about 100,000.

The resulting active fractions were collected, well dialyzed against 20 mM of Tris hydrochloride buffer (pH 8.2) containing 10 mM of calcium chloride, 10 mM of potassium chloride and 4.2 M of sodium chloride, placed on a column of phenyl Sepharose CL-4B which was previously equilibrated with the same buffer where the sodium chloride concentration was 4M and eluted with the same buffer containing 4M, 3M, 2M, 1M, 0.5M or 0.15M of sodium chloride.

The resulting active fractions were collected, concentrated by means of an ultrafiltration and then subjected to an ultrafiltration by adding 20 mM of Tris hydrochloride buffer (pH 8.2) containing 10 mM of calcium chloride, 10 mM of potassium chloride and 150 mM of sodium chloride to completely substitute the buffer. The enzyme solution was placed on DEAE-Cellulofine A-800 which was previously equilibrated with the same buffer, washed with the same buffer and subjected to a gradient elution with sodium chloride of from 150 mM to 350 mM.

The resulting active fractions were collected, well dialyzed against the same buffer containing 50 mM of sodium chloride, adsorbed with DEAE-Cellulofine A-800 which was previously equilibrated with the same buffer containing 50 mM of sodium chloride, washed with the same buffer and subjected to a gradient elution with sodium chloride of from 50 mM to 150 mM. The resulting active fractions were assembled to give a purified enzyme.

When a molecular weight of the said purified enzyme was determined by means of an SDS(sodium dodecyl sulfate)-polyacrylamide electrophoresis and found to be about 90,000.

Referential Example 2

By using the sulfated-fucose-containing polysaccharide-F obtained by the steps in Referential Example 1-(2), the degrading activity of the endo-sulfated-fucose-containing polysaccharide is determined in the following manner.

Namely, 12 $\mu$l of a 2.5% solution of the sulfated-fucose-containing polysaccharide-F, 6 $\mu$l of a 1 M solution of calcium chloride, 9 $\mu$l of a 4 M solution of sodium chloride, 60 $\mu$l of a buffer (pH 7.5) containing 50 mM of acetic acid, imidazole and Tris hydrochloride buffer, 21 $\mu$l of water and 12 $\mu$l of a liquid to be subjected to determine a degrading activity are mixed together and reacted at 30° C. for 3 hours. Then the reaction mixture is treated at 100° C. for 10 minutes and centrifuged. Then the degree of degradation is measured by analyzing a 100 $\mu$l portion of the reaction mixture by HPLC.

As controls, a reaction mixture prepared by the same method except that the liquid to be subjected to determine a degrading activity is substituted with the buffer used in the subjected liquid and another reaction mixture prepared by the same method except that the sulfated-fucose-containing polysaccharide-F solution is substituted with water alone are prepared. These controls are also analyzed by HPLC.

The amount of the enzyme by which the fucosyl bonds in 1 $\mu$mol of the sulfated-fucose-containing polysaccharide-F can be cleaved in one minute is taken as one U. The fucosyl bonds thus cleaved are calculated in accordance with the following equation:

$$\text{Activity (U/ml)} = \{(12 \times 2.5)/(100 \times MF)\} \times \{(MF/M) - 1\} \times \{1/(180 \times 0.01)\} \times 1000$$

| | |
|---|---|
| (12 × 2.5)/100 | Sulfated-fucose-containing polysaccharide-F (mg) added to reaction system; |
| MF | Average molecular weight of substrate (sulfated-fucose-containing polysaccharide-F); |
| M | Average molecular weight of reaction product; |
| (MF/M) − 1 | Number of cleavages by enzyme in one molecule of sulfated-fucose-containing polysaccharide-F; |
| 180 | Reaction time (minute); and |
| 0.01 | Volume (ml) of enzyme solution. |

The HPLC is effected under the following conditions:

| | |
|---|---|
| Apparatus | Model L-6200 (manufactured by Hitachi, Ltd.); |
| column | OHpak SB-806 (8 mm × 300 mm, manufactured by Showa Denko K.K.); |
| Eluent | 25 mM imidazole buffer (pH 8) containing 5 mM of sodium azide, 25 mM of calcium chloride and 50 mM of sodium chloride; |
| Detection | Differential refractometric detector (Shodex RI-71, manufactured by Showa Denko K.K.); |
| Flow rate | 1 ml/minute; |
| Column temperature | 25° C. |

To measure the average molecular weight of the reaction product, marketed pullulan with a known molecular weight (STANDARD P-82, manufactured by Showa Denko K.K.)

is analyzed by HPLC under the same conditions as those described above. Then a curve showing the relationship between the molecular weight of the pullulan and the retention time on the OHpak SB-806 is prepared and employed as the standard curve for determining the molecular weight of the above-mentioned enzymatic reaction product.

Referential Example 3

By using the sulfated-fucose-containing polysaccharide-U obtained by the steps in Referential Example 1-(2), the degrading activity of the sulfated-fucose-containing polysaccharide is determined in the following manner.

50 μl of a 2.5% solution of sulfated-fucose-containing polysaccharide-U, 10 μl of the liquid to be subjected to determine a degrading activity and 60 μl of a 83 mM phosphate buffer (pH 7.5) containing 667 mM of sodium chloride are mixed together and reacted at 37° C. for 3 hours. Then 105 μl of the reaction mixture is mixed with 2 ml of water under stirring and the absorbance (AT) is measured at 230 nm. As controls, a reaction mixture prepared by the same method except that the liquid to be subjected to determine a degrading activity is substituted with the above-mentioned buffer used in the subjected liquid alone and another reaction mixture prepared by the same method except that a solution of sulfated-fucose-containing polysaccharide-U is substituted with water alone are prepared and the absorbances (AB1 and AB2) thereof are also measured.

The amount of the enzyme by which 1 μmol of the glycoside bonds between mannose and uronic acid can be exclusively cleaved in one minute is taken as one U. The bonds thus cleaved are determined by taking the millimolar molecular extinction coefficient of the unsaturated uronic acid formed in the elimination reaction as 5.5. The activity of the enzyme is determined in accordance with the following equation:

Activity (U/ml)=(AT−AB1−AB2)×2.105×120/5.5×105×0.01×180;

| | |
|---|---|
| 2.105 | Volume (ml) of the sample the absorbance of which is to be measured; |
| 120 | Volume (μl) of the enzyme reaction mixture; |
| 5.5 | Millimolar molecular extinction coefficient (/mM) of unsaturated uronic acid at 230 nm; |
| 105 | Volume (μl) of the reaction mixture employed for dilution; |
| 0.01 | Volume (ml) of the enzyme; and |
| 180 | Reaction time (minute). |

Referential Example 4

(1) The molecular weights of the sulfated-fucose-containing polysaccharide-F and sulfated-fucose-containing polysaccharide-U are determined by the gel filtration method with the use of Sephacryl S-500. As a result, each shows a molecular weight distribution around about 190,000.

Figure 2:
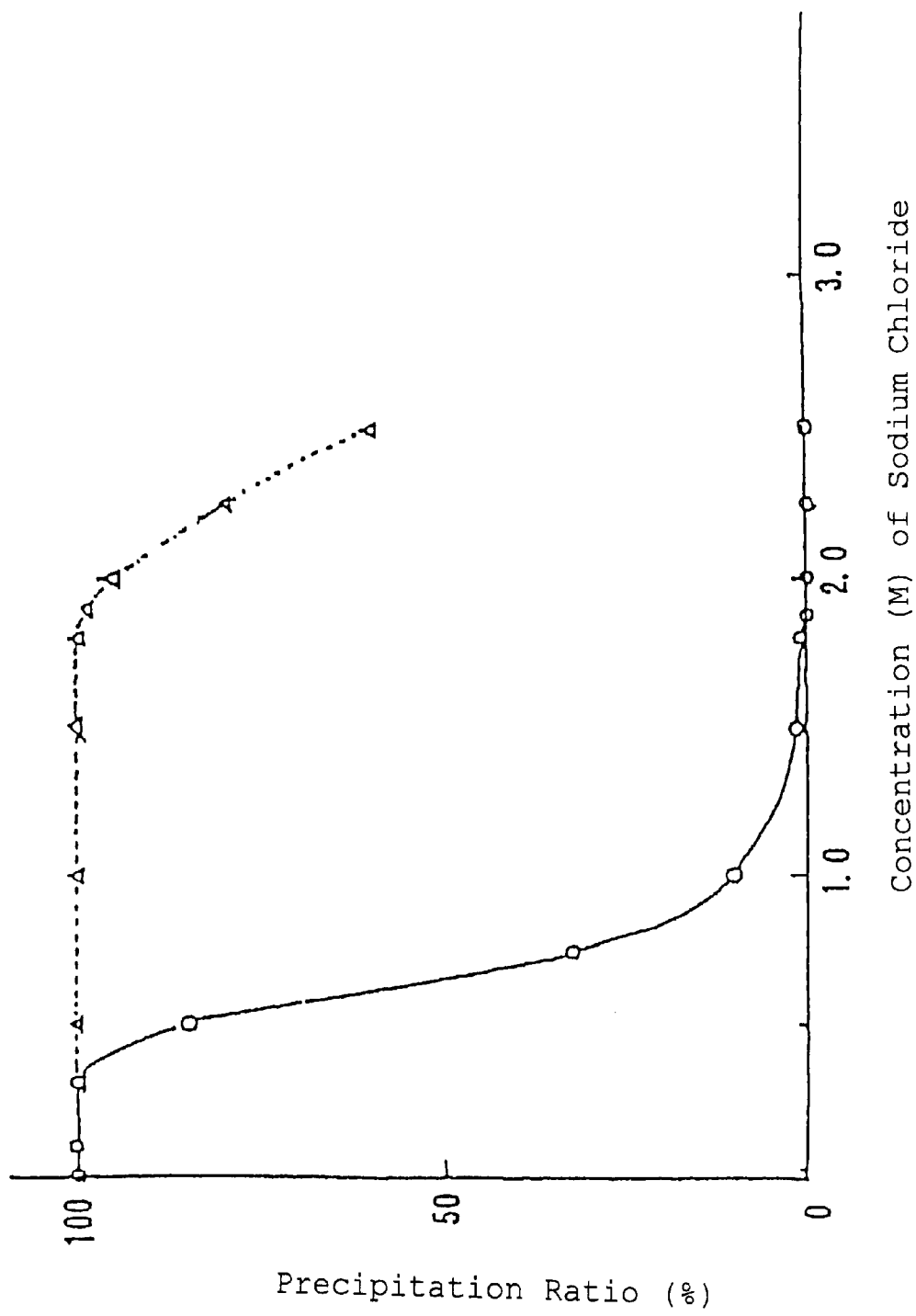
FIG. 2 shows the precipitation ratio of the sulfated-fucose-containing polysaccharide.

(2) FIG. 2 shows the precipitation ratio of the sulfated-fucose-containing polysaccharide-U and that of the sulfated-fucose-containing polysaccharide-F at various sodium chloride concentrations in the presence of cetylpyridinium chloride in excess.

In FIG. 2, the ordinate indicates the precipitation ratio (%) while the abscissa indicates the concentration (M) of sodium chloride. The solid line and open circle stand for the precipitation ratio of the sulfated-fucose-containing polysaccharide-U at various sodium chloride concentrations, while the dotted line and open triangle stand for the precipitation ratio of the sulfated-fucose-containing polysaccharide-F at various sodium chloride concentrations (M).

The precipitation ratios are determined at a solution temperature of 37° C. in the following manner.

The sulfated-fucose-containing polysaccharide-U and the sulfated-fucose-containing polysaccharide-F are each dissolved in water and 4 M of sodium chloride at a concentration of 2%. Then these solutions are mixed at various ratios to thereby give 125 μl portions of sulfated-fucose-containing polysaccharide-U and sulfated-fucose-containing polysaccharide-F solutions having various sodium chloride concentrations. Next, cetylpyridinium chloride was dissolved in water and 4 M of sodium chloride at a concentration of 2.5% and the obtained solutions are mixed at various ratios to thereby give 1.25% solutions of cetylpyridinium chloride with various sodium chloride concentrations.

3.2 times by volume as much the 1.25% solution of cetylpyridinium chloride is needed to completely precipitate the sulfated-fucose-containing polysaccharide-U and sulfated-fucose-containing polysaccharide-F each dissolved in water at a concentration of 2%. To 125 μl portions of 2% solutions of the sulfated-fucose-containing polysaccharide-U and the sulfated-fucose-containing polysaccharide-F with various sodium chloride concentrations were added 400 μl portions of cetylpyridinium chloride solutions with various sodium chloride concentrations. After thoroughly stirring and allowing to stand for 30 minutes, each mixture is centrifuged and the saccharide content of the supernatant is determined by the phenol-sulfuric acid method [Analytical Chemistry, 28, 350 (1956)] followed by the calculation of the precipitation ratio of each sulfated-fucose-containing polysaccharide at each sodium chloride concentration.

(3) Next, the components of the sulfated-fucose-containing polysaccharide-F are analyzed in the following manner.

First, the fucose content is determined in accordance with the method described in Journal of Biological Chemistry, 175, 595 (1948).

The dry preparation of the sulfated-fucose-containing polysaccharide-F is dissolved in 1 N hydrochloric acid to give a concentration of 0.5% and treated at 110° C. for 2 hours to thereby hydrolyze it into constituting monosaccharides. The reducing ends of the monosaccharides obtained by the hydrolysis are pyridyl-(2)-aminated (PA) by using GlycoTAG™ and GlycoTAG™ Reagent Kit (both manufactured by Takara Shuzo Co., Ltd.) and the composition ratio of the constituting monosaccharides is analyzed by HPLC.

Next, the content of uronic acid is determined in accordance with the method described in Analytical Biochemistry, 4, 330 (1962).

The content of sulfuric acid is determined in accordance with the method described in Biochemical Journal, 84, 106 (1962).

It is found out that the constituting saccharides of the sulfated-fucose-containing polysaccharide-F are fucose and galactose at a molar ratio of about 10:1. Neither uronic acid nor any other neutral saccharide is substantially contained therein. The molar ratio of fucose to sulfate is about 1:2.

The components of the sulfated-fucose-containing polysaccharide-U are determined in the above manner. As a result, it is found out that the constituting saccharides of the sulfated-fucose-containing polysaccharide-U are fucose, mannose, galactose, glucose, rhamnose, xylose and uronic acid and no other neutral saccharide is substantially contained therein. The composition ratio by mol of the major components is as follows; fucose:mannose:galactose:uronic acid sulfate group=about 10:7:4:5:20.

(4) When measured with a high-speed, high-sensitivity polarimeter SEPA-300 (manufactured by Horiba Seisakusho), the freeze-dried product of the sulfated-fucose-containing polysaccharide-F has a specific rotation of −135°.

On the other hand, the sulfated-fucose-containing polysaccharide-U has a specific rotation of −53.6°.

(5) Next, 16 ml of a 1% solution of sulfated-fucose-containing polysaccharide-F, 12 ml of a 50 mM phosphate buffer (pH 8.0), 4 ml of 4 M sodium chloride and 8 ml of a 32 mU/ml solution of the endofucoidanase described in the following Referential Example 5 are mixed together and reacted at 25° C. for 48 hours. As a result, no degradation product is formed.

The sulfated-fucose-containing polysaccharide-U and the fucoidanase described in Referential Example 5 are reacted at 25° C. for 48 hours under the above-mentioned condition. It is confirmed that the absorbance of the reaction mixture at 230 nm is elevated as the reaction proceeds, thus proving that the degradation of the sulfated-fucose-containing polysaccharide-U with this enzyme is in progress.

Referential Example 5

The fucoidanase described in Referential Example 4 is prepared in the following manner. There is no limitation for the strain to be used in the production of said fucoidanase as long as it is capable of producing said enzyme. As a particular example thereof, citation can be made of Flavobacterium sp. SA-0082 (FERM BP-5402).

This strain was detected in and collected from seawater in Aomori. This strain is indicated as Flavobacterium sp. SA-0082 and has been deposited at National Institute of Bioscience and Human-Technology, Agency of Industrial Science and Technology since Mar. 29, 1995 (date of the original deposit) under the accession number FERM BP-5402 as the international deposition.

The nutrients to be added to the medium for incubating this strain may be arbitrary ones so long as the strain employed can utilize them so as to produce the fucoidanase. Appropriate examples of the carbon source include fucoidan, marine alga powder, alginic acid, fucose, glucose, mannitol, glycerol, saccharose, maltose, lactose and starch, while appropriate examples of the nitrogen source include yeast extract, peptone, casamino acids, corn steep liquor, meat extract, defatted soybean, ammonium sulfate and ammonium chloride. The medium may further contain inorganic matters and metal salts such as sodium salts, phosphates, potassium salts, magnesium salts and zinc salts.

The yield of the fucoidanase produced by incubating the strain varies depending on the incubation conditions. In general, it is preferable that the incubation temperature ranges from 15 to 30° C. and the pH value of the medium ranges from 5 to 9. The yield of the fucoidanase attains the maximum by incubating the strain under aeration and agitation for 5 to 72 hours. As a matter of course, the incubation conditions are appropriately selected depending on the strain employed, the medium composition, etc. so as to achieve the maximum yield.

The fucoidanase is contained in both of the cells and the culture supernatant.

The above-mentioned Flavobacterium sp. SA-0082 is incubated in an appropriate medium and the cells are harvested and disrupted by a means commonly employed for disrupting cells such as ultrasonication. Thus a cell-free extract can be obtained.

Subsequently, the extract is purified by a purification procedure commonly employed in the art to thereby give a purified enzyme preparation. For example, the purification may be effected by salting out, ion exchange chromatography, hydrophobic bond column chromatography, gel filtration or the like to thereby give the purified fucoidanase.

The culture supernatant obtained by eliminating the cells from the above-mentioned culture medium also contains a large amount of this enzyme (extracellular enzyme) which can be purified by the same means as those employed for purifying the intracellular enzyme.

Now an example of the purification of the fucoidanase will be given.

Flavobacterium sp. SA-0082 (FERM BP-5402) is inoculated into 600 ml of a medium comprising an artificial seawater (pH 7.5, manufactured by Jamarin Laboratory) containing 0.25% of glucose, 1.0% of peptone and 0.05% of yeast extract which has been sterilized (120° C., 20 minutes) and pipetted into a 2-l Erlenmeyer flask. Then the strain is incubated therein at 24° C. for 24 hours to thereby give a seed culture. Into a 30-l jar fermenter is fed 20 l of a medium comprising an artificial seawater (pH 7.5, manufactured by Jamarin Laboratory) containing 0.25% of glucose, 1.0% of peptone, 0.05% of yeast extract and 0.01% of a defoaming agent (KM70 manufactured by Shin-Etsu Chemical Co., Ltd.) and sterilized at 120° C. for 20 minutes. After cooling, the medium is inoculated with 600 ml of the above-mentioned seed culture, which is then incubated therein at 24° C. for 24 hours under aerating at a rate of 10 l/minute and agitating at 125 rpm. After the completion of the incubation, the culture medium is centrifuged to thereby collect the cells.

These cells are suspended in a 20 mM acetate-phosphate buffer (pH 7.5) containing 200 mM of sodium chloride, disrupted by ultrasonication and centrifuged to thereby give a cell extract. The fucoidanase in this cell extract shows an activity of 5 mU/ml of the medium when determined by a method mentioned in Referential Example 3. Incidentally, the activity determination will be described later.

To this extract is added ammonium sulfate so as to establish 90% saturation finally. After dissolving by stirring, the mixture is centrifuged and the precipitate is suspended in the same buffer as the above-mentioned one in which the cells are suspended. Then the suspension is thoroughly dialyzed against a 20 mM acetate-phosphate buffer (pH 7.5) containing 50 mM of sodium chloride. After eliminating the precipitate formed by the dialysis by centrifugation, it is adsorbed by a DEAE-Sepharose FF column which has been equilibrated with a 20 mM acetate-phosphate buffer (pH 7.5) containing 50 mM of sodium chloride. Then the adsorbed matter is well washed with the same buffer and developed by linear concentration gradient elution with sodium chloride of 50 mM 600 mM. The active fractions are combined and sodium chloride is added thereto so as to give a final concentration of 4 M. Next, it is adsorbed by a Phenyl Sepharose CL-4B (manufactured by Pharmacia) column which has been equilibrated with a 20 mM phosphate buffer (pH 8.0) containing 4 M of sodium chloride. Then the adsorbed matter is well washed with the same buffer and developed by linear concentration gradient elution with sodium chloride of 4 M~1 M. The active fractions are combined and concentrated with an ultrafilter. Next, it is subjected to gel filtration with the use of Sephacryl S-300 (manufactured by Pharmacia) which has been equilibrated with a 10 mM phosphate buffer containing 50 mM of sodium chloride. The active fractions are combined. The molecular weight of the enzyme determined from the retention time in Sephacryl S-300 is about 460,000. Next, the active fraction is dialyzed against a 10 mM phosphate buffer (pH 7) containing 250 mM of sodium chloride. The enzyme solution is adsorbed by a Mono Q HR5/5 (manufactured by Pharmacia) column which has been equilibrated with a 10 mM phosphate buffer (pH 7) containing 250 mM of sodium chloride. The adsorbed matter is well washed with the same buffer and developed by linear concentration gradient elution with sodium chloride of 250 mM~450 mM. The active fractions are combined to thereby give the purified enzyme. Table 1 summarizes the above-mentioned purification steps. Incidentally, the protein is determined by measuring the absorbance of the enzyme solution at 280 nm. Calculation is made by taking the absorbance of a 1 mg/ml protein solution as 1.0.

TABLE 1

| Step | Total protein (mg) | Total activity (mU) | Specific activity (mU/mg) | Yield (%) |
|---|---|---|---|---|
| cell extract | 61,900 | 101,000 | 1.63 | 100 |
| ammonium sulfate-salting out | 33,800 | 88,600 | 2.62 | 87.7 |
| DEAE-Sepharose FF | 2,190 | 40,400 | 18.4 | 40.0 |
| Phenyl Sepharose CL-4B | 48.2 | 29,000 | 601 | 28.7 |
| Sephacryl S-300 | 7.24 | 19,600 | 2,710 | 19.4 |
| Mono Q | 0.824 | 15,000 | 18,200 | 14.9 |

Furthermore, the fucoidanase can be purified in the following manner. Flavobacterium sp. SA-0082 (FERM BP-5402) was inoculated into 600 ml of a medium comprising an artificial seawater (pH 7.5, manufactured by Jamarin Laboratory) containing 0.1% of glucose, 1.0% of peptone and 0.05% of yeast extract which had been pipetted into a 2-l Erlenmeyer flask and sterilized at 120° C. for 20 minutes. Then the strain was incubated therein at 24° C. for 20 hours to thereby give a seed culture. Into a 30-l jar fermenter was fed 20 l of a medium comprising an artificial seawater (pH 7.5, manufactured by Jamarin Laboratory) containing 0.3% of fucoidan originating in *Kjellmaniella crassifolia*, 0.5% of peptone, 0.01% of yeast extract and 0.01% of a defoaming agent (KM70 manufactured by Shin-Etsu Chemical Co., Ltd.) and sterilized at 120° C. for 20 minutes. After cooling, the medium was inoculated with 600 ml of the above-mentioned seed culture, which was then incubated therein at 24° C. for 20 hours under aerating at a rate of 10 l/minute and agitating at 125 rpm. After the completion of the incubation, the culture medium was centrifuged to thereby obtain the cells and the culture supernatant. The cells obtained by the main incubation were suspended in a 20 mM acetate-phosphate buffer (pH 7.5) containing 200 mM of sodium chloride, disrupted by ultrasonication and centrifuged to thereby give a cell extract. When the fucoidanase in this cell extract was assayed, an activity of 20 mU/ml of the culture medium was detected.

Separately, the culture supernatant was concentrated by ultrafiltration (exclusion molecular weight of membrane: 10,000, manufactured by Amicon) and the fucoidanase was assayed. Thus an activity of 6 mU/ml of the culture medium was detected.

To the above-mentioned concentrate of the culture supernatant was added ammonium sulfate so as to establish 90% saturation finally. After dissolving by stirring, the mixture was centrifuged and the precipitate was suspended in the same buffer as the above-mentioned one in which the cells were suspended. Then the suspension was thoroughly dialyzed against a 20 mM acetate-phosphate buffer (pH 7.5) containing 50 mM of sodium chloride. After eliminating the precipitate formed by the dialysis by centrifugation, it was adsorbed on a DEAE-Sepharose FF column which had been equilibrated with a 20 mM acetate-phosphate buffer (pH 7.5) containing 50 mM of sodium chloride. Then the adsorbed matter was well washed with the same buffer and developed by linear gradient elution with sodium chloride of 50 mM to 600 mM. The active fractions were combined and sodium chloride was added thereto so as to give a final concentration of 4 M. Next, it was adsorbed on a Phenyl Sepharose CL-4B column which had been equilibrated with a 20 mM phosphate buffer (pH 8.0) containing 4 M of sodium chloride. Then the adsorbed matter was well washed with the same buffer and developed by linear gradient elution with sodium chloride of 4 M to 1 M. The active fractions were combined and concentrated with an ultra filter (manufactured by Amicon). Next, it was subjected to gel filtration with the use of Sephacryl S-200 gel which had been equilibrated with a 10 mM phosphate buffer containing 50 mM of sodium chloride. The active fractions were combined and sodium chloride was added thereto so as to give a final concentration of 3.5 M. Next, it was adsorbed on a Phenyl Sepharose HP column which had been equilibrated with a 10 mM phosphate buffer (pH 8) containing 3.5 M of sodium chloride. Then the adsorbed matter was washed with the same buffer and developed by linear gradient elution with sodium chloride of 3.5 M to 1.5 M. The active fractions were combined to thereby give the purified enzyme. The molecular weight of the enzyme determined from the retention time in Sephacryl S-200 was about 70,000.

Example 1

(1) Alteromonas sp. SN-1009 (FERM BP-5474), a strain for producing an endo-sulfated-fucose-containing polysaccharide degrading enzyme was inoculated to a two-liter Erlenmeyer flask where 500 ml of medium consisting of artificial sea water (manufactured by Jamarin Laboratory) (pH 8.0) containing 0.25% of glucose, 1.0% of peptone and 0.05% of yeast extract was placed and sterilized (at 120° C. for 20 minutes) and then incubated at 25° C. for 23 hours. After completion of the incubation, the medium was centrifuged to collect the cells, one half of the resulting cells was suspended in 10 ml of extracting buffer [50 mM of Tris hydrochloride buffer (pH 8.0) and 100 mM of ethylenediaminetetraacetic acid (EDTA)], a solution (20 mg/ml of lysozyme dissolved in 1 ml of an extracting buffer) was added and the mixture was kept on an ice bath for 30 minutes . After that, 10 ml of a proteinase K solution [1 mg/ml of proteinase K, 50 mM Tris hydrochloride buffer (pH 8.0), 100 mM of EDTA and 1% of SDS] were added and the mixture was kept at 50° C. for two hours. Then, the mixture was returned to the room temperature, the same volume of phenol saturated with a TE buffer [10 mM of Tris hydrochloride buffer (pH 8.0) and 1 mM of EDTA] was added, the mixture was stirred gently for one hour and centrifuged at 10,000 rpm for 20 minutes and the upper layer was recovered (hereinafter, this operation will be referred to as a phenol extraction).

To this upper layer was added the same volume of a 1:1 mixture of phenol and chloroform saturated with a TE buffer followed by stirring gently and centrifuging at 10,000 rpm for 20 minutes and the upper layer was recovered (hereinafter, this operation will be referred to as a phenol/chloroform extraction). A phenol/chloroform extraction was carried out once again, sodium chloride was added to the aqueous layer to make it 0.1M, then a two-fold volume of ethanol was added to separate DNA and the resulting DNA was wound with a glass rod, rinsed with 80% ethanol and gently dried with air. This genome DNA was dissolved in 20 ml a TE buffer wherein ribonuclease A was dissolved in an amount of 20 μg/ml and the mixture was kept at 37° C. for five hours to degradete the RNA. After the phenol extraction and the phenol/chloroform extraction, ethanol was added by the same manner as above and DNA was recovered therefrom and suspended in 5 ml of a TE buffer. As a result of the above operations, about 20 mg of genome DNA were obtained.

(2) The genome DNA (100 μg) prepared in Example 1-(1) was digested with 10 units of a restriction enzyme Sau3AI at 37° C. for one minute and forty seconds to partially degrade, then a phenol/chloroform extraction was carried out and the upper layer was recovered. To the upper layer were added 0.1-fold volume of a 3M aqueous solution of sodium acetate (pH 5.0) and 2.5-fold volume of ethanol to precipitate DNA and the said DNA was rinsed with 80% ethanol and dried with air (hereinafter, this operation will be referred to as an ethanol precipitation) The resulting partially degraded product was subjected to a size fractionation by a gradient ultracentrifugation using 1.25M to 5M sodium chloride and DNA was recovered from the fractions containing the sizes of 10~20 kbp by means of an ethanol precipitation. The resulting partially degraded genome DNA (0.18 μg) and 0.6 μg of λ Blue Star BamHI arm (manufactured by Novagene) were mixed and ligated using a DNA Ligation Kit (manufactured by Takara Shuzo) and a packaging was applied to λ phage using a GigaPack II Gold kit (manufactured by Stratagene) to prepare a genome DNA library of Alteromonas sp. SN-1009.

(3) A purified enzyme protein (200 pmol) having a degrading activity of the endo-sulfated-fucose-containing polysaccharide obtained in Referential Example 1-(3) from Alteromonas sp. SN-1009 was applied to a column for desalting (Fast Desalting Column PC 3.2/10; manufactured by Pharmacia) equilibrated with 20 mM ammonium hydrogen carbonate and eluted with the same buffer and the buffer was substituted. The eluate was collected into a glass vial and concentrated and evaporated to dryness, the sample was placed together with the glass vial into a one-size-larger glass test tube in which 10 μl of pyridine, 2 μl of 4-vinylpyridine, 2 μl of tri-N-butylphosphine and 10 μl of water were placed, the glass test tube was sealed and a reaction was carried out at 95° C. for ten minutes to conduct a pyridylethylation. After completion of the reaction, the glass vial was taken out and subjected to an azeotropic treatment with water for several times to remove volatile components.

To the resulting pyridylethylated protein of the sulfated-fucose-containing polysaccharide degrading enzyme were added 40 μl of 10 mM Tris hydrochloride buffer (pH 9.0) containing 8M of urea, 90 μl of 10 mM Tris hydrochloride buffer (pH 9.0) and 0.5 pmol of Achromobacter protease I (manufactured by Takara Shuzo), a digestion was carried out at 30° C. overnight and the peptide fragments was purified from the resulting digested product by means of an HPLC system (Smart System; manufactured by Pharmacia). The column used was μRPC C2/C18 SC2.1/10 (manufactured by Pharmacia) and the flow rate was 100 μl/minute. In the elution, a 0.12% aqueous solution of trifluoroacetic acid (eluent A) and acetonitrile containing 0.1% of trifluoroacetic acid (eluent B) were used as eluents wherein a sample was applied when the ratio of the eluent B was 0% and elution was carried out by a linear concentration gradient method where the ratio of the eluent B was raised to 55% within 90 minutes to separate and purify. An amino acid sequence analysis was carried out for each of the peptide fractions and the partial amino acid sequences F27 (SEQ IDNO:9), F34 (SEQ ID NO:10), F47 (SEQ ID NO:11) and F52 (SEQ ID NO:12) were determined.

(4) The genome DNA (20 μg) prepared in Example 1-(1) was digested with each 100 units of restriction enzymes BamHI, EcoRI, HindIII, PstI, SacI, SalI, SphI and XbaI at 37° C. for four hours each and then extracted with phenol/chloroform. The digested product was recovered by means of an ethanol precipitation, each 10 μg thereof were digested with each 50 units of the same restriction enzymes at 37° C. for 16 hours each and extracted with phenol/chloroform and the digested product was recovered by means of an ethanol precipitation. Each 5 μg of the digested product were subjected to an electrophoresis using 0.8% agarose gel and the DNA was transferred to a Nylon membrane (trade name: Hybond-N+; manufactured by Amersham) by means of the Southern blotting (cf. "Method for Studying Genes, II, pages 218~221, published by Tokyo Kagaku Dojin).

As to the probe for hybridization, a mixed oligonucleotide pFDA27 (SEQ ID NO:13) was synthesized from the partial amino acid sequence F27 (SEQ ID NO:9) determined by Example 1-(3) and used therefor. The synthetic oligonucleotide (20pmol) was labeled with $^{32}$P using a Megalabel Kit (manufactured by Takara Shuzo).

The filter prepared as above was subjected to the prehybridization at 65° C. for three hours in a solution containing 6×SSC, 1% of SDS, 100 μg/ml of salmon sperm DNA and 5×Denhardt's solution, the labeled probe was added thereto to make the concentration 0.5 pmol/ml and the mixture was subjected to the hybridization at 42° C. overnight. After completion of the hybridization, the filter was washed with 6×SSC at room temperature for ten minutes, with 1×SSC in 0.1% of SDS at room temperature for ten minutes and with 1×SSC in 0.1% of SDS at 42° C. for 30 minutes. After removing an excess water, the filter was exposed to an Imaging Plate (manufactured by Fuji Photo Film) for 30 minutes and detected bands by a BAS 2000 Imaging Analyzer (manufactured by Fuji Photo Film).

The result was that the bands which hybridized to the probe were noted at the position of 23 kpb or more in the digested products with BamHI, EcoRI and SalI; at the positions of about 4.8, 1.4 and 0.3 kbp in the digested product with HindIII; at the positions of 23 kbp or more and 3.6 kbp in the digested product with PstI; at the positions of 23 kbp or more and 9.8 kbp in the digested product with SacI; at the positions of 23 kbp or more, 4.9 kbp and 3.0 kbp in the digested product with SphI; and at the positions of about 12, 5.2 and 3.5 kbp in the digested product with XbaI.

The clone containing the gene of the sulfated-fucose-containing polysaccharide degrading enzyme was screened by a plaque hybridization method according to the instructions for λ Blue Star of Novagene from the genome DNA library of Alteromonas sp. SN-1009 prepared in Example 1-(2). First, the phase library was infected with *Escherichia coli* ER1647 and spread onto four sheets of an L medium plate having a diameter of 8.5 cm to form about 500 plaques per plate. To this plate were applied Nylon membranes (trade name: Hybond-N+; manufactured by Amersham) in such a manner that the first sheet for about 30 seconds and the second one for about two minutes whereby the phase was transferred to each two sheets per plate. The Nylon membranes were denatured for five minutes on a filter paper dipped in a solution of 0.5M sodium hydroxide and 1.5M sodium chloride, then neutralized for five minutes on a filter paper dipped in 0.5M Tris hydrochloride buffer (pH 7.0) and 3M sodium chloride and rinsed with 2×SSC. The Nylon membranes were hybridized with the synthetic oligonucleotide pFDA27 (SEQ ID NO:13), washed and detected under the same condition as in the above-mentioned Southern hybridization to give 18 positive signals. Plaques near the positive signals were scraped off from the original plate and suspended in SM buffer whereupon plaques were formed again on new plates and the same operations were repeated, respectively. As results, 14 phage giving positive signal were isolated.

Each of the resulting phages was infected with *Escherichia coli* BM25.8 according to the instructions for λ Blue Star of Novagene, colonies resistant to ampicillin were selected and the phage was transformed into a form of plasmid. Colonies of each clone resulted as such were inoculated to L medium (1% of trypton, 0.5% of yeast extract and 0.5% of sodium chloride) containing 100 µg/ml of ampicillin and incubated at 37° C. overnight and plasmid DNAs were prepared from the resulting medium by the alkaline lysis method. *Escherichia coli* JM109 (manufactured by Takara Shuzo) was transformed using the said plasmid DNAs, colonies of each of the resulting clones were inoculated to L medium containing 100 µg/ml of ampicillin and incubated at 37° C. overnight and the resulting medium were subjected to the alkaline lysis method to prepare each of plasmid DNA again. The resulting plasmids of each of the clones were named pSFDA1, 2, 4, 5, 6, 7, 8, 10, 11, 12, 13, 14, 16 and pSFDA17, respectively.

Each plasmid was digested with restriction enzyme NotI at the both ends of cloning site of λ Blue Star vector and analyzed by means of a 0.3% agarose gel electrophoresis whereupon it was found that fragments of 8.4~17.4 kbp were inserted. Further, each plasmid was digested with restriction enzyme HindIII, subjected to the Southern blotting, hybridized with the synthetic oligonucleotide pFDA27 (SEQ ID NO:13) and analyzed whereupon it was classified into six groups consisting of a group giving bands of about 4.8 kbp (pSFDA1 and pSFDA17), that giving bands of about 4.8 and 0.3 kbp (pSFDA5, 6, 7 and pSFDA13), that giving a band of about 1.4 kbp (pSFDA10), that giving a band of about 0.3 kbp and bands of other sizes (pSFDA2 and pSFDA14), that giving a band of about 4.8 kbp and bands of other sizes (pSFDA16) and that giving a band of 5.0 kbp or more (pSFDA4, 8 and pSFDA12). However, except pSFDA10 giving a band of about 1.4 kbp, plural bands having the similar sizes were detected when stained with ethidium bromide at the agarose electrophoresis and, therefore, it was presumed that, in each plasmid, HindIII fragments of about 4.8 and 0.3 kbp or one of them or a part thereof were/was inserted in the genome DNA at nearly the same position. It was also presumed that the HindIII fragments of about 4.8 and 0.3 kbp hybridizing with this pFDA27 were located at very close positions on the genome. Accordingly, the resulting 14 plasmids may be roughly classified into pSFDA10 giving a band of about 1.4 kbp and other plasmids and it was presumed that they have any of about 4.8, 1.4 and 0.3 kbp or both of about 4.8 and 0.3 kbp detected by a Southern hybridization of the digested genome DNA with Hind III. Among the resulting plasmids, pSFDA7 having an inserted fragment of about 10.2 kbp and containing both HindIII fragments of about 4.8 and 0.3 kbp and pSFDA10 having an inserted fragment of about 8.4 kbp and containing a HindIII fragment of about 1.4 kbp were digested with several kinds of restriction enzymes and analyzed by means of an agarose electrophoresis to prepare a restriction enzyme map. At the same time, the region where hybridization was done with the synthetic oligonucleotide pFDA27 was subcloned to plasmid pUC119 and the like and the base sequence was analyzed by the dideoxy method. A sequence where 14 bases among 17 in pFDA27 were identical was found from the HindIII fragment of about 1.4 kbp of pSFDA10 but there was no agreement with the sequence coding for the amino acid sequence of F27 and, therefore, it was presumed that, although the said fragment hybridized with pFDA27, it has no relation with the gene of the endo-sulfated-fucose-containing polysaccharide degrading enzyme. On the other hand, a sequence coding for an amino acid identical with one of the sequences of pFDA27 and, including the surrounding sequences, identical with the partial amino acid sequence F27 (SEQ ID NO:9) determined in Example 1-(3) was found from both HindIII fragments of about 4.8 and 0.3 kbp of pSFDA7.

In addition, the HindIII fragments of about 4.8 kbp and 0.3 kbp were apart on a restriction enzyme map in about 3 kbp or more and were bigger than the size of the said enzyme gene which was supposed to have a molecular weight of about 100,000 as measured by a gel filtration of the endo-sulfated-fucose-containing polysaccharide degrading enzyme purified from Alteromonas sp. SN-1009 mentioned in Referential Example 1-(3) whereby it was presumed that there were at least two kinds of similar genes.

The *Escherichia coli* strain JM109 into which pSFDA7 was introduced will be expressed as *Escherichia coli* JM109/pSFDA7. Further, the *Escherichia coli* strain JM109 into which pSFDA7 was introduced expressed as *Escherichia coli* JM109/pSFDA7 has been deposited as FERM P-16362 on Aug. 1, 1997 with the National Institute of Bioscience and Human-Technology, Agency of Industrial Science and Technology and has been internationally deposited with the said National Institute of Bioscience and Human-Technology, Agency of Industrial Science and Technology as FERM BP-6340 (date of request for transfer to the international deposition: May 6, 1998).

With regard to pSFDA7, more detailed base sequence was analyzed by a dideoxy method using the primer extension method and the base sequence of 8.3 kbp in the inserted fragment of 10.2 kbp of pSFDA7 was determined whereupon two open reading frames—a reading frame 1 of 2646 bases (including termination codon) (hereinafter, referred to as ORF-1) and another reading frame 2 of 2445 bases (including termination codon) (hereinafter, referred to as ORF-2)—were found. The HindIII fragments of about 0.3 and 4.8 kbp detected in the Southern hybridization of genome DNA digested with HindIII were, to be more precise, in the lengths of 140 and 4549 base pairs respectively and contain a part of or whole length of ORF-1 and ORF-2, respectively. In the amino acid sequence coded by ORF-2, sequences having a very high homology with the partial amino acid sequences F34 (SEQ ID NO:10), F47 (SEQ ID NO:11) and F52 (SEQ ID NO:12) were found in addition to the sequence which was identical with the partial amino acid sequence F27 (SEQ ID NO:9) of the endosulfated-fucose-containing polysaccharide degrading enzyme. Accordingly, it is presumed that ORF-2 substantially codes for the endo-sulfated-fucose-containing polysaccharide degrading enzyme of Alteromonas sp. SN-1009. On the other hand, in the amino acid sequences coded by ORF-1, sequences having a high homology with the partial amino acid sequences F34 (SEQ ID NO:10) and F52 (SEQ ID NO:12) were found in addition to the sequence which was identical with the partial amino acid sequence F27 (SEQ ID NO:9) of the endo-sulfated-fucose-containing polysaccharide degrading enzyme whilst no sequence having a high homology with the partial amino acid sequence F47 (SEQ ID NO:11) was found. When the amino acid sequences coded by ORF-1 and ORF-2 were compared, there was an inserted sequence of 67 amino acid residues near the N-terminal of ORF-1 which was not found in ORF-2 and the amino acid sequence after the inserted sequence showed a very high homology of 70% or more whereby it was presumed that ORF-1 coded for the polypeptide having a degrading activity of the sulfated-fucose-containing polysaccharide as well. As such, total base sequences of the gene (ORF-2) which was believed to code for the polypeptide having a degrading activity of the sulfated-fucose-containing polysaccharide and of the gene (ORF-1) coding for a novel polypeptide which was believed to have a degrading activity of the sulfated-fucose-containing polysaccharide having a very high homology to the above gene were determined.

The result is shown in FIG. 1. Thus, FIG. 1 shows the positions of ORF-1 and ORF-2. In FIG. 1, black arrows indicate the coding region and direction of ORF-1 while arrows with oblique lines therein indicate the coding region and direction of ORF-2. The base sequence of ORF-1 is shown in SEQ ID NO:6 of the Sequence Listing while the amino acid sequence coded by ORF-1 is shown in SEQ ID NO:2 of the Sequence Listing. Further, the base sequence of ORF-2 is shown in SEQ ID NO:5 of the Sequence Listing while the amino acid sequence coded by ORF-2 is shown in SEQ ID NO:1 of the Sequence Listing.

As mentioned hereinabove, the gene (ORF-2) which is presumed to substantially code for the endo-sulfated-fucose-containing polysaccharide degrading enzyme and the gene (ORF-1) which is presumed to code for a novel polypeptide presumably having a degrading activity of the sulfated-fucose-containing polysaccharide have been isolated and purified in accordance with the present invention.

Example 2

In order to construct a direct expression vector of the gene (ORF-2), which was obtained in Example 1, presumably coding for the endo-sulfated-fucose-containing polysaccharide degrading enzyme substantially, the initiation codon of ORF-2 was made identical with the optimized initiation codon on the expression vector to construct a plasmid pEFDA-N where a part of the 5'-region of ORF-2 was inserted.

Firstly, synthetic DNA, FDA-N1 (SEQ ID NO:14) and FDA-N2 (SEQ ID NO:15) were synthesized. FDA-N1 is a synthetic DNA of 15 mer containing the sequence of the base sequence no. 1~13 of SEQ ID NO:5 of the Sequence Listing while FDA-N2 is a synthetic DNA of 15 mer containing the sequence complementary to the sequence of the base sequence no. 4~13 of SEQ ID NO:5 of the Sequence Listing.

Those synthetic DNAs were kept at 70° C. for ten minutes in a solution containing 0.2M of Tris hydrochloride buffer (pH 7.5) and 0.3M of sodium chloride, gradually cooled down to room temperature to form a double strands whereupon a synthetic DNA linker FDA-N was prepared. The resulting FDA-N was a synthetic DNA liner which contained the SnaBI site in he base sequence no. 8~13 of SEQ ID NO:5 of the Sequence Listing and was able to ligate with the NcoI site at the initiation codon and also with the BamHI site immediately downstream of the SnaBI site.

In the meanwhile, pET21d (manufactured by Novagene) which was an expression vector using T7 promoter was cleaved at the NcoI site containing the initiation codon optimized for expression at the downstream of T7 promoter and at the BamHI site in the multicloning site. This digested product was ligated with the already-prepared synthetic DNA linker FDA-N using DNA Ligation Kit (manufactured by Takara Shuzo), then *Escherichia coli* JM109 was transformed and colonies which grew on an L medium plate containing 100 μg/ml of ampicillin were selected. Each transformant was inoculated on an L medium containing 100 μg/ml of ampicillin, incubated at 37° C. overnight and plasmid DNA was prepared from the incubated cells by the alkaline lysis method. After digesting the plasmid DNA with SnaBI, 1% agarose gel electrophoresis was carried out to select the plasmid which was able to be cleaved by SnaBI, then the base sequence of the inserted fragment was confirmed by the didexoy method and the plasmid pEFDA-N where the region from the initiation codon of ORF-2 to the SnaBI site was inserted between the NcoI and BamHI sites of pET21d was obtained.

Then about 5 μg of the plasmid pSFDA7 obtained in Example 1 were digested at 37° C. for two hours with 30 units of SnaBI, separated by 1% agarose gel electrophoresis and the SnaBI fragment of about 2.5 kbp including nearly the whole length region of ORF-2 was cut out, extracted and purified. The SnaBI was mixed with the digested product of the already-constructed plasmid pEFDA-N with SnaBI and ligated using DNA Ligation Kit, then *Escherichia coli* JM109 was transformed and the colonies which grew on L medium plate containing 100 μg/ml of ampicillin were selected. Plasmid DNAs were prepared by the same manner as above, digested with SnaBI and subjected to a 1% agarose gel electrophoresis and the plasmid where SnaBI fragments of 2.5 kbp were liberated was selected. Further, the dideoxy method was carried out to confirm the direction of the inserted fragment and the plasmid where ORF-2 was inserted in the same direction as T7 promoter was selected. The expression plasmid where from the initiation codon at the NcoI site of pET21d to the whole length of ORF-2 was named pEFDAII103.

*Escherichia coli* strain BL21(DE3) (manufactured by Novagene) was transformed using the pEFDAII103 prepared as such. The resulting *Escherichia coli* BL21(DE3)/pEFDAII103 was inoculated to 5 ml of L medium containing 100 μg/ml of ampicillin and 5 mM of calcium chloride, subjected to a shake culture at 37° C., IPTG was added to make its final concentration 1 mM at the stage where the turbidity in terms of O.D.600 was 0.8 and subjected to a shake culture at 15° C. for one more night. After completion of the incubation, the medium was centrifuged to collect the cells and the cells were suspended in 1 ml of a buffer for disintegration of cells [20 mM of Tris hydrochloride buffer (pH 7.5), 10 mM of calcium chloride, 10 mM of potassium chloride and 0.3M of sodium chloride] and disintegrated by means of the ultrasonic wave treatment. They were centrifuged and the supernatant liquid was recovered and used as the *Escherichia coli* extract.

As a control, *Escherichia coli* BL21(DE3)/pET21d transformed with pET21d was incubated at the same time under the same condition and the resulting *Escherichia coli* extract was used for the following analysis.

Thus, at first, the *Escherichia coli* extracts were analyzed by an SDS polyacrylamide gel electrophoresis whereupon a band having a molecular weight of about 90,000, which was not found in the extract of *Escherichia coli* BL21(DE3)/pET21d, was observed in the extract of *Escherichia coli* BL21(DE3)/pEFDAII103 extract. This molecular weight well coincided with the molecular weight of the polypeptide (88,210) calculated from the amino acid sequence which was able to be coded by ORF-2 as shown in SEQ ID NO:1 of the Sequence Listing and also coincided with a molecular weight (about 90,000) obtained by analysis of an endo-sulfated-fucose-containing polysaccharide degrading enzyme purified from Alteromonas sp. SN-1009 by means of an SDS polyacrylamide gel electrophoresis. Accordingly, it has been confirmed that *Escherichia coli* BL21(DE3)/pEFDAII103 expresses a polypeptide coded by ORF-2.

Then the *Escherichia coli* extract's degrading activity of the endo-sulfated-fucose-containing polysaccharide was measured by a method mentioned in Referential Example 2.

The result was that 520 mU/ml of the endo-sulfated-fucose-containing polysaccharide degrading activity was detected from the extract of *Escherichia coli* BL21(DE3)/pEFDAII103. Thus, it has been found that the polypeptide for which ORF-2 codes has a degrading activity of the sulfated-fucose-containing polysaccharide and that the polypeptide for which ORF-2 codes having about 104 mU of degrading activity of the sulfated-fucose-containing polysaccharide is produced in 1 ml of the medium of *Escherichia coli* BL21(DE3)/pEFDAII103 having the gene of the present invention.

On the contrary, no endo-type degrading activity of the sulfated-fucose-containing polysaccharide was detected at all from the extract of *Escherichia coli* BL21(DE3)/pET21d.

Example 3

In ORF-1 and ORF-2, the sequences from initiation codon to the base 15 are entirely same and, within the said region, there is a restriction enzyme SnaBI site. Thus, the inserted sequence in the plasmid pEFDA-N constructed in Example 2 is entirely same in ORF-1 and in ORF-2 and, therefore, the pEFDA-N can be used for the construction of expression vector of ORF-1.

Thus, at first, about 5 μg of the plasmid pSFDA7 obtained in Example 1 were digested at 37° C. for two hours with 30 units of SnaBI, separated by means of a 1% agarose gel electrophoresis and the resulting SnaBI fragment of about 3.2 kbp including almost the whole length region of ORF-1 was cut out, extracted, and purified. After the SnaBI fragment was mixed with digested product of plasmid pEFDA-N with SnaBI and ligated by the use of DNA Ligation Kit, *Escherichia coli* JM109 was transformed with the mixture. The colonies which grew on L medium plate containing 100 μg/ml of ampicillin were selected.

Plasmid DNAs were prepared by the same manner as in Example 2, digested with SnaBI, and subjected to a 1% agarose gel electrophoresis and the plasmid where the SnaBI fragment of 3.2 kbp was inserted was selected. Further, confirmation of direction of the inserted fragment was carried out by the dideoxy method and the plasmid where ORF-1 was inserted in the same direction of T7 promoter was selected. The resulting expression plasmid where the full length of ORF-1 was inserted at the initiation codon in the NcoI site of pET21d was named pEFDAI103.

By the use of pEFDAI103 prepared as such, to expression of the polypeptide coded by ORF-1 and the degrading activity of the sulfated-fucose-containing polysaccharide of the polypeptide was confirmed using the same method as in Example 2.

Thus, firstly, *Escherichia coli* strain BL21(DE3) was transformed using pEFDAI103. The resulting *Escherichia coli* BL21(DE3)/pEFDAI103 was inoculated to a 5 ml of L medium containing 100 μg/ml of ampicillin and 5 mM of calcium chloride and cultured at 37° C. with shaking. After adding IPTG, at the turbidity in terms of O.D.600 was 0.8 to make its final concentration of 1 mM, and further the culture was incubated at 15° C. for one night more. After completion of the incubation, the culture was centrifuged to collect the cells. The cells were then suspended in 1 ml of the buffer for cell disintegration and disrupted by means of an ultrasonic wave treatment. This was centrifuged to recover the supernatant liquid to be used as an *Escherichia coli* extract.

The *Escherichia coli* extract was analyzed by means of an SDS polyacrylamide gel electrophoresis whereupon, in the extract of *Escherichia coli* BL21(DE3)/pEFDAI103, a band of a molecular weight of about 100,000, which was not found in the extract of *Escherichia coli* BL21(DE3)/pET21d, was observed. This molecular weight well coincided with the molecular weight (94,910) of the polypeptide calculated from the amino acid sequence for which ORF-1 can code as shown in SEQ ID NO:2 of the Sequence Listing and it has been confirmed that *Escherichia coli* BL21(DE3)/pEFDAI103 expresses the polypeptide for which ORF-1 codes.

Then the *Escherichia coli* extract's endo-sulfated-fucose-containing polysaccharide degrading activity was measured by the method mentioned in Referential Example 2.

The result was that, from an extract of *Escherichia coli* BL21(DE3)/pEFDAI103, 35.8 mU/ml of endo-sulfated-fucose-containing polysaccharide degrading activity was detected. Thus, it has been noted that the polypeptide for which ORF-1 codes has the degrading activity of the sulfated-fucose-containing polysaccharide and that, in 1 ml of the medium of *Escherichia coli* BL21(DE3)/pEFDAI103 having the gene of the present invention, the polypeptide coding for ORF-1 having about 7.2 mU of the degrading activity of the sulfated-fucose-containing polysaccharide is produced.

On the other hand, from the extract of *Escherichia coli* BL21(DE3)/pET21d, no degrading activity of the endo-sulfated-fucose-containing polysaccharide was detected at all.

Example 4

(1) Flavobacterium sp. SA-0082 (FERM BP-5402), which was a strain producing the fucoidanase, was incubated at 25° C. for 23 hours in a two-liter Erlenmeyer flask wherein 500 ml of medium consisting of artificial sea water (manufactured by Jamarin Laboratory) containing 0.25% of glucose, 1.0% of peptone and 0.05% of yeast extract had been placed and sterilized (at 120° C. for 20 minutes). After completion of the incubation, the medium was centrifuged to collect the cells, one half of the cells were suspended in 10 ml of extracting buffer [50 mM of Tris hydrochloride buffer (pH 8.0) and 100 mM of ethylenediaminetetraacetic acid (EDTA)], added 20 mg/ml lysozyme solution dissolved in 1 ml of the extracting buffer, and kept on an ice bath for 30 minutes. Then, 10 ml of proteinase K solution [1 mg/ml of proteinase K, 50 mM of Tris hydrochloride buffer (pH 8.0), 100 mM of EDTA and 1% of SDS] was added thereto and the mixture was kept at 50° C. for two hours. After that, the mixture was returned to room temperature, added equal volume of phenol saturated with TE buffer [10 mM of Tris hydrochloride buffer (pH 8.0) and 1 mM of EDTA] gently stirred for one hour, and centrifuged at 10,000 rpm for 20 minutes. The upper layer was recovered. To the upper layer was added a 1:1 mixture of phenol and chloroform saturated with TE buffer in the same volume. The mixture was gently stirred and centrifuged at 10,000 rpm for 20 minutes. The resulting upper layer was recovered. After extraction with phenol/chloroform was carried out again, sodium chloride was added to the aqueous layer to make it 0.1M, then two-fold volume of ethanol was added to precipitated the DNA. The DNA was wound up with a glass rod, rinsed with 80% ethanol, and gently air-dried. This genome DNA was dissolved in 20 ml of TE buffer, wherein 20 µg/ml of ribonuclease A was dissolved, and kept at 37° C. for five hours to degrade the RNA. After a phenol extraction and a phenol/chloroform extraction, ethanol was added thereto and DNA was recovered therefrom as the same method as before, and the DNA was suspended in 5 ml of a TE buffer. As a result of the above operations, about 20 mg of genome DNA were obtained.

(2) Genome DNA (100 µg) prepared in Example 4-(1) was digested with 10 units of a restriction enzyme Sau3AI at 37° C. for one minute and forty seconds to partially degrade followed by subjecting to a phenol/chloroform extraction to recover the upper layer. One-tenth volume of a 3M aqueous solution of sodium acetate (pH 5.0) and 2.5-fold volume of ethanol were added to the upper layer to precipitate the DNA and the precipitate was recovered by centrifugation, rinsed with 80% ethanol and air-dried. The resulting partially degraded product was subjected to a size fractionation by the density gradient ultracentrifugation using 1.25~5M sodium chloride and, from the fractions containing the sizes of 10~20 kbp, DNA was recovered by means of an ethanol precipitation. The resulting partially degraded genome DNA (0.2 µg) and 0.6 µg of λ Blue Star BamHI arm (manufactured by Novagene) were mixed, ligated by the DNA Ligation Kit (manufactured by Takara Shuzo) and subjected to the packaging to the lambda phage using a Gigapack II Gold kit (manufactured by Stragene), resulting in the genome DNA library of Flavobacterium sp. SA-0082.

(3) The purified fucoidanase protein (200 pmol) from Flavobacterium sp. SA-0082 obtained in Referential Example 5 was applied to a desalting column (Fast Desalting Column PC3.2/10; manufactured by Pharmacia) equilibrated with 20 mM of ammonium hydrogen carbonate, and eluted with the same buffer to substitute the buffer. After the eluate was collected into a glass vial, concentrated, and evaporated to dryness, the glass vial was placed in a one-size larger glass test tube containing 10 µl of pyridine, 2 µl of 4-vinylpyridine, 2 µl of tri-N-butylphosphine, and 10 µl of water. The glass test tube was sealed and the reaction was carried out at 95° C. for ten minutes to conduct pyridylethylation. After completion of the reaction, the glass vial was taken out and subjected to an azeotropic treatment with water for several times to remove the volatile components.

The resulting pyridylethylated fucoidanase protein was added with 40 µl of 10 mM Tris hydrochloride buffer (pH 9.0) containing 8M of urea, 90 µl of 10 mM Tris hydrochloride buffer (pH 9.0), and 0.5 pmol of Achromobacter protease I (manufactured by Takara Shuzo) and digested at 30° C. for one night. From the digested products, peptide fragments were purified by the HPLC System (Smart System; manufactured by Pharmacia). The column used was µRPC C2/C18 SC2.1/10 (manufactured by Pharmacia) and the flow rate used was 100 µl/minute. In the elution, 0.12% aqueous solution of trifluoroacetic acid (eluent A) and acetonitrile containing 0.1% of trifluoroacetic acid (eluent B) were used as eluents. The sample was applied when the ratio of the eluent B was 0% and the elution was carried out by means of the linear concentration gradient method where the ratio of the eluent B was raised up to 55% within 80 minutes. As the peaks eluted where the ratio of the eluent B was 27% or more, the eluted fractions L27, L31 and L36 were obtained. After that, the fractions in which the ratio of the eluent B was 17~27% where separation was poor were collected, concentrated, applied to the same HPLC system, and eluted by means of the linear concentration gradient method where the ratio of the eluent B was raised from 15% to 40% within 87 minutes to give eluted fractions LR8, LR9, LR14 and LR16. Each of the resulting peptide fractions was subjected to the amino acid sequence analysis to determine the partial amino acid sequences L27 (SEQ ID NO:16), L36 (SEQ ID NO:17), LR9 (SEQ ID NO:18), LR14 (SEQ ID NO:19) and LR16 (SEQ ID NO:20).

(4) Genome DNA (2.4 µg) prepared in Example 4-(1) was digested at 37° C. for three hours with 30 units of each of the restriction enzymes EcoRI, HindIII, MunI, SpeI, XbaI, and Sau3AI followed by subjecting to a phenol/chloroform extraction. The digested product was recovered by the ethanol precipitation. Each 0.5 µg of the digested product was mixed with the EcoRI cassette for the products digested with EcoRI and MunI; with the HindIII cassette for the product digested with HindIII; with the XbaI cassette for the products digested with SpeI and XbaI; and with the Sau3AI cassette for the product digested with Sau3AI where the cassette was used in an amount of 20 ng (in case of Sau3AI cassette, 200 ng) for each case (the cassettes are the products of Takara Shuzo), and then ligated using the DNA Ligation Kit (manufactured by Takara Shuzo). Each of the reaction product was recovered by the ethanol precipitation and dissolved in 10 µl of water to give a template DNA for the PCR using the cassette DNA.

In the meanwhile, from the amino acid sequence of 1~6 of the partial amino acid sequence LR14 (SEQ ID NO:19) determined in Example 4-(3), a mixed oligonucleotide pLl4F17 (SEQ ID NO:21) was synthesized in the same direction as that in the amino acid sequence while, from the amino acid sequence of 3~11 of the same, the mixed oligonucleotide pL14F26 (SEQ ID NO:22) was synthesized in the same manner.

Each reaction mixture was prepared that 1 µl of the already-prepared template DNA, 20 pmol of the cassette primer C1 (manufactured by Takara Shuzo), 100 pmol of the mixed oligonucleotide pL14F17 (SEQ ID NO:21), and sterilized water were mixed to make 22 µl and was heated at 94° C. for ten minutes followed by rapid cooling. To each mixtutre, 10 µl of ten-fold concentrated Ex Taq buffer (manufactured by Takara Shuzo), 16 µl of 1.25 mM each of dNTP mixed solution, 2.5 units of Takara Ex Taq (manufactured by Takara Shuzo), and sterilized water were added to make 100 µl and followed by layering with mineral oil. These mixtures were subjected to the amplification reaction using a thermal cycler (DNA Thermal Cycler 480; manufactured by Takara Shuzo) which was an automatic amplifier for gene. In the PCR, a cycle comprising denaturation at 94° C. for 0.5 minute, annealing at 45° C. for two minutes and a synthetic reaction at 72° C. for three minutes was carried out for 25 cycles and, finally, the mixtures were kept at 72° C. for seven minutes to complete the reaction.

After that, the second PCR was carried out using each of the template DNA, which was prepared by diluting the reaction solution of the first PCR to 10-fold with sterilized water, and heating at 94° C. for ten minutes followed by a rapid cooling. Thus, 10 μl of the heat-treated first PCR solution, 20 pmol of a cassette primer C2 (manufactured by Takara Shuzo), 100 pmol of the mixed oligonucleotide pL14F26 (SEQ ID NO:22), 10 μl of the ten-fold concentrated Ex Taq amplification buffer, 16 μl of 1.25 mM each of dNTP mixed solution, 2.5 units of Takara Ex Taq, and sterilized water were mixed to make 100 μl followed by layering with mineral oil. Each of the mixture was subjected to a cycle comprising denaturation at 94° C. for 0.5 minute, annealing at 55° C. for two minutes, and synthetic reaction at 72° C. for three minutes for 25 cycles and, finally, kept at 72° C. for seven minutes to complete the reaction. At the same time, the PCR was carried out for the reaction solutions consisting of cassette primer C2 only and the mixed oligonucleotide pL14F26 only and was used as a control for nonspecific amplified product for each primer.

When the reaction solution was analyzed by the agarose gel electrophoresis, plural amplified bands were detected in many of the reaction solutions and compared with the control reaction of non-specific amplified product. From those, a band of about 0.7 kbp was extracted and purified from the second PCR solution using MunI digest-EcoRI cassette as template where the background was relatively low and one band was strongly amplified. This DNA fragment was mixed with pT7blue T-Vector (manufactured by Novagene) and ligated using the DNA Ligation Kit. *Escherichia coli* JM109 was transformed with the ligation mixtute, and white colonies which grew on L medium plate containing 100 μg/ml of ampicillin, 0.04% of X-Gal, and 1 mM of IPTG were selected. After each transformant was inoculated in L broth containing 100 μg/ml of ampicillin and incubated at 37° C. overnight, plasmid DNA was prepared from the incubated cells by means of the alkaline lysis method, and a plasmid, into which the band of about 0.7 kbp was inserted, was selected and named pT7-Mun. The insertion sequence of this pT7-Mun was subjected to the base sequence analysis by the dideoxy method whereupon, succeeding to the sequence of pL14F26 used for the second PCR, a region coding for the amino acid sequence of the 12th amino acid and thereafter of the partial amino acid sequence LR14 (SEQ ID NO:19) was found. Further, at the downstream, a region coding for an amino acid sequence showing a very high homology with the partial amino acid sequence L27 (SEQ ID NO:16) was found. From those findings, it is apparent that the DNA fragment of about 0.7 kbp is a part of the fucoidanase gene. The sequence from the primer pL14F26 of the 0.7 kbp DNA fragment to the ligated point with the EcoRI cassette is shown in SEQ ID NO:23.

(5) Each 20 μg of the genome DNA prepared in Example 4-(1) was digested with 100 units each of the restriction enzyme BamHI, EcoRI, HindIII, PstI, SacI, SalI, SphI, or XbaI at 37° C. for four hours and extracted with phenol/chloroform. The digested product was recovered by means of the ethanol precipitation and each 10 μg thereof were again digested with 50 units of the same restriction enzyme at 37° C. for 16 hours, extracted with phenol/chloroform, and subjected to the ethanol precipitation to recover the digested product. Each 5 μg of the digest was subjected to a 0.8% agarose gel electrophoresis and transferred to a Nylon membrane (Hybond-N+manufactured by Amersham) by the Southern blotting method.

In the meanwhile, about 4 μg of pT7-Mun obtained in Example 4-(4) was digested with BamHI and SphI derived from vector, and the fragment of about 0.7 kbp liberated therefrom, which contained a part of the fucoidanase gene, was extracted and purified. The DNA fragment was labeled with $^{32}$P using the BcaBEST Labeling Kit (manufactured by Takara Shuzo) to prepare a probe DNA for hybridization.

The above-prepared filter was subjected to a prehybridization at 65° C. for one hour in a solution containing 6×SSC, 1% of SDS, 100 μg/ml of salmon sperm DNA, and 5×Denhardt's solution, then the labeled probe was added so as to make its concentration of 1,000,000 cpm/ml and hybridization was carried out at 60° C. for one night. After completion of the hybridization, the filter was washed in 6×SSC at room temperature for ten minutes, in 0.2×SSC and 0.1% of SDS at room temperature for ten minutes, in 0.2×SSC and 0.1% of SDS at room temperature for five minutes, and in 0.2×SSC and 0. 1% of SDS at 45° C. for 30 minutes to remove an excess water, exposed to the Imaging Plate (manufactured by Fuji Photo Film) for 30 minutes, and analyzed by BAS2000 Imaging Analyzer (manufactured by Fuji Photo Film).

The result was that, in the products digested with BamHI, SalI/SphI, and SalI, a band strongly hybridizing with the probe was noted at the position of 23 kbp or more; in that digested with EcoRI, two such bands at the positions of about 8 and 3 kpb; in that digested with HindIII, two such bands at the positions of about 11 and 4 kbp; in that digested with PstI, two such bands at the positions of about 12 and 2.5 kbp; in that digested with SacI, two such bands at the positions of about 10 and 9.5 kbp; and in that digested with XbaI, one such a band at the position of about 6 kbp. Accordingly, it was strongly suggested that there were two kinds of fucoidanase gene on the genome DNA of Flavobacterium sp. SA-0082.

(6) Clones containing fucoidanase gene were screened from the genome DNA library of Flavobacterium sp. SA-0082 prepared in Example 4-(2) by the plaque hybridization method according to the instructions for λ Blue Star of Novagene.

First, the phage library was infected with *Escherichia coli* ER1647 and about 300 plaques per plate were formed on five L medium plates having a diameter of 8.5 cm. Each of the plate was contacted with a Nylon membrane (Hybond-N+; manufactured by Amersham) for about 30 seconds so that the phage was transferred. The Nylon membranes were treated with 0.5M sodium hydroxide and 1.5M sodium chloride for five minutes for denaturation, and with 0.5M Tris hydrochloride buffer (pH 7.0) and 3M sodium chloride for five minutes for neutrization, and with 2×SSC for rinse and then air-dried. After irradiation with ultraviolet ray to fix the DNA, the Nylon membranes were hybridized, washed, and detected under the same condition used for the Southern hybridization mentioned in Example 4-(5) whereupon 36 positive signals were obtained. Plaques near the each positive signal was scraped off from the original plate and suspended in SM buffer to recover the phage. For some of the resulting phage solutions, plaques were formed again on new plates and the same operation was repeated whereupon nine phages giving positive signal were isolated.

In accordance with the instructions of Novagene for λ Blue Star, each of the resulting phages was infected with *Escherichia coli* BM25.8, spread on L medium plate containing 100 μg/ml of ampicillin and the colonies resistant to ampicillin were selected whereby the phage was converted to a form of a plasmid. Colony of each of the resulting clones was inoculated on L broth containing 100 μg/ml of ampicillin and incubated at 37° C. overnight, and plasmid DNA was prepared from the medium by the alkaline lysis method. *Escherichia coli* JM109 (manufactured by Takara Shuzo) was transformed using the said plasmid DNA, colony of each of the resulting clones was inoculated to L broth containing 100 μg/ml of ampicillin and incubated at 37° C. overnight, and the medium was subjected to the alkaline lysis method to prepare the plasmid DNA again. Plasmid of the each of the resulting clones was named pSFLA1, 5, 10, 11, 12, 13, 15, 17 and pSFLA18.

Each plasmid was digested with appropriate combinations of restriction enzymes KpnI, SacI and XbaI, subjected to the agarose gel electrophoresis, and then subjected to the Southern hybridization as mentioned above whereupon the restriction enzyme map for each inserted fragment was prepared and analyzed. The result was that, in the ethidium bromide staining of the agarose gel, plural bands having the bands in similar sizes were detected in each lane and, at the same time, it has been clarified that they are classified into two groups—one group consisting of pSFLA1, 10, 12, 15 and pSFLA18 where the bands, which hybridize with the inserted fragment of about 0.7 kbp of pT7-Mun, in SacI digest are two and the other group consisting of pSFLA5, 11, 13 and pSFLA17 where the bands, which hybridize with the inserted fragment of about 0.7 kbp of pT7-Mun, in KpnI digest are two. It has been further clarified that the three plasmids—pSFLA5, pSLFA10 and pSFLA17—release a fragment of about 6 kbp by digestion with XbaI, suggesting that the band of about 6 kbp in the XbaI-digested product, which detected by the Southern hybridization of Example 4-(5), is due to an overlapping of two bands and it is now apparent that there are at least two kinds of fucoidanase gene on genome DNA of Flavobacterium sp. SA-0082.

Thus, pSFLA10 and pSFLA17 were selected from the plasmids of each group and analysis of the inserted fragments was further carried out. Thus, about 3 μg of each of the plasmids was digested with XbaI and the liberated fragment of about 6 kbp was extracted and purified. Each of those XbaI fragments was mixed with XbaI-digested product of pHSG399 (manufactured by Takara Shuzo), which was a vector resistant to chloramphenicol, and ligated using the DNA Ligation Kit (manufactured by Takara Shuzo). Then *Escherichia coli* JM109 was transformed with the mixture and white colonies grown on L medium plate containing 30 μg/ml of chloramphenicol, 0.004% of X-Gal, and 1 mM of IPTG were selected. Each of the transformants was inoculated to L broth containing 30 μg/ml of chloramphenicol and incubated at 37° C. overnight. Then plasmid DNA was prepared from the incubated cells by means of the alkaline lysis method and analyzed by the agarose gel electrophoresis after digesting with restriction enzymes. The result was that pH10X6-1 and pH10X6-2 where the DNA of about 6 kbp derived from pSFLA10 was inserted in reversed directions, each other, were obtained. Similarly, pH17X6-7 and pH17X6-11, where the DNA of about 6 kbp derived from pSFLA17 was inserted, were obtained. The *Escherichia coli* strain JM109 into which pH10X6-1 was introduced, was named *Escherichia coli* JM109/pH10X6-1 and has been deposited as FERM P-16659 at the National Institute of Bioscience and Human-Technology, Agency of Industrial and Technology, MITI as from Feb. 24, 1998 and internationally deposited as FERM BP-6341 at the same organization (date of request for transferring to the international deposition: May 6, 1998). The *Escherichia coli* strain JM109, into which pH17X6-7 was introduced, was named *Escherichia coli* JM109/pH17X6-7 and has been deposited as FERM P-16660 at the National Institute of Bioscience and Human-Technology, Agency of Industrial and Technology, MITI as from Feb. 24, 1998 and internationally deposited as FERM BP-6342 at the same organization (date of request for transferring to the international deposition: May 6, 1998). When those plasmids were subjected to the base sequence analysis in detail by means of the primer extension method directly or by means of subcloning after digesting with a restriction enzyme, a reading frame of 2094 bases (including the termination codon) was found from the DNA fragment of about 6 kbp derived from pSFLA10 while a reading frame of 2115 bases (including the termination codon) was found from the DNA fragment of about 6 kbp derived from pSFLA17 and, in the amino acid sequences for which those reading frames code, regions having very high homology with the partial amino acid sequences determined in Example 4-(3) were found.

The reading frame derived from pSFLA10 was named fdlA while that from pSFLA17 was named fdlB.

Figure 3:
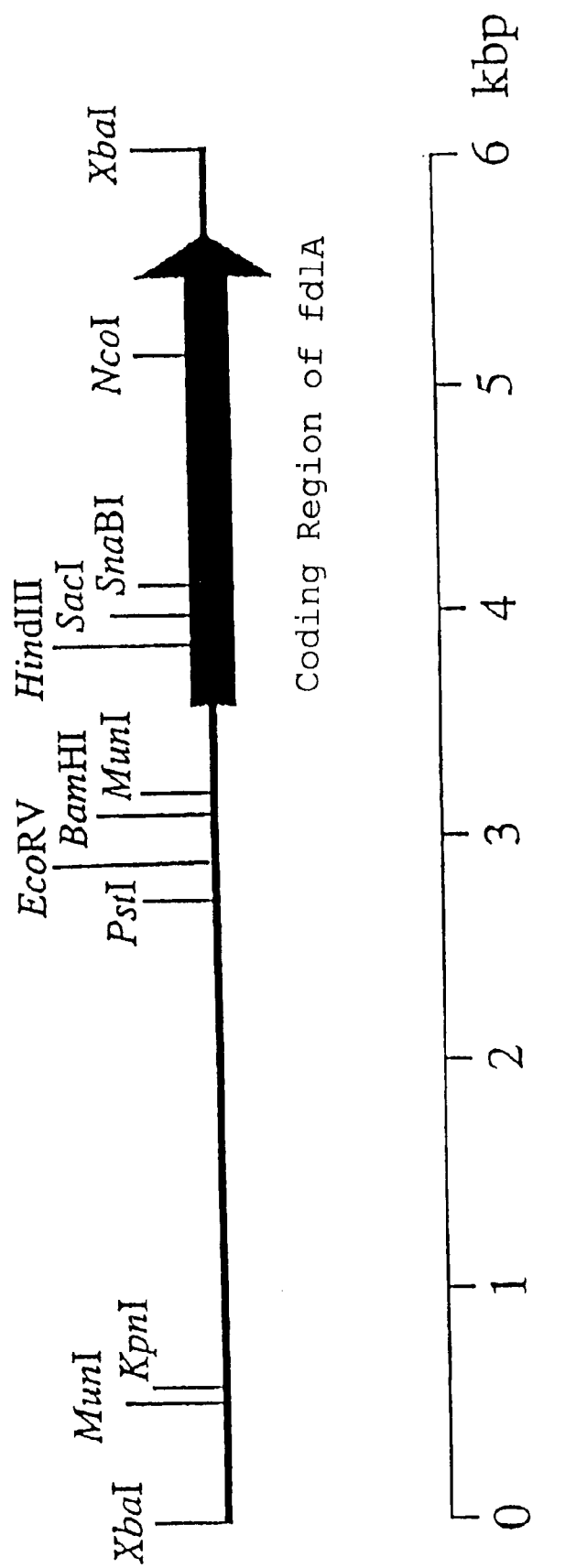
FIG. 3 shows the position of fdlA.
Figure 4:
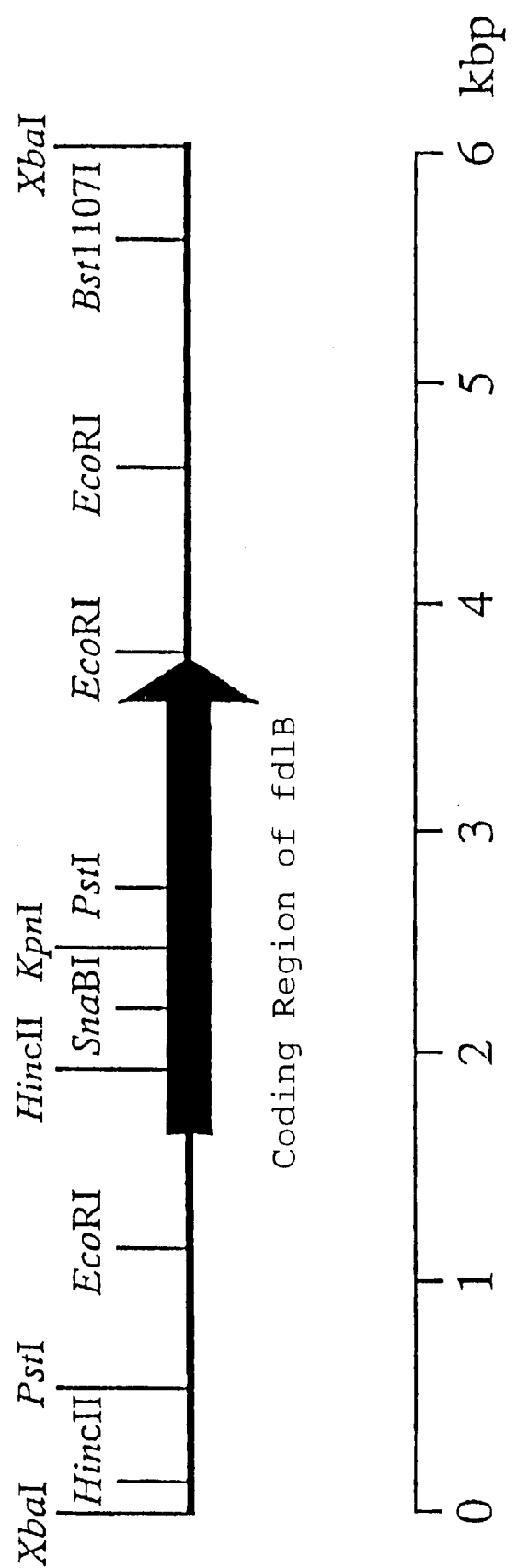
FIG. 4 shows the position of fdlB.

The result is shown in FIG. 3 and in FIG. 4. Thus, FIG. 3 shows the position of fdlA in pSFLA10 while FIG. 4 shows the position of fdlB in pSFLA10. Black arrow in FIG. 3 shows the coding region and direction of fdlA while that in FIG. 4 shows the coding region and direction of fdlB.

In the amino acid sequence for which fdlA codes, the sequences identical with partial amino acid sequence L36 (SEQ ID NO:17) and LR14 (SEQ ID NO:19) of the fucoidanase determined in Example 4-(3) were found and the sequences having a very high homology with partial amino acid sequence L27 (SEQ ID NO: 16), LR9 (SEQ ID NO:18) and LR16 (SEQ ID NO:20) of the fucoidanase determined in Example 4-(3) were found as well. Further, in the peptide fraction named LR8 in Example 4-(3), two amino acid derivatives for each cycle were detected by the amino acid sequence analysis whereby the amino acid sequence was not unconditionally determined. However, when the sequences in the two places in the amino acid sequence for which fdlA codes are applied, the amino acid derivative detected in each cycle can be explained and, therefore, it is now apparent that there were two peptides, each of which contained one of the sequences of the two places, in the said fraction. Those sequences were now named LR8-1 (SEQ ID NO:24) and LR8-2 (SEQ ID NO:25). As such, the amino acid sequences for which fdlA codes are identical or highly homologous with all of the amino acid sequences clarified by the partial amino acid sequence analysis of the fucoidanase of Example 4-(3) and, therefore, it is likely that they substantially code for the fucoidanase of Flavobacterium sp. SA-0082.

In the meanwhile, in the amino acid sequences for which fdlB codes, sequences which were identical with the partial amino acid sequences LR14 (SEQ ID NO:19) and LR8-1 (SEQ ID NO:24) of fucoidanase were found and sequences which showed a high homology with the partial amino acid sequences L27 (SEQ ID NO:16), LR16 (SEQ ID NO:20) and LR8-2 (SEQ ID NO:25) of the same were found as well although there was no sequence showing a high homology with the partial amino acid sequences L36 (SEQ ID NP:17) or LR9 (SEQ ID NO:18) . However, when fdlA and fdlB were compared, homologies of the base sequence and the amino acid sequence were as high as about 67% and about 56%, respectively whereby it is likely that fdlB codes for a polypeptide having the fucoidan-degrading activity as well. As such, total base sequences of gene (fdlA) which is presumed to code for the polypeptide having the fucoidan-degrading activity and the gene (fdlB) having a very high homology with the above gene were determined. The base sequence of fdlA is shown in SEQ ID NO:7 of the Sequence Listing while the amino acid sequence for which fdlA codes is shown in SEQ ID NO:3 of the Sequence Listing. Further, the base sequence of fdlB is shown in SEQ ID NO:8 of the Sequence Listing while the amino acid sequence for which fdlB codes is shown in SEQ ID NO:4 of the Sequence Listing.

As such, in accordance with the present invention, one gene (fdlA) which is presumed to substantially code for the fucoidanase and the other gene (fdlB), which is presumed to show a homology with the above gene and to code for the novel polypeptide presumably having the degrading activity of the sulfated-fucose-containing polysaccharide, have been isolated and purified.

Example 5

Firstly, a direct expression vector of the gene (fdlA), which was obtained in Example 4 presumed to substantially code for fucoidanase, was constructed.

In the plasmid pH10X6-1 obtained in Example 4, the XbaI fragment of about 6 kbp derived from pSFLA10 was inserted in such a direction that the fdlA gene was encountered to the lac promoter on vector. This pH10X6-1 was digested at SacI site located in the fdlA gene, then digested at BspHI located at the position of initiation codon of the fdlA gene, and separated by means of the 1% agarose gel electrophoresis, and the DNA fragments of about 400 bp coding for the N-terminal region of fdlA were cut out, extracted, and purified.

On the other hand, pET21d (manufactured by Novagene) which was an expression vector using the T7 promoter, was cleaved at the NcoI site, which contains the initiation codon optimized for expression and locates at the downstream of the T7 promoter, and also at the SacI site, which locates at the multicloning site, and then the BspHI-SacI fragments of about 400 bp coding for the N-terminal region of the already-prepared fdlA were inserted whereupon a plasmid pEFLA10-N was constructed.

Then the plasmid pH10X6-1 was digested with HindIII to cleave at the HindIII sites derived from the vector and inner side of the fdlA gene, and the DNA fragments of about 2 kbp, which codes for the C-terminal region including the termination codon of the fdlA gene, were cut out, extracted, and purified. The fragment was ligated with the HindIII-digested product of the already-prepared plasmid pEFLA10-N, and a plasmid, where the said HindIII fragments of 2 kbp are inserted to the direction where the whole length of the fdlA gene is regenerated, was selected. The expression plasmid, where the whole length of fdlA was inserted from the initiation codon located at the NcoI site of pET21d and which obtained as such, was named pEFLA10.

Then Escherichia coli strain BL21(DE3) (manufactured by Novagene) was transformed with the pEFLA10 prepared as such. The resulting Escherichia coli BL21(DE3)/pEFLA10 was inoculated to 5 ml of L broth containing 100 μg/ml of ampicillin and subjected to a shake culture at 37° C. When the O.D.600 of the culture was reached to 0.8, the culture was added IPTG to make its final concentration of 1 mM and further shaken at 15° C. for one night more. After completion of the incubation, the cells were collected from the medium by centrifugation, suspended in 0.5 ml of buffer for cell disintegration [20 mM of sodium phosphate buffer (pH 7.0) and 0.3M of sodium chloride], and disrupted by means of the ultrasonic wave treatment. A part of the suspension was taken out and used as the lysate of Escherichia coli. The suspension was further centrifuged to remove insoluble materials to prepare the Escherichia coli extract.

As a control, incubation was carried out at the same time under the same condition using Escherichia coli BL21 (DE3)/pET21d transformed by pET21d to prepare a lysate of Escherichia coli and an extract. They were used for the following analysis.

At first, the lysate of Escherichia coli was analyzed by means of the SDS polyacrylamide gel electrophoresis and, as a result, a band of a molecular weight of about 76,000 (which was not noted in the lysate of Escherichia coli BL21(DE3)/pET21d) was observed in the lysate of Escherichia coli BL21(DE3)/pEFLA10. The molecular weight well coincides with the molecular weight of the polypeptide (75,740) calculated from the amino acid sequence for which fdlA shown in SEQ ID NO:3 of the Sequence Listing is able to code, and also well coincides with the molecular weight (about 70,000) analyzed by the gel filtration of more purified fucoidanase of Flavobacterium sp. SA-0082 mentioned in Referential Example 5. Thus it has been confirmed that the Escherichia coli BL21(DE3)/pEFLA10 expresses the polypeptide coding for fdlA.

Then the degrading activity of the Escherichia coli extract for sulfated-fucose-containing polysaccharide was measured by the method mentioned in Referential Example 3.

The result was that the fucoidan-degrading activity of the extract of the Escherichia coli BL21(DE3)/pEFLA10 was found to be 2,300 mU/ml. Thus, it has been noted that the polypeptide for which fdlA codes has the fucoidan-degrading activity and that the polypeptide of about 230 mU, which is coded by fdlA and has the degrading activity of the sulfated-fucose-containing polysaccharide, was produced in 1 ml of the Escherichia coli BL21(DE3)/pEFLA10 containing the gene of the present invention.

On the contrary, no fucoidan-degrading activity was detected at all from the extract of the Escherichia coli BL21(DE3)/pET21d.

Example 6

A direct expression vector of fdlB which was the gene coding for the novel peptide presumed to have the degrading activity of the sulfated-fucose-containing polysaccharide obtained in Example 4 was constructed. A recognition sequence of BspHI was present in the position of the initiation codon of this fdlB gene but, since it was methylated due to influence of the upstream sequence thereof, the plasmid recovered from Escherichia coli JM109 used as a host was not able to be digested by BspHI directly. Therefore, a construction was carried out using DNA fragments amplified by means of the PCR.

In the plasmid pH17X6-7 obtained in Example 4, the XbaI fragments of about 6 kbp derived from pSFLA17 were inserted in the same direction as lac promoter on the vector and fdlB gene. Firstly, pH17X6-7 was cleaved at the KpnI site derived from the vector and inner area of fdlB gene, and self-ligated to construct the plasmid pH17X6-7K. Using pH17X6-7K as a template, PCR was carried out employing a pair of synthetic DNA primers, one of which was a synthetic DNA primer 17X6F4 (SEQ ID NO:26) and contained the same sequence and direction to a sequence locating at the upstream region from the coding region of fdlB and M13 primer M4 (manufactured by Takara Shuzo) capable to anneal to the vector. In conducting the PCR, a cycle consisting of denaturation at 94° C. for 0.5 minute, primer annealing at 55° C. for 0.5 minute, and synthetic reaction at 72° C. for one minute was conducted for 25 times in the same reaction solution composition as in Example 4-(4) and, finally, the mixture was kept at 72° C. for seven minutes to complete the reaction. The reaction solution was extracted with phenol/chloroform, and then the amplified DNA fragments of about 1 kbp were recovered by means of the ethanol precipitation. The fragment was cleaved at the BspHI site located at the position of the initiation codon of fdlB gene and also at the MflI site within its coding region, separated by means of the 3% agarose gel electrophoresis, extracted, and purified, resulting in the BspHI-MflI fragments of about 450 bp coding for the N-terminal region of fdlB.

On the other hand, as same as in Example 5, pET21d which was the expression vector using the T7 promoter was cleaved at the NcoI site and the BamHI site located in the multicloning site and inserted the already-prepared BspHI-MflI fragments of about 450 bp coding for the N-terminal region of fdlB to construct a plasmid pEFLA17-N.

Then the plasmid pH17X6-7 was cleaved at the NspV site located in the fdlB gene and at the EcoRI site located at the downstream of fdlB gene, and released NspV-EcoRI fragments of about 2 kbp, which coded for the C-terminal region including the termination codon of fdlB gene, were extracted and purified. The fragment was inserted between NspV and EcoRI of the already-constructed plasmid pEFLA17-N. The expression plasmid, thus constructed, in which the entire region of fdlB is inserted from the initiation codon at the NcoI site of pET21 d was named pEFLA17.

Using the plasmid pEFLA17 obtained as above, expression of polypeptide for which fdlB codes and the fucoidan-degrading activity of the polypeptide were confirmed by the same method as in Example 3.

Thus, at first, *Escherichia coli* strain BL21(DE3) was transformed with pEFLA17. The resulting *Escherichia coli* BL21(DE3)/pEFLA17 was inoculated to 5 ml of L broth containing 100 µg/ml of ampicillin, subjected to a shake culture at 37° C. When the O.D.600 of the culture was reached to 0.8, the culture was added IPTG to make its final concentration of 1 mM and further shaken at 15° C. for one night more. After completion of the incubation, the cells were collected from the medium by centrifugation, suspended in 0.5 ml of the cell disintegration buffer, and disrupted by means of the ultrasonic wave treatment. A part of the suspension was taken out and used as the *Escherichia coli* lysate. The suspention was further centrifuged to remove insoluble materials to prepare the *Escherichia coli* extract.

The lysate of *Escherichia coli* was analyzed by means of the SDS polyacrylamide gel electrophoresis and, as a result, a band of a molecular weight of about 77,000 (which was not noted in the lysate of *Escherichia coli* BL21(DE3)/pET21d) was observed in the lysate of *Escherichia coli* BL21(DE3)/pEFLA17. This molecular weight well coincides with the molecular weight of the polypeptide (76,929) calculated from the amino acid sequence (as shown in SEQ ID NO:4) for which fdlB is able to code. It has been confirmed that *Escherichia coli* BL21(DE3)/pEFLA17 expresses the polypeptide coding for fdlB.

Then the fucoidan-degrading activity of the *Escherichia coli* extract was measured by the method mentioned in Example 3.

The result was that 480 mU/ml of fucoidan-degrading activity was detected from the extract of *Escherichia coli* BL21(DE3)/pEFLA17. Thus, it has been understood that the polypeptide for which fdlB codes has the degrading activity of the sulfated-fucose-containing polysaccharide and that, in 1 ml of the medium of *Escherichia coli* BL21(DE3)/pEFLA17 having the gene of the present invention, the polypeptide of about 48 mU, which is coded by fdlB and has the degrading activity of the sulfated-fucose-containing polysaccharide, is produced.

On the contrary, no fucoidan-degrading activity was detected at all from the extract of *Escherichia coli* BL21(DE3)/pET21d.

Example 7

Action of the polypeptides, which have the degrading activity of the sulfated-fucose-containing polysaccharide obtained in Example 5 and Example 6, on sulfated-fucose-containing polysaccharide-U was investigated.

Thus, 10 µl of the polypeptide solution having the degrading activity of the sulfated-fucose-containing polysaccharide obtained in either Example 5 or Example 6 was added to a mixed solution of 50 µl of 100 mM phosphate buffer (pH 7.5), 50 µl of 2.5% sulfated-fucose-containing polysaccharide-U, and 10 µl of 4M sodium chloride and the mixture was kept at 25° C. A portion of the reaction solution was taken out at the stage of after 16, 40 and 65 hours from the initiation of the reaction, and the reaction products were analyzed by means of the HPLC. The conditions for the HPLC were as follows;

| | |
|---|---|
| Column | Shodex SB802.5 (manufactured by Showa Denko K.K.); |
| Column temperature | 25° C.; |
| Eluent | 50 mM aqueous solution of sodium chloride containing 5 mM of sodium azide; |
| Flow rate | 1 ml/minute; |
| Detector | Differential refractometric detector (Shodex RI-71; manufactured by Showa Denko K.K.); |

With regard to the reaction products, substances having the following structures have been known until now and, therefore, they were used as standard substances. Incidentally, the substances having the following formulae [I] to [IV] were manufactured as follows and used.

Dried *Kjellmaniella crassifolia* was disintegrated by a free disintegrator type M-2 (manufactured by Nara Kikai Seisakusho), treated in a 10-fold volume of 85% methanol at 70° C. for two hours and filtered. To the residue was added water of 20-fold amount and the mixture was treated at 100° C. for three hours and filtered to give an extract. Concentration of the salt in the extract was made as same as that of 400 mM sodium chloride, 5% of cetylpyridinium chloride were added thereto until no more precipitate was generated and the mixture was centrifuged. The resulting precipitate was well washed with ethanol to remove cetylpyridinium chloride completely, then desalting and removal of low-molecular substances were carried out by an ultrafilter (excluding molecular weight of the filtering membrane: 100,000) (manufactured by Amicon) and the precipitate generated thereby was removed by centrifugation. The supernatant fluid was freeze-dried to give purified fucoidan from *Kjellmaniella crassifolia*. The yield to the weight of dried *Kjellmaniella crassifolia* was about 4%.

Figure 5:
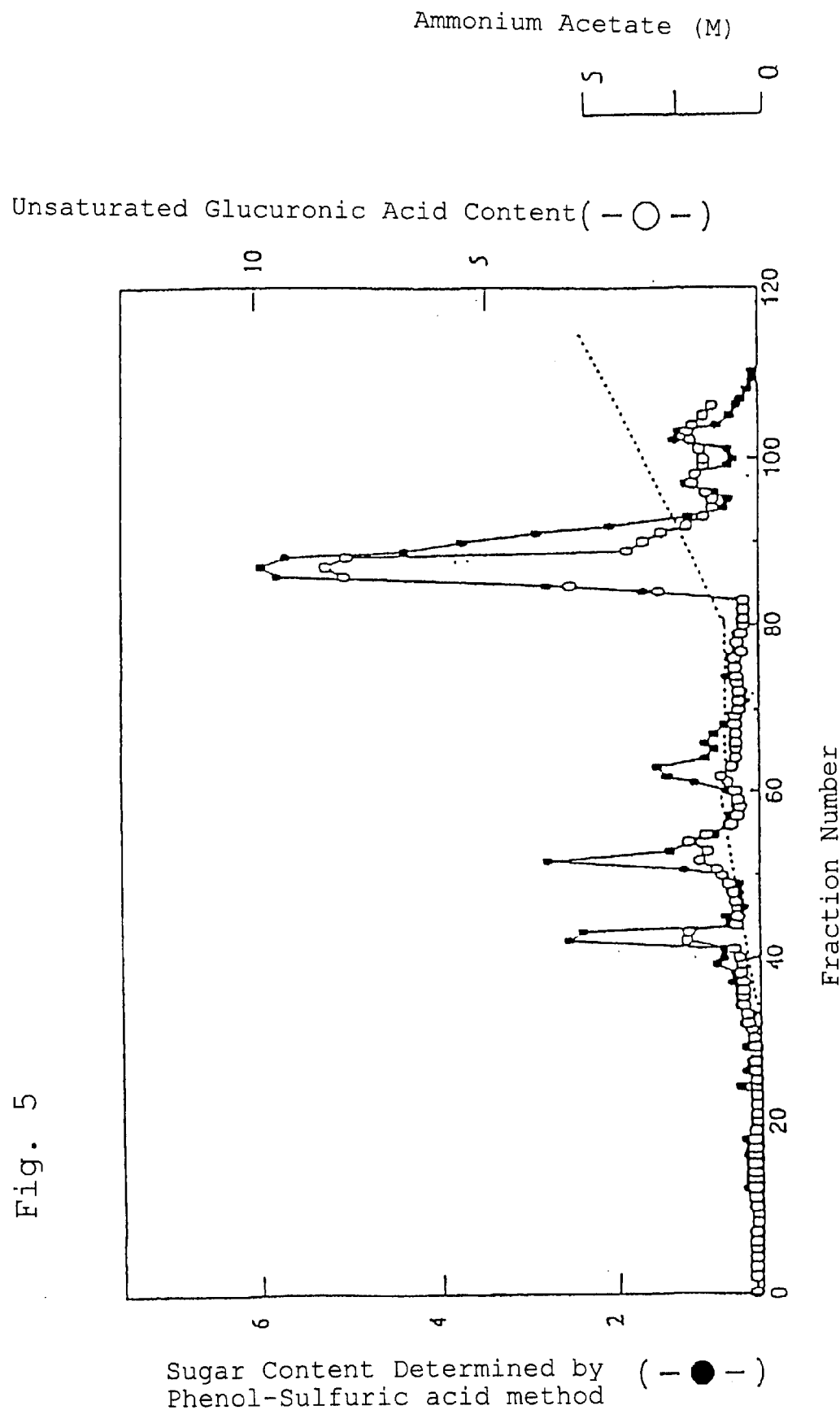
FIG. 5 is a chromatogram using the DEAE-Sepharose FF.

After that, 600 ml of a 5% solution of the said purified *Kjellmaniella crassifolia* fucoidan, 750 ml of 100 mM phosphate buffer (pH 8.0), 150 ml of 4M sodium chloride and 3.43 ml of a solution of fucoidanase (1750 mU/ml) mentioned in Referential Example 5 were mixed and made to react at 25° C. for 144 hours. The reaction solution was dialyzed using a permeable membrane having a pore size of 3500 to collect the fractions having a molecular weight of 3500 or less. The fractions were desalted by Micro Acilyzer G3 (manufactured by Asahi Kasei) and subjected to an ion-exchange chromatography using a column (4 cm×25 cm) of DEAE-Sepharose FF equilibrated with 10 mM ammonium acetate. Elution was carried out by means of a concentration gradient using ammonium acetate and the eluents were separated into every 50 ml. FIG. 5 shows the elution of the said chromatography. As a result of the said chromatography, the nine fractions (a)~(i) were obtained and, among them, the fractions (a), (b), (c) and (f) were used for analysis of the structure.

Then a structure analysis was carried out by a common method for the fractions (a), (b), (c) and (f) and, after confirming that the fractions (a), (b), (c) and (f) were the compounds represented by the following formulae [I], [II], [III] and [IV], respectively, each of the fractions was used as a standard for analysis of the above-mentioned reaction products.

Incidentally, the fraction numbers of the fractions in the above ion-exchange chromatography using the DEAE-Sepharose FF column were 42–43 for (a), 84–91 for (b), 51–52 for (c) and 62–63 for (f).

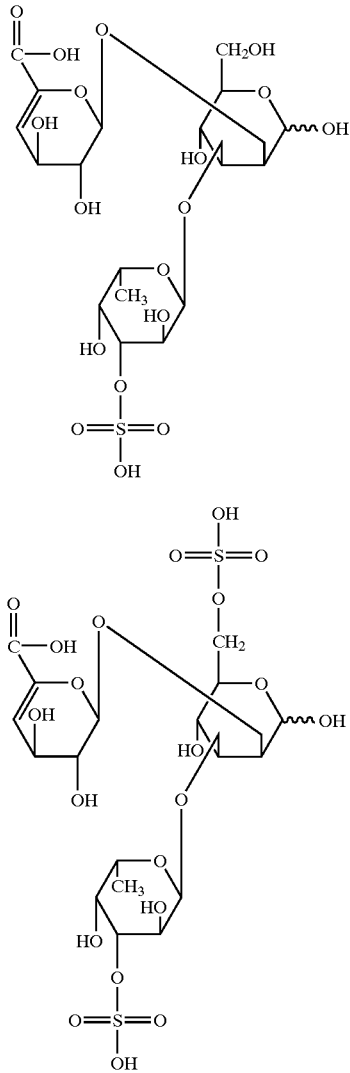

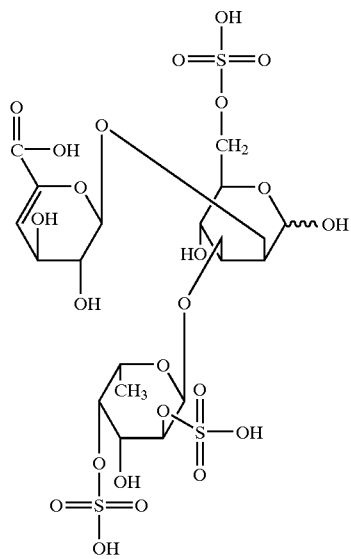

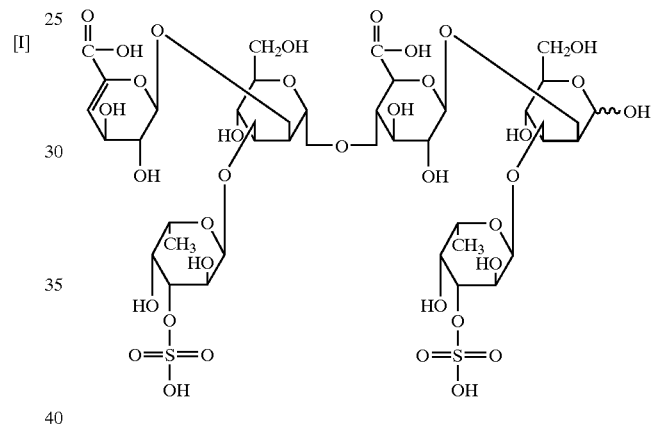

As a result of the analysis of the above reaction products, the products were only [I], [II] and [III] when the polypeptide having the degrading activity of the sulfated-fucose-containing polysaccharide obtained in Example 5 was used while, when the polypeptide having the degrading activity of the sulfated-fucose-containing polysaccharide obtained in Example 6 was used, the reaction products contained a large amount of [IV] in addition to the above-mentioned [I], [II], and [III] and, even when the reaction was continued further, [IV] was not decomposed to [I].

Thus, it has been found that the polypeptide encoded by fdlA obtained in Example 5 reacts with the sulfated-fucose-containing polysaccharide-U whereby the above-mentioned three saccharides [I], [II], and [III] are liberated as the final cleaved units while, in the case of the polypeptide encoded by fdlB obtained in Example 6, it reacts with the sulfated-fucose-containing polysaccharide-U to liberate the hexose such as the above [IV] as the final cleaved unit.

Example 8

In Example 5 and Example 6, it was confirmed that, by each recombinant *Escherichia coli* containing fdlA and fdlB gene, polypeptide for which the said each gene codes was produced respectively, that the degrading activity of the sulfated-fucose-containing polysaccharide was detected from the extract of said *Escherichia coli,* and that the polypeptide for which fdlA and fdlB code has the degrading activity of the sulfated-fucose-containing polysaccharide. However, when each of the *Escherichia coli* extract was analyzed by the SDS polyacrylamide gel electrophoresis, only a little amount of recombinant polypeptide was produced as compared with in the case of the lysate of *Escherichia coli* and it was suggested that only a part of the produced polypeptide was expressed as a soluble polypeptide of an active type in each case.

The fucoidanase of Flavobacterium sp. SA-0082 is an enzyme secreted to outside of the cells and is presumed to be expressed in a form of a precursor where the secreting signals for permeation of membrane are added to the N-terminal. In view of the above, the N-terminal amino acid sequence for which fdlA and fdlB code was investigated and it was presumed that the regions from the initiation methionine to the 25th and the 24th alanine residue were the secretory signals, respectively. Since it is thought that the presence of such hydrophobic secretory signals is related to the solubility of each of the recombinant polypeptides in Examples 5 and 6, expression plasmids wherefrom secretory signals of fdlA and fdlaB were removed were constructed respectively.

(1) Firstly, in order to introduce a restriction enzyme BamHI site into a direct upstream of the 26th glutamine residue from the initiation methionine of fdlA, primer FDL-Q-Bam (SEQ ID NO:27) and primer 10X6R4 (SEQ ID NO:28) were designed and synthesized. FDL-Q-Bam is a synthetic DNA of 28 mer where a BamHI site is oriented at the upstream of the sequence of the base sequence nos. 76~95 of SEQ ID NO:7 of the Sequence Listing while 10X6R4 is a synthetic DNA of 21 mer which is complementary to the sequence of base sequence nos. 1471~1491 of SEQ ID NO:7 of the Sequence Listing.

A PCR was carried out for a combination of primers FDL-Q-Bam and 10X6R4 using the pEFLA10 constructed in Example 5 as a template. In the PCR, a cycle consisting of denaturation at 94° C. for 0.5 minute, primer annealing at 50° C. for one minute and synthetic reaction at 72° C. for two minutes was conducted for 25 times in the same reaction solution composition as in Example 4-(4) and, finally, the mixture was kept at 72° C. for seven minutes to complete the reaction. The reaction solution was subjected to the agarose gel electrophoresis to separated and, after that, an amplified DNA fragment of about 1.4 kbp was extracted and purified. Then a plasmid DNA where the said fragment was inserted into pT7 Blue T-Vector (manufactured by Novagene) was prepared by the same manner as in Example 4-(4) and confirmed the base sequence. The resulting plasmid was cleaved at the BamHI site located at the primer FDL-Q-Bam and at the SnaBI site in fdlA coding region and separated by means of the 5% polyacrylamide gel electrophoresis, and resulting BamHI-SnaBI fragments of about 480 bp coding for the N-terminal region of the 26th glutamine residue from the initiation methionine of fdlA and thereafter were cut out, extracted and purified.

On the other hand, pET21a (manufactured by Novagene) which is an expression vector using the same T7 promoter as in Example 5 was cleaved at the HindIII site in the multicloning site and then the HindIII DNA fragment of about 2 kbp, which codes for the C-terminal region including the termination codon of the fdlA gene and was prepared in Example 5, was inserted in such a manner that the T7 promoter and the fdlA gene were in the same direction whereupon a plasmid pEFDLA-C was constructed. This PEFDLA-C was cleaved at the BamHI site derived from the multicloning site and at the SnaBI site in a fdlA coding region and then the already-prepared BamHI-SnaBI fragments of about 480 bp coding for the N-terminal region of the 26th glutamine residue from the initiation methionine of fdlA and thereafter was inserted whereupon a plasmid pEFDLA101 was prepared.

This plasmid pEFDLA101 codes for the polypeptide in which, at the downstream of a T7 promoter, the sequence of the 26th one in SEQ ID NO:3 of the Sequence Listing and thereafter were connected after the N-terminal sequence (SEQ ID NO:29) of 14 residues derived from pET21a.

(2) The sequence of the 20 bases after the 26th glutamine residue of fdlA using for the design of the primer FDL-Q-Bam was identical with the sequence (base sequence nos. 73–92 of SEQ ID NO:8 of the Sequence Listing) after the 25th glutamine residue of fdlB. Accordingly, the primer FDL-Q-Bam used in Example 8-(1) was directly able to be used for the construction of fdlB expression vector and, by the use of fundamentally the same method as in Example 8-(1), fdlB expression vector pEFDLB101 was constructed.

At first, in carrying out a PCR using FDL-Q-Bam, a synthetic DNA 17X6R1 (SEQ ID NO:30) of 20 mer complementary to the sequence of base sequence nos. 1489–1508 of SEQ ID NO:8 of the Sequence Listing was prepared. Using the pEFLB17 constructed in Example 6 as a template, a PCR was carried out for a combination of primers FDL-Q-Bam and 17X6R1, and the amplified DNA fragment of about 1.4 kbp was extracted and purified. The fragment was inserted into pT7 Blue T-Vector to prepare a plasmid DNA and its base sequence was confirmed.

After that, the resulting plasmid was cleaved at the BamHI site oriented at the primer FDL-Q-Bam and at the NspV site in the fdlB coding region and then separated by means of a 5% polyacrylamide gel electrophoresis whereby BamHI-NspV fragments of about 210 bp coding for the N-terminal region of the 25th glutamine residue from the initiation methionine of fdlB and thereafter were cute out, extracted and purified.

On the other hand, the plasmid pH17X6-7 obtained in Example 4 was cleaved at the EcoRI site and released EcoRI fragment of about 2.6 kbp including the whole length of the fdlB gene was cut out, extracted, and purified. The fragment was inserted into the EcoRI site in the multicloning site of pET21a so as to make the T7 promoter and the fdlB gene in the same direction whereupon a plasmid pEFDLB-W was constructed. This pEFDLB-W was cleaved at the BamHI site derived from the multicloning site and at the NspV site in fdlB coding region, and then the already-prepared BamHI-NspV fragment of about 210 bp, which codes for the N-terminal region of the 25th glutamine residue from the initiation methionine of fdlB and thereafter, was inserted to give a plasmid pEFDLB101.

This plasmid pEFDLB101 codes for the polypeptide in which, at the downstream of a T7 promoter, the sequence of the 25th one in SEQ ID NO:4 of the Sequence Listing and thereafter were connected after the N-terminal leader sequence (SEQ ID NO:29) of 14 residues which was just identical with the plasmid pEFDLA101 obtained in Example 8-(1).

(3) Incubation of recombinant and preparation of cell extract were carried out by the same manner as in Example 5 using pEFDLA101 and pEFDLB101 obtained in Example 8-(1) and (2) whereby comparison of the expressed amount and fucoidan-degrading activity of each recombinant polypeptide by pEFLA10 and pEFLA17 constructed in Examples 5 and 6 was carried out.

Thus, *Escherichia coli* strain BL21(DE3) was transformed with pEFLA10, pEFLA17, pEFDLA101 or pEFDLB101. Each of the resulting transformants was inoculated to 5 ml of L broth containing 100 µg/ml of ampicillin and subjected to a shake culture at 37° C. When O.D.600 of the culture reached to 0.8, the culture was added IPTG to make the final concentration of 1 mM and further incubated at 15° C. for one night more. After completion of the incubation, the cells were collected from the culture by centrifugation were suspended in 0.5 ml of buffer for cell disintegration, and disrupted by means of the ultrasonic wave treatment. A part of the suspension was taken out to be used as *Escherichia coli* lysate. The suspension was further centrifuged to remove insoluble materials whereupon *Escherichia coli* extract was obtained.

Each of the *Escherichia coli* lysates and extracts was analyzed by means of the SDS polyacrylamide gel electrophoresis followed by staining with Coomassie Brilliant Blue by the common method whereupon expression of large amount of polypeptide having the expected molecular weight was observed in all of the *Escherichia coli* lysates. At the same time, the expressed amount was estimated by means of a comparison with the amount of bovine serum albumin subjected to the electrophoresis and the fucoidan-degrading activity of each extract was measured by the method mentioned in Referential Example 3. Those results are given in Table 2.

TABLE 2

| Plasmid | Gene | Expressed Protein per Liter of Medium (mg/liter) | | Activity per ml of Medium (mU/ml) |
|---|---|---|---|---|
| | | (Lysate) | (Extract) | (Extract) |
| pEFLA10 | fdlA | 5 | 1 | 200 |
| pEFDLA101 | fdlA | 10 | 10 | 1300 |
| pEFLA17 | fdlB | 35 | * | 34 |
| pEFDLB101 | fdlB | 75 | 75 | 5700 |

*estimation impossible because of lower data than the detection limit

As shown in Table 2, with regard to the expressed amount of the desired polypeptide contained in the lysate, pEFDLA101 (fdlA) and pEFDLB101 (fdlB) wherein the construction was done in such a manner to add the N-terminal leader sequence instead of the sequence presumed to be the secretion signal showed higher productions to an extent of about two-fold in any of the genes as compared with the directly expressed plasmids pEFLA10 (fdlA) and EFLA17 (fdlB) having the presumed secretion signals.

It has been also clarified that, in the case of having secretion signals, the amount of the desired polypeptide existing in the extract is extremely small as compared with the lysate and much of the expressed polypeptide is present in an insoluble state while, in the case where secretion signals are removed, the desired polypeptide is detected in the extract in nearly the same amount as in the case of lysate and most of the expressed polypeptide is present in a soluble state. Further, the activity in the extract greatly increased corresponding to the existing amount of the desired polypeptide.

Example 9

Action of the polypeptide obtained in Example 2 and Example 3 having the degrading activity of the sulfated-fucose-containing polypeptide to sulfated-fucose-containing polysaccharide-F was investigated.

Thus, a polypeptide solution (100 µl) having 9.7 mU/ml of degrading activity of the sulfated-fucose-containing polysaccharide obtained in Example 2 or Example 3 was added to a mixture of 500 µl of 50 mM imidazole hydrochloride buffer (pH 7.5), 50 ml of a 2.5% solution of sulfated-fucose-containing polysaccharide-F mentioned in Referential Example 1-(2), 50 µl of 1M calcium chloride and 75 µl of 4M sodium chloride and then distilled water was added thereto to make the total amount 1 ml. After the reaction at 25° C. for 18 hours, the reaction product was analyzed by the HPLC. The conditions for the HPLC were as follows.

| | |
|---|---|
| Column | Shodex SB804 (manufactured by Showa Denko K.K.) |
| Column temperature | 25° C.; |
| Eluent | 50 mM aqueous solution of sodium chloride containing 5 mM of sodium azide; |
| Flow rate | 1 ml/min; |
| Detector | Differential refractometric detector (Shodex RI-71; manufactured by Showa Denko K.K.); |

The result of the analysis of the reaction product produced by the action of the polypeptide for which the gene of the present invention codes was that, in all of the reaction products using the polypeptide having the degrading activity of the sulfated-fucose-containing polysaccharide obtained in Example 2 and Example 3, two peaks of 8.62 and 9.30 minutes were detected in terms of a retention time in the HPLC.

Incidentally, when the case where the polypeptide having the degrading activity of the sulfated-fucose-containing polysaccharide obtained in Example 2 was compared with the case where the polypeptide having the degrading activity of the sulfated-fucose-containing polysaccharide obtained in Example 3, the substance of 9.30 minutes was produced in more amount than in the case of Example 2.

Advantage of the Invention

In accordance with the present invention, amino acid sequences and base sequences of the polypeptide having a degrading activity of the sulfated-fucose-containing polysaccharide have been firstly clarified whereby it is now possible to offer a polypeptide having a degrading activity of the sulfated-fucose-containing polysaccharide and, at the same time, an industrially advantageous method for the manufacture of a polypeptide having a degrading activity of the sulfated-fucose-containing polysaccharide by means of genetic engineering is offered.

In accordance with the present invention, it is not necessary to add a sulfated-fucose-containing polysaccharide to a medium for an inductive production of an enzyme having a degrading activity of the sulfated-fucose-containing polysaccharide whereby its productivity is high. In addition, no enzyme such as protease and other polysaccharide-degrading enzymes was simultaneously produced and purification is easy as well. Since the amino acid sequences and the base sequences of the polypeptide having a degrading activity of the sulfated-fucose-containing polysaccharide are offered, it is now possible to prepare a polypeptide antibody having a degrading activity of the sulfated-fucose-containing polysaccharide based upon the amino acid sequence and also to prepare probe and primer which are specific to the base sequence of the polypeptide having a degrading activity of the sulfated-fucose-containing polysaccharide based upon the base sequence.

What is claimed is:

1. An isolated gene having a DNA sequence encoding a polypeptide capable of degrading a sulfated-fucose-containing polysaccharide or having a functionally identical activity, wherein said gene is selected from the following:

(1) a gene having a DNA sequence encoding a polypeptide containing an amino acid sequence represented by either SEQ ID NO: 1 or SEQ ID NO: 2; wherein said polypeptide has a degrading activity which degrades a sulfated-fucose-containing polysaccharide having the following physiochemical properties:
  (a) constituting saccharide substantially free from uronic acid; and
  (b) substantially incapable of being degraded by the fucoidanase produced by Flavobacterium sp. SA-0082 (FERM BP-5402);

(2) a gene having a DNA sequence encoding a polypeptide containing an amino acid sequence represented by either SEQ ID NO: 3 or SEQ ID NO: 4; wherein said polypeptide had a degrading activity which degrades a sulfated-fucose-containing polysaccharide having the following physiochemical properties:
  (a) constituting saccharide containing uronic acid; and
  (b) being degraded by the fucoidanase produced by Flavobacterium sp SA-0082 (FERM BP-5402) and degrades the said sulfated-fucose-containing polysaccharide whereby at least one of the following formulae

[I]

[II]

[III]

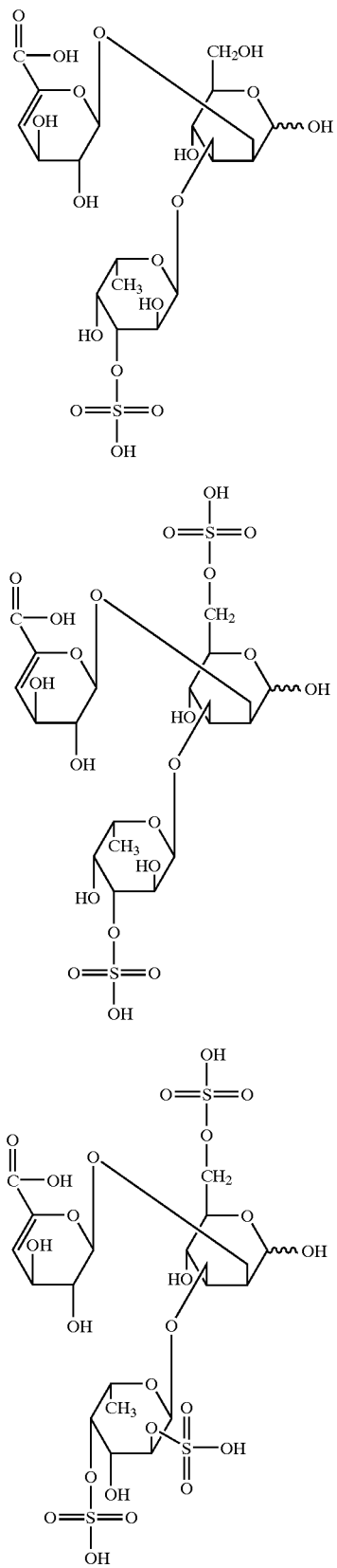

[IV]

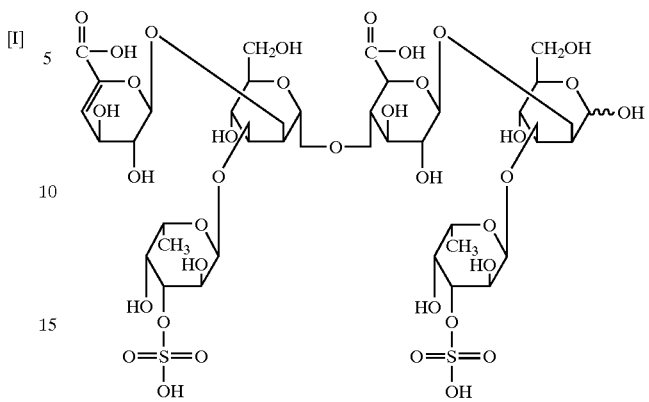

is liberated; and (3) a gene having a DNA sequence which hybridizes to (1) or (2) in 6×SSC, 1% SDS, 5×Denhardt's solution and 100 μg/ml of salmon sperm DNA at 65° C.

2. A gene according to claim 1 in which the polypeptide is derived from bacteria belonging to genus Alteromonas.

3. A gene according to claim 1 in which the polypeptide is derived from bacteria belonging to genus Flavobacterium.

4. A gene according to claim 1 in which is characterized in that said gene has a DNA sequence represented by any one of the SEQ ID NO: 5 to SEQ ID NO: 8, has a DNA sequence which hybridizes to any one of the SEQ ID NO: 5 to SEQ ID NO: 8 in 6×SSC, 1% SDS, 5×Denhardt's solution and 100 μg/ml of salmon sperm DNA at 65° C.

5. A recombinant DNA containing the gene according to claim 1.

6. An expression vector comprising a promoter operably linked with the DNA of claim 5.

7. A transformant which is transformed by the expression vector according to claim 6.

8. A method for producing a polypeptide having a degrading activity of the sulfated-fucose-containing polysaccharide or that having functionally identical activity as that, characterized in that, transformant according to claim 7 is incubated and polypeptide having a degrading activity of the sulfated-fucose-containing polysaccharide or that having functionally identical activity as that is collected from the incubated product.

9. An isolated polypeptide having an amino acid sequence represented by any one of SEQ ID NO: 1 to SEQ ID NO: 4; or having an amino acid sequence encoded by a DNA sequence which hybridizes to any one of the SEQ ID NO: 5 to SEQ ID NO: 8 in 6×SSC, 1% SDS, 5×Denhardt's solution and 100 μg/ml of salmon sperm DNA at 65° C., wherein said polypeptide has a degrading activity of either the following:

1. having a degrading activity which degrades a sulfated-fucose-containing polysaccharide having the following physiochemical properties:
   (a) constituting saccharide substantially free from uronic acid; and
   (b) substantially incapable of being degraded by the fucoidanase produced by Flavobacterium sp. SA-0082 (FERM BP-5402); or 2. having a degrading activity which acts on a sulfated-fucose-containing polysaccharide having the following physiochemical properties:
   (a) constituting saccharide containing uronic acid; and
   (b) being degraded by the fucoidanse produced by Flavobacterium sp SA-0082 (FERM BP-5402) and degrades the sulfated-fucose-containing polysaccharide whereby at least one of the following formulae
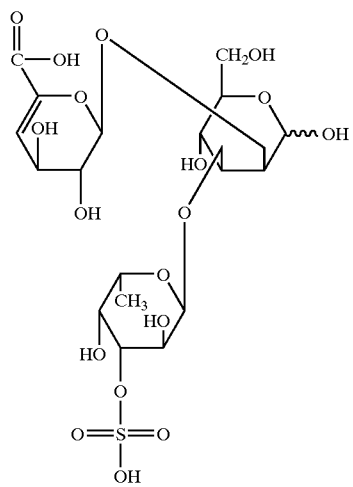
[I]
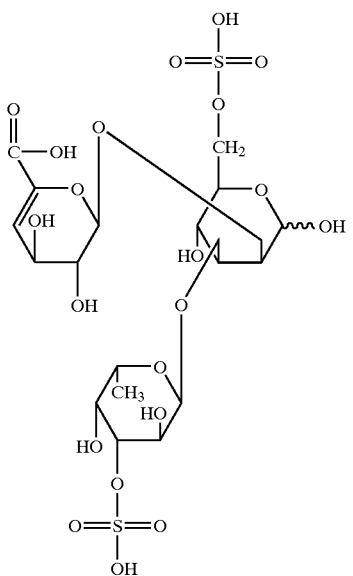
[II]
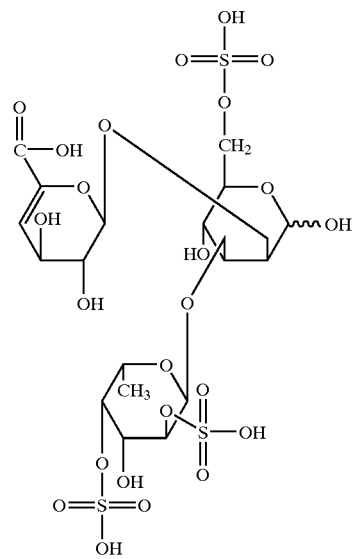
[III]
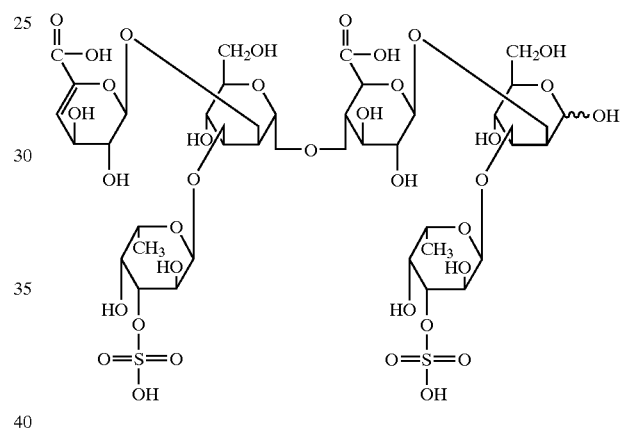
[IV]
is liberated.
* * * * *

SEQUENCE LISTING

<160> NUMBER OF SEQ ID NOS: 30

<210> SEQ ID NO 1
<211> LENGTH: 814
<212> TYPE: PRT
<213> ORGANISM: Bacteria

<400> SEQUENCE: 1

| | | | | | | | | | | | | | | |
|---|---|---|---|---|---|---|---|---|---|---|---|---|---|---|
| Met | Lys | Ile | Arg | Asn | Val | Cys | Arg | Ser | Ala | Val | Leu | Gly | Leu | Met |
| 1 | | | | 5 | | | | | 10 | | | | | 15 |
| Ser | Leu | Asn | Thr | Tyr | Ala | Glu | Thr | Lys | Ala | Asp | Trp | Met | Gln | Gly | Asn |
| | | | 20 | | | | | 25 | | | | | 30 | | |
| Trp | Gly | Ile | Ser | Tyr | Arg | Ile | Pro | Gly | Gly | Asp | Ile | Asn | Tyr | Ser | Gly |
| | | | 35 | | | | | 40 | | | | | 45 | | |
| Ser | His | Val | Ala | Glu | Tyr | Asn | Val | Arg | Ala | Ala | Val | Glu | Gln | Ile | Ser |
| | | | 50 | | | | | 55 | | | | | 60 | | |
| Ala | Ile | Pro | Gly | Leu | Lys | Trp | Val | Gln | Ile | Asn | Leu | Thr | Asn | Gly | Ala |
| 65 | | | | | 70 | | | | | 75 | | | | | 80 |
| Ser | Gly | Asp | Arg | Phe | Ile | Val | Pro | Val | Thr | Glu | Val | Glu | Ala | Ile | Asn |
| | | | | 85 | | | | | 90 | | | | | 95 | |
| Pro | Leu | Ser | Ala | Pro | Asn | Ser | Ile | Asn | Asp | Leu | Tyr | Asp | Pro | Thr | Leu |
| | | | | 100 | | | | | 105 | | | | | 110 | |
| Pro | Gly | Arg | Asp | Leu | Phe | Glu | Gln | Leu | Ala | Leu | Ala | Phe | Lys | Ala | Lys |
| | | | | 115 | | | | | 120 | | | | | 125 | |
| Gly | Ile | Arg | Val | Val | Ala | Tyr | Ile | Ala | Thr | Gln | Gly | Pro | Gly | Met | Leu |
| | | | 130 | | | | | 135 | | | | | 140 | | |
| Lys | His | Gly | Ala | Glu | Asn | Ser | Met | Asp | Glu | Asp | Ser | Ile | Thr | Asp |
| 145 | | | | | 150 | | | | | 155 | | | | | 160 |
| Cys | Lys | Ser | Ser | Lys | Pro | Leu | Val | Thr | Asp | Leu | Asp | Thr | Gln | Val | Tyr |
| | | | | 165 | | | | | 170 | | | | | 175 | |
| Cys | Ser | Ala | Asn | Met | Asn | Arg | Trp | Arg | Asp | Tyr | Val | Leu | Glu | Gln | Tyr |
| | | | | 180 | | | | | 185 | | | | | 190 | |
| Pro | Ser | Thr | Ser | Leu | Tyr | Arg | Ser | Phe | Glu | Leu | Ala | Met | Val | Asn | Ile |
| | | | | 195 | | | | | 200 | | | | | 205 | |
| Val | Glu | Thr | Leu | Ser | Leu | Arg | Tyr | Gly | Ser | Thr | Ile | Asp | Gly | Trp | Trp |
| | | | 210 | | | | | 215 | | | | | 220 | | |
| Phe | Asp | His | Ser | Gly | Phe | Gly | Asp | Ser | Glu | Leu | Leu | His | Ala | Ala | Ala |
| 225 | | | | | 230 | | | | | 235 | | | | | 240 |
| Leu | Ala | Gly | Asn | Asn | Asp | Ala | Ala | Val | Ala | Phe | Asn | Glu | Gly | Asp | Lys |
| | | | | 245 | | | | | 250 | | | | | 255 | |
| Val | Pro | Leu | Val | Asn | Asn | Pro | Glu | Thr | Leu | Asp | Asp | Tyr | Thr | Phe | Gly |
| | | | | 260 | | | | | 265 | | | | | 270 | |
| His | Pro | Thr | Pro | Ile | Gly | Ser | Glu | Val | Ser | Ser | Asp | Lys | Asn | Leu |
| | | | | 275 | | | | | 280 | | | | | 285 | |
| Pro | Met | Leu | Thr | Ser | Ile | Glu | Ala | Thr | Leu | Asp | Gly | Ile | Leu | Thr | Gly |
| | | | | 290 | | | | | 295 | | | | | 300 | |
| Ser | Gly | Asp | Asp | Val | Gly | Ser | Val | Gly | His | Met | Phe | Met | Pro | Leu | Gln |
| 305 | | | | | 310 | | | | | 315 | | | | | 320 |
| Glu | Ser | Trp | Asn | Gly | Gly | Thr | Val | Val | Phe | Ser | Glu | Ala | Lys | Gly | Ser |
| | | | | 325 | | | | | 330 | | | | | 335 | |
| Asp | Trp | Leu | Asn | Arg | Ala | Leu | Lys | Ala | Gly | Gly | Ala | Phe | Thr | Trp | Ala |
| | | | | 340 | | | | | 345 | | | | | 350 | |

-continued

```
Leu Ser Gln Asp Ser Asn Asp Glu Leu Gly Gly Gly Ala Arg Leu
        355                 360                 365
Ile Ser Glu Pro Gln Val Lys Met Leu Glu Arg Met Ser Phe Asn Ile
    370                 375                 380
Gly Lys Gln Leu His Met Asn Leu Asp Gly Ser Asp Gly Asp Thr Ala
385                 390                 395                 400
Tyr Asp Asp Ser Val Asn Gln Tyr Thr Ala Thr Val Asn Gly Ala Asn
                405                 410                 415
Phe Val Asp Asp Val Thr Arg Gly Lys Val Ala Ser Phe Thr Glu Asp
                420                 425                 430
Asp Gln Leu Glu Leu Asp Asn Tyr Gln Gly Ile Ser Gly Gly Asn Ala
            435                 440                 445
Arg Thr Thr Met Ala Trp Ile Lys Thr Ser Asp Ser Lys Gly Asp Ile
        450                 455                 460
Ile Asp Trp Gly Asn Asn Thr Thr Ser Glu Arg Trp Trp Leu Arg Leu
465                 470                 475                 480
Val Asp Gly Lys Phe Lys Leu Ile Leu Lys Gly Pro Asn Leu Thr Gly
                485                 490                 495
Thr Thr Thr Leu Asn Asp Asp Gln Trp His His Ile Ala Val Val Ala
            500                 505                 510
Ser Asp Asn Val Val Ala Asn Ile Lys Val Tyr Ile Asp Gly Val Leu
        515                 520                 525
Glu Thr Val Ala Val Asn Asp Asn Ala Ser Thr Thr Phe Asp Thr Thr
    530                 535                 540
Leu Gly Gly Asn Ile Gln Ile Gly Gly Ala Tyr Thr Gly Leu Ile Asp
545                 550                 555                 560
Lys Val Leu Val His Asp Arg Ala Leu Asp Glu Ser Glu Ile Glu Tyr
                565                 570                 575
Val Val Asn Ser Ser Asn Ala Asp Leu Asp Leu Glu Val Ala Leu Asp
            580                 585                 590
Val Arg Phe Glu Glu Ser Ala Asn Ser Thr Lys Val Thr Asp Asn Ser
        595                 600                 605
Ile Tyr Gly Arg His Gly Thr Asn Arg Gly Ala Ile Thr Gly Val Phe
    610                 615                 620
Asp Ala Glu Arg Asn Ser Asn Val Tyr Ser Leu Asp Gly Val Asp Ser
625                 630                 635                 640
Gly Glu Asp Ile Asn Asp Leu Lys Asp Ser Asp Tyr Glu His Glu Val
                645                 650                 655
Val Met Thr Thr Asp Asn Ser Lys Asp Ser Lys Gly Tyr Ser Gly Val
            660                 665                 670
Asn Gly Ala Gly Pro Arg Thr Val Met Ala Trp Ile Lys Thr Thr Phe
        675                 680                 685
Gly Gly Ala Val Ile Ala Gln Trp Gly Asn Lys Asn Ser Val Asp Gly
    690                 695                 700
Glu Gln Tyr Glu Val Arg Leu Lys Asn Gly Ala Leu Arg Leu Asp Ile
705                 710                 715                 720
Thr Gly Gly Ile Ile Lys Gly Thr Ser Ile Asn Asp Gly Glu Trp
                725                 730                 735
His His Ile Ala Val Val Ser Pro Asp Glu Gln Leu Ala Asn Thr Lys
            740                 745                 750
```

-continued

```
Leu Tyr Val Asp Gly Val Leu Glu Thr Ala Thr Thr Ser Gly Ser Gln
            755                 760                 765

Ala Thr Ile Asp Thr Lys Thr Leu Asn Gly Asp Ser Lys Asp Val Ile
        770                 775                 780

Ile Gly Ser Thr Phe Val Gly Glu Met Asp Asp Phe Ile Ile His Gln
785                 790                 795                 800

Arg Ala Leu Arg Gln Phe Glu Val Lys Asn Ser Ala Gly Leu
                805                 810

<210> SEQ ID NO 2
<211> LENGTH: 881
<212> TYPE: PRT
<213> ORGANISM: Bacteria

<400> SEQUENCE: 2

Met Lys Ile Arg Asn Met Cys Cys Thr Ala Leu Ile Val Ser Leu Met
1               5                   10                  15

Gly Cys Gly Gly Ser Gly Ser Glu Ala Ser Ser Pro Glu Val Glu Val
            20                  25                  30

Asp Asn Gly Val Glu Ile Gln Pro Glu Pro Glu Val Glu Pro Glu Pro
        35                  40                  45

Glu Val Glu Pro Glu Pro Glu Val Glu Pro Glu Pro Glu Val Glu Pro
50                  55                  60

Glu Pro Glu Val Glu Pro Glu Pro Glu Val Glu Pro Glu Pro Glu Val
65                  70                  75                  80

Glu Pro Glu Pro Glu Asp Ile Arg Ala Ser Trp Met Gln Gly Asn Trp
                85                  90                  95

Gly Ile Ser Phe Arg Ile Ser Gly Gly Asp Ile Ser Gln Asn Glu Ser
            100                 105                 110

His Val Asn Glu Tyr Gln Val Ala Pro Ala Val Glu Gln Ile Ala Ala
        115                 120                 125

Ile Pro Gly Leu Lys Trp Leu Gln Val Asn Leu Ser Asn Gly Ala Phe
    130                 135                 140

Gly Asp Arg Phe Ile Val Pro Val Pro Glu Val Glu Ala Ile Asn Pro
145                 150                 155                 160

Asn Ser Ala Pro Asn Ser Ser Ala Asp Leu Phe Asp Pro Ala Leu Pro
                165                 170                 175

Gly Asp Asp Leu Phe Glu Gln Ile Ala Leu Gly Leu Gln Ala Lys Gly
            180                 185                 190

Ile Lys Val Val Ala Tyr Ile Ala Thr Gln Gly Pro Ala Met Leu Lys
        195                 200                 205

His Gly Ala Glu Arg Ser Met Asp Phe Asp Asp Ser Ile Val Asp Glu
    210                 215                 220

Ser Asp Gly Ser Ala Cys Lys Ser Ser Arg Pro Val Val Ser Asp Pro
225                 230                 235                 240

Asp Thr Gln Val Tyr Cys Ser Ala Asn Met Asn Arg Trp Arg Asp Tyr
                245                 250                 255

Val Leu Gln Gln Tyr Pro Ser Thr Ser Leu His His Ser Phe Gln Leu
            260                 265                 270

Gly Leu Val Asn Ile Val Glu Thr Leu Ser Leu Arg Tyr Gly Thr Leu
        275                 280                 285
```

-continued

```
Ile Asp Gly Trp Trp Phe Asp His Ser Ile Tyr Gly Asp Tyr Asn Leu
    290                 295                 300

Leu Pro Asp Ala Ala Arg Ala Gly Asn Ser Asn Ala Ala Val Ser Leu
305                 310                 315                 320

Asn Leu Glu Gly Asp Ile Phe Leu Ser Asn Asn Pro Glu Val Met Glu
                325                 330                 335

Asp Phe Thr Gly Gly His Pro Thr Pro Ile Ala Arg Val Val Ser Ser
                340                 345                 350

Asp Asp Thr Asn Leu Pro Met Leu Thr Ala Ile Glu Asp Ala Pro Asn
        355                 360                 365

Gly Ile Phe Thr Gly Thr Gly Asp Val Asp Ala Leu Gly His Met
370                 375                 380

Phe Leu Pro Leu Gln Glu Thr Trp Asn Gly Thr Val Val Phe Ser
385                 390                 395                 400

Glu Ala Lys Gly Thr Glu Trp Leu Asn Arg Val Thr Arg Ala Gly Gly
                405                 410                 415

Ala Leu Thr Trp Ala Leu Ser His Glu Gly Ser Val Ser Gly Gly Glu
                420                 425                 430

Ala Met Leu Ile Ser Ala Pro Gln Ala Lys Met Leu Ala Arg Met Gln
        435                 440                 445

Leu Asn Ile Gly Lys Gln Leu Asp Met Asp Leu Asp Gly Ala Asp Gly
450                 455                 460

Ala Thr Ala Tyr Asp Asp Ser Val Asn Gln His Thr Ala Thr Val Thr
465                 470                 475                 480

Gly Ala Thr Phe Ile Asp Asp Val Thr Arg Glu Lys Val Ala Ser Phe
                485                 490                 495

Thr Glu Thr Asp Leu Ile Thr Leu Asn Asn Phe Thr Gly Ile Leu Gly
                500                 505                 510

Glu Ser Ala Arg Thr Thr Met Ala Trp Ile Lys Thr Ser Asp Ser Asn
        515                 520                 525

Ala Asp Val Ile Gln Trp Gly Lys Gln Glu Thr Ser Glu Ala Trp Tyr
530                 535                 540

Val Gly Leu Asp Asn Gly Ile Leu Gln Leu Asn Ile Gln Gly Ser Thr
545                 550                 555                 560

Val Ile Gly Ala Ser Val Leu Asn Asp Asp Ser Trp His His Ile Ala
                565                 570                 575

Val Ile Ala Pro Asp Asn Ser Ile Ala Asn Thr Gln Val Tyr Ile Asp
                580                 585                 590

Gly Val Leu Glu Thr Leu Thr Val Asn Asp Gly Gly Ser Ser Thr Phe
        595                 600                 605

Asn Thr Val Ala Asp Thr Asn Val Val Ile Gly Gly Glu Phe Thr Gly
610                 615                 620

Leu Ile Asp Lys Thr Val Val Tyr Asn Arg Ala Leu Glu Glu Ser Glu
625                 630                 635                 640

Ile Asp Tyr Ile Val Asn Ser Ala Asp Ala Asp Ile Asp Leu Gly Ile
                645                 650                 655

Ser Leu Asp Val Arg Phe Asp Glu Asp Ala Asn Ala Thr Thr Val Ala
                660                 665                 670

Asp Asn Ser Ala Tyr Glu Arg Ser Gly Ile Asn Arg Gly Ala Ile Thr
        675                 680                 685
```

```
Gly Val Phe Asp Ala Thr Arg Asn Ser Asn Val Tyr Ser Leu Asp Gly
    690                 695                 700
Val Asp Ser Gly Glu Asp Leu Asp Asp Leu Ile Asp Ser Asp Tyr Glu
705                 710                 715                 720
His Gln Ile Val Met Thr Thr Asn Asn Lys Arg Asp Asn Lys Gly Tyr
                725                 730                 735
Ser Gly Val Asn Gly Gly Asp Pro Arg Thr Val Met Ala Trp Ile Lys
            740                 745                 750
Thr Thr Phe Gly Gly Ala Val Ile Ala Gln Trp Gly Asn Lys Asp Ser
        755                 760                 765
Val Asp Gly Glu Gln Tyr Glu Val Arg Leu Lys Asn Gly Glu Leu Arg
770                 775                 780
Val Asp Ile Thr Gly Gly Leu Ile Lys Gly Thr Thr Leu Ile Asn Asp
785                 790                 795                 800
Gly Glu Trp His His Ile Ala Val Val Ser Pro Asp Asp Gln Leu Ala
                805                 810                 815
Asn Thr Lys Leu Tyr Val Asp Gly Val Leu Glu Thr Thr Thr Thr Ser
            820                 825                 830
Gly Ser Gln Thr Thr Ile Asp Thr Leu Thr Leu Asn Gly Asp Ser Lys
        835                 840                 845
Asp Val Ile Ile Gly Ser Thr Phe Val Gly Glu Met Asp Asn Phe Val
850                 855                 860
Ile His Gln Arg Ala Leu Lys Gln Phe Glu Val Lys Val Ala Ala Gly
865                 870                 875                 880
Ile

<210> SEQ ID NO 3
<211> LENGTH: 697
<212> TYPE: PRT
<213> ORGANISM: Bacteria

<400> SEQUENCE: 3

Met Ile Lys Lys Tyr Asn Leu Ile Lys Thr Gly Val Ile Thr Phe Leu
1               5                   10                  15
Val Leu Phe Phe Gln Gln Thr Tyr Ala Gln Thr Thr Thr Val Tyr Ser
            20                  25                  30
Leu Glu Asp Leu Leu Pro Tyr Leu Lys Gln Asp Asn Val Asp Val Lys
        35                  40                  45
Leu Ala Pro Gly Thr Tyr Asn Val Asn Gly Phe Asp Val Gly Glu Asp
    50                  55                  60
Arg Leu Phe Ser Thr Thr Pro Leu Phe Leu Phe Glu Gly Ser Asn Ser
65                  70                  75                  80
Thr Tyr Asp Phe Thr Asp Val Lys Leu Asn Ile Asn Thr Val Val Leu
                85                  90                  95
Thr Lys Phe Gly Asn Asn Glu Val Asn Glu Ile Gln Ile Leu Gly Asn
            100                 105                 110
Asn Asn Val Leu Lys Asn Leu Lys Leu Glu Asp Ile Gly Thr Thr Ala
        115                 120                 125
Pro Ser Asn Arg Ala Gln Ser Ile Val Ile Asp Gly Arg Asp Asn Arg
    130                 135                 140
Ile Glu Gly Phe His Leu Thr Ile Arg Gly Ser Tyr Pro Tyr Gly Tyr
145                 150                 155                 160
```

```
Gly Asp Ala Phe Gly Lys Gly Gly Ser Val Ile Asn His Arg Lys
            165                 170                 175

His Ser Gly Val Leu Ile Arg Gly Leu Arg Asn His Leu Lys Asp Cys
            180                 185                 190

Thr Ile Ile Ser Arg Ser Tyr Gly His Ile Val Phe Met Gln Ala Ala
            195                 200                 205

Ser Tyr Pro Thr Val Glu Gly Cys Tyr Ile Glu Gly Glu Met Arg Ser
            210                 215                 220

Thr Asp Asp Met Leu Ala Glu Glu Gly Thr Gly Ser Pro Ala Asp Lys
225                 230                 235                 240

Val Asp Phe Met Thr Val Trp Gly Tyr Lys Leu Pro Ala Gly Tyr Met
            245                 250                 255

Met Ser Leu Gln Glu Gly Gly Ile Arg Ala Tyr Asn Ala Gly Thr Thr
            260                 265                 270

Tyr Ile Asp Gly Val Glu Ile Gln Arg Ala Thr Asp Asn Pro Thr Val
            275                 280                 285

Leu Asn Cys Thr Ile Lys Asn Ala Arg Thr Gly Val Thr Leu Ala His
            290                 295                 300

Ala Asn Gly Thr Lys Tyr Val Glu Gly Cys Thr Val Leu Gly Cys Glu
305                 310                 315                 320

Asn Gly Tyr Ser Ile Gly Ser Gly Thr Val Asn Cys Gly Ala Asp
            325                 330                 335

Ala Ile Tyr Gly Pro Val Phe Lys Asn Thr Tyr Gly Ser Asp Lys Gly
            340                 345                 350

Tyr Asn Ala Asp Ile Thr Ile Leu Pro Pro Ser Asp Ala Tyr Tyr Asn
            355                 360                 365

Gly His Asp Ala Val Ala Tyr Ile Gly Gly Ser Asn His Asn Leu Thr
            370                 375                 380

Phe Arg Ser Glu Ile Thr Glu Ile Pro Ser Asn Leu Lys Ile Met Val
385                 390                 395                 400

Ser Gly Asp Leu Gln Gly Leu Arg Val Leu His Gly Ser Asn Pro Ser
            405                 410                 415

Gln Asn Asn Phe Ala Gly Thr Asn Ile Val Leu Arg Asn Leu Thr Asn
            420                 425                 430

Phe Pro Val Asp Leu His Ser Asp Ser Ser Asn Ile Thr Val Thr Ser
            435                 440                 445

Cys Asp Thr Asp Asn Ile Thr Asp Asn Gly Thr Asn Asn Ser Ile Glu
            450                 455                 460

Ala Ile Asp Cys Asp Ser Asp Asn Leu Ala Leu Lys Gly Glu Ala Ser
465                 470                 475                 480

Gln Ser Ser Ser Arg Pro Ser Asp Gly Phe Ala Ala Asn Ala Ile Asp
            485                 490                 495

Gly Asn Thr Asn Gly Ala Trp Ser Asn Asn Ser Val Ser His Thr Gly
            500                 505                 510

Thr Glu Glu Asn Pro Trp Trp Gln Val Asp Leu Gly Thr Asp Ala Ile
            515                 520                 525

Ile Gly Ser Ile Asn Ile Phe Asn Arg Thr Asp Gly Cys Cys Lys Gly
            530                 535                 540
```

-continued

Arg Leu Asp Asn Phe Thr Val Tyr Val Ile Asp Lys Asp Asp Lys Val
545                 550                 555                 560

Thr Phe Ser Lys Thr Tyr Val Thr Val Pro Asp Pro Ser Ile Thr Val
                565                 570                 575

Asp Ala Gly Gly Val Asn Gly Lys Ile Val Lys Ile Val Leu Asn Asn
            580                 585                 590

Ser Ser Gln Ala Leu Ala Leu Ala Glu Val Glu Val Tyr Gly Thr Ser
            595                 600                 605

Leu Ser Asn Lys Glu Thr Ile Lys Asn Pro Ile His Phe Tyr Pro Asn
    610                 615                 620

Pro Val Glu Asp Glu Val Thr Ile Ser Leu Glu Ser Ala Asp Leu Asn
625                 630                 635                 640

Leu Asn Glu Thr Arg Val Val Ile Tyr Asn Ile Lys Gly Gln Lys Ile
                645                 650                 655

Leu Glu Thr Thr Pro Ser Asn Ser Thr Glu Val Asn Leu Asn Leu Ser
            660                 665                 670

His Leu Pro Thr Gly Val Tyr Leu Ile Arg Val Ser Asp Gln Asn Lys
            675                 680                 685

Asn Ile Ile Asn Lys Ile Val Lys Leu
    690                 695

<210> SEQ ID NO 4
<211> LENGTH: 704
<212> TYPE: PRT
<213> ORGANISM: Bacteria

<400> SEQUENCE: 4

Met Lys Lys Tyr Ser Ile Leu Lys Ile Gly Ile Ile Ala Val Ile Met
1               5                   10                  15

Leu Phe Val Gln Gln Ser Tyr Ala Gln Thr Thr Thr Val Tyr Ser Leu
                20                  25                  30

Glu Asp Leu Leu Pro Tyr Leu Lys Gln Asp Asn Val Asp Val Lys Leu
            35                  40                  45

Ala Pro Gly Thr Tyr Asn Ile Asn Ala Phe Asp Ile Thr Gln Gly Lys
    50                  55                  60

Phe Ser Asn Pro Leu Phe Leu Phe Glu Gly Ser Asn Asn Thr Phe Asp
65                  70                  75                  80

Phe Thr Asp Val Lys Ile Asn Ile Asn Thr Leu Val Leu Thr Lys Phe
                85                  90                  95

Gly Asn Asn Glu Val Asn Glu Ile Gln Ile Leu Gly Asn Asn Asn Val
                100                 105                 110

Leu Lys Asn Leu Lys Leu Glu Asp Ile Gly Thr Thr Ala Pro Ser Asn
    115                 120                 125

Arg Ala Gln Ser Ile Ile Met Asp Gly Arg Asp Asn Arg Ile Glu Gly
    130                 135                 140

Phe His Leu Thr Ile Arg Gly Ser Tyr Pro Tyr Gly Tyr Gly Asp Ala
145                 150                 155                 160

Pro Gly Lys Gly Gly Ser Val Ile Asn His Arg Lys His Ser Gly
                165                 170                 175

Val Leu Ile Arg Gly Leu Arg Asn His Leu Lys Asp Cys Thr Ile Ile
            180                 185                 190

-continued

```
Ser Arg Ser Tyr Gly His Ile Val Phe Met Gln Ala Ala Ser Tyr Pro
        195                 200                 205
Thr Val Glu Gly Cys Tyr Ile Glu Gly Glu Met Arg Ser Thr Asp Asp
210                 215                 220
Met Leu Ala Glu Gly Thr Gly Ser Pro Ala Asp Asn Val Asp Phe
225                 230                 235                 240
Met Thr Val Trp Gly Tyr Lys Leu Pro Ala Gly Tyr Met Met Ser Leu
                245                 250                 255
Gln Glu Gly Gly Ile Arg Ala Tyr Asp Ala Gly Thr Thr Tyr Ile Asp
        260                 265                 270
Gly Glu Val Ile Gln Arg Ala Thr Asp Asn Pro Thr Val Leu Asn Cys
        275                 280                 285
Thr Ile Lys Asn Ala Arg Thr Gly Val Thr Leu Ala His Ala Lys Gly
        290                 295                 300
Thr Lys His Val Glu Asn Val Lys Ala Ile Gly Cys Glu Gly Gly Tyr
305                 310                 315                 320
Ser Ile Gly Ser Gly Thr Val Ser Asn Cys Ser Gly Asp Ala Gln Tyr
                325                 330                 335
Gly Pro Leu Leu Ser Phe Ala Tyr Ser Ser Asp Lys Asn Thr Asn Ile
                340                 345                 350
Asp Ile Glu Val Leu Pro Ala Glu Asn Tyr Tyr Asn Gly Ser Glu Thr
        355                 360                 365
Ala Ala Tyr Val Gly Gly His Ser His Asn Ile Thr Leu Arg Gly Gly
        370                 375                 380
Asp Pro Asn Ala Asp Leu Arg Val Gln Val Gly Gly Glu Lys Asn Asn
385                 390                 395                 400
Val Arg Leu Leu Gly Val Thr Ser Asn Gln Asn Pro Leu Ser Ala Ser
                405                 410                 415
Asn Leu Glu Leu Asn Asn Leu Thr Asn Phe Pro Val Val Leu Asp Glu
                420                 425                 430
Met Ser Ser Asn Ile Ile Val Glu Ser Cys Gly Glu Val Thr Asn Asn
        435                 440                 445
Gly Ser Asn Asn Ser Ile Thr Asp Cys Pro Asp Gly Pro Ile Ser Phe
        450                 455                 460
Pro Asp Ser Ser Lys Ala Tyr Arg Leu Gly Asn Asn Arg Phe Thr Phe
465                 470                 475                 480
Trp Val Ala Ala Asn Gly Gly Asp His Ala Tyr Ser Ile Lys Tyr Asn
                485                 490                 495
Asp Gly Ile Ser Gly Asn Ile Asn Asp Tyr Glu Asp Leu Phe Pro Glu
                500                 505                 510
Gly Glu Glu Ser Phe Trp Val Phe Thr Pro Val Glu Gly Arg Asp Gly
                515                 520                 525
Tyr Phe Phe Val Asp Cys Val Gly Gly Asp Lys Gln Arg Leu Ser
        530                 535                 540
Ala Thr Thr Asp Ser Gly Leu Pro Val Met Val Ser Lys Thr Ile Thr
545                 550                 555                 560
Ser Ala Ser Val Gln Trp Ser Val Val Gln Pro Glu Gly Arg Asp Thr
                565                 570                 575
```

```
Phe His Ile Thr Asn Asp Tyr Ala Arg Met Val Gly Ala Asn Thr Thr
            580                 585                 590

Thr Asn Gln Thr Ile Leu Ser Thr Val Gly Asn Thr Ser Asn Gln Ser
            595                 600                 605

Arg Phe Glu Val Leu Glu Val Ser Asn Tyr Ser Leu Ser Ile Lys Asn
            610                 615                 620

Asp Ile Leu Asn Asn Asn Ile Thr Val Phe Pro Ile Pro Thr Ser Asp
625                 630                 635                 640

Ile Leu Asn Ile Asn Leu Lys Asn Met Glu Ser Val Thr Val Glu Leu
            645                 650                 655

Tyr Asn Ser Ile Gly Gln Lys Ile Leu Ser Lys Glu Ile Lys Gln Gly
            660                 665                 670

Glu Asn Thr Leu Asn Leu Ser Gly Ile Tyr Thr Gly Val Tyr Leu Leu
            675                 680                 685

Lys Leu Asn Asp Gly Gln Asn Ser Tyr Thr Lys Arg Ile Ile Met Lys
            690                 695                 700

<210> SEQ ID NO 5
<211> LENGTH: 2442
<212> TYPE: DNA
<213> ORGANISM: Bacteria

<400> SEQUENCE: 5
atgaaaatac gtaatgtttg tcgtagtgcg gtgcttttag cttgatgct tttaaataca      60 tacgcagaaa caaagctga ttggatgcaa ggtaactggg ggatcagtta tcgaatacct     120
ggaggagata ttaattactc aggtagtcat gttgcagaat acaatgtaag agccgcagtt     180
gaacaaatct cagcaattcc tggtttgaag tgggtacaaa ttaatttaac caacggtgca     240
tctggtgatc gttttatagt ccctgtaaca gaagttgaag ccattaatcc tttatccgct     300
cctaacagta ttaatgactt atacgatcct actttacctg gcgagatct ttttgagcaa     360 ctggcattag ccttcaaagc taaggcata agagttgttg cttatattgc gactcaaggg     420
cctggcatgc tcaagcatgg tgctgaaaac tcgatggatg aagatgactc cattactgac     480
tgtaaatcgt ctaagccatt agtaaccgat cttgatacac aagtttactg ttcagcaaat     540
atgaatcgct ggagagatta cgttttagaa caatacccat caaccagtct ttatagaagt     600
tttgaattgg caatggtcaa tattgtagaa acattatcac tgcgttatgg aagtacaatt     660
gatggctggt ggtttgatca ttcaggtttt ggtgacagtg aattacttca tgctgcggct     720
ctagctggaa ataatgatgc ggcagtagcc tttaatgaag gcgataaagt tcctttggta     780
aataacccag agacattaga cgattacacc tttggtcatc aacacctat aggtagtgag     840 gtttcttctg atgataaaaa cctacctatg ttaacgtcta tagaagctac tttagatggt     900
attttaactg gttcaggtga tgatgtaggc tctgtgggac atatgtttat gccacttcaa     960
gaaagttgga atggtggcac tgttgtattt tctgaagcga aaggatctga ctggcttaat    1020
cgagcattaa aagccggagg tgcatttaca tgggcactaa gccaagacag taatgatgag    1080
ttaggtggtg gcggagcaag attaatttca gaaccgcagg taaaaatgct tgaacgtatg    1140
agttttaata taggtaaaca attacatatg aatctagatg gttcagatgg tgatactgct    1200
tatgatgact ccgtcaacca atataccgct actgtaaacg gtgctaattt tgttgatgat    1260
```

-continued

```
gttacaagag gaaaagttgc aagtttact gaagacgacc agttagaact agacaattat      1320
caaggtattt caggtggaaa tgcgcgtaca accatggctt ggataaaaac ttcagacagc      1380
aaaggcgata ttattgattg ggtaataac acaacaagcg aacgttggtg gttacgttta      1440
gttgacggta aatttaaact gatattaaaa ggtcctaatc ttacaggaac tacaacactt      1500
aatgacgacc aatggcacca tattgctgtt gtagcttctg ataacgtagt tgctaatatc      1560
aaagtataca ttgatggtgt tttagaaact gttgctgtaa atgacaatgc ttcaactacc      1620
ttcgatacaa ccttaggtgg caatatacaa ataggtgggg cctacaccgg acttatcgat      1680
aaagtgcttg tgcatgatag agcattagat gaaagcgaga ttgagtatgt tgttaattca      1740
tccaatgctg atcttgattt agaggttgca ttagatgtgc gttttgaaga gtcagcaaac      1800
tcaactaaag taaccgataa ttctatatat ggacgtcatg gcacaaatcg aggtgctatt      1860
actggcgtgt tgatgcaga acgtaacagc aatgtgtact cacttgatgg tgttgatagt      1920
ggcgaagata taaatgattt aaaagatagc gactacgaac atgaagtrgt aatgacaaca      1980
gataattcta aagactcaaa aggttatagt ggagttaatg gtgcaggtcc gcgtactgta      2040
atggcatgga taaaaacaac ttttggcggt gctgttattg cccaatgggg taataaaaat      2100
tcagttgatg cgaacaata tgaagttcgt taaaaaatg gtgcactgag attagatatt      2160
acaggtggca ttattaaagg cacaacatca attaatgatg gcgagtggca tcatattgct      2220
gtggtttcac ctgatgaaca gttagctaat actaaattgt atgttgatgg tgtactagaa      2280
acagcaacca cttcgggttc tcaagcaacg attgatacta aaactcttaa tggcgatagc      2340
aaagacgtaa taattggtag tacgtttgtt ggcgagatgg acgattttat tattcatcaa      2400
cgcgctttaa gacagtttga agtgaaaaac tcagcaggac tc                        2442
```

<210> SEQ ID NO 6
<211> LENGTH: 2643
<212> TYPE: DNA
<213> ORGANISM: Bacteria

<400> SEQUENCE: 6

```
atgaaaatac gtaatatgtg ttgtactgct ttaatcgtaa gtttaatggg ctgcggtggt        60
tctggttcag aagctagttc tcctgaagta aagttgata atggagtaga aattcaacct       120
gaaccagaag ttgaacctga gccagaagtt gaacctgaac agaagttgaa acctgaacca       180
gaagttgaac ctgaaccaga agttgaacct gagccagaag ttgagcctga accagaagtt       240
gaacctgaac cagaagatat aagagcctca tggatgcaag gtaactgggg aatcagcttc       300
agaatttctg gtggtgacat cagtcaaaat gaaagtcatg taatgaata ccaagtagca       360 ccagctgttg agcaaatagc cgcaattcct ggattaaagt ggttacaagt taatttaagt       420
aacggggctt ttggcgaccg ttttattgta cctgtacctg aagtagaagc tattaatcca       480
aattcagcgc caaacagctc ggcagattta tttgatcctg cattacctgg cgatgactta       540
tttgaacaaa tagcactagg acttcaagcc aaaggcataa agtagtagc atatattgcg       600 actcaaggtc ctgcaatgct gaaacatggc gcagaaagat cgatggattt tgatgattct       660
attgttgatg aatcagatgg cagtgcttgt aaatcttcaa gacctgtcgt ttctgatcct       720
gatacgcaag tttattgttc agcaaatatg aatcgctgga gagattatgt gttacagcaa       780
tacccatcaa caagtttgca tcatagtttt caattgggac tcgtcaatat tgtagaaact       840
ttatcactac gttacggcac tctgattgat ggttggtggt ttgatcattc tatttacggt       900
gactacaact tacttcctga tgctgcaaga gcgggaaata gcaatgctgc ggtttctctt       960
```

-continued

```
aatttagaag gggatatttt cttaagtaat aacccagaag tgatggagga ttttaccggc      1020
ggacatccaa caccgattgc tcgagttgtt tcatctgatg ataccaattt acccatgtta      1080
acggctatag aagatgctcc aaacggtatt tttacaggaa caggtgatga tgtagatgct      1140
ttagggcaca tgtttttacc gctgcaagaa acctggaatg gcggaactgt agtattttca      1200
gaagccaaag gaactgagtg gcttaacaga gttactcgag ctggcggcgc attaacttgg      1260
gcattaagcc atgaaggcag tgtttctggt ggtgaggcta tgttgatttc tgcaccacaa      1320
gcaaaaatgc ttgcacgtat gcagctaaat attggtaaac aactcgatat ggatttagat      1380
ggtgccgatg gcgctacggc ttatgatgat tctgtcaatc aacatacagc tacggttaca      1440
ggtgcgacat ttatagatga tgttactcgt gaaaaagtgg caagctttac tgaaacagat      1500
ctgattacgt taaacaattt tactggtatt ttaggcgaaa gtgctcgtac aacaatggct      1560
tggataaaaa catcagacag taacgcagat gttattcaat ggggtaaaca agagacgagt      1620
gaagcttggt atgtgggctt agacaatgga atacttcaat taaatattca aggttctacg      1680
gttattggcg caagtgtact taacgatgat agttggcatc atattgctgt tatcgcgcct      1740
gataattcaa ttgccaatac tcaagtctat atcgatggtg ttttagaaac acttaccgtg      1800
aatgatggtg ttcatctac atttaataca gtggcagaca ccaacgttgt aataggagga      1860
gagtttactg gccttataga taaaaccgtt gtgtataaca gagcattaga agaaagcgag      1920
attgattata ttgttaattc agctgacgca gatattgatt taggtatttc acttgatgtg      1980
aggtttgatg aagatgctaa tgcaacaaca gtagctgata attctgccta tgaacgttca      2040
ggtataaatc gaggtgccat tacgggcgtt tttgatgcaa cacgtaacag caatgtttat      2100
tcacttgatg gtgttgatag cggcgaagat ctagatgatt aatagatag tgattatgag      2160 catcaaattg ttatgacaac caataacaaa agagataaca aaggttatag tggcgtgaat      2220
ggcggtgatc ctcgaactgt tatggcatgg ataaaaacaa cctttggtgg tgctgttatt      2280
gctcaatggg gtaataaaga ttcagtcgat ggcgaacaat atgaagtgcg cttgaaaaat      2340
ggcgaactta gagtcgatat cactggcggg cttattaaag gaacaacatt aataaacgat      2400
ggcgaatggc atcatattgc tgttgtatct cctgatgatc aattagctaa cactaaactt      2460
tatgttgatg gtgttctaga acgaccacc acctccggct ctcaaacaac aatagatacg      2520
ttaaccctta acggtgacag caaagacgta atcattggaa gtacttttgt tggcgagatg      2580
gataactttg ttattcatca acgtgcttta aaacaatttg aagtaaaagt cgccgcaggt      2640
att                                                                   2643
```

<210> SEQ ID NO 7
<211> LENGTH: 2091
<212> TYPE: DNA
<213> ORGANISM: Bacteria

<400> SEQUENCE: 7

```
atgataaaaa aatacaattt aattaaaaca ggagttatta catttctagt tttgtttttt        60
cagcaaactt acgcacaaac aaccacagta tattctttag aagacttact accctattta       120
aaacaggata atgtagatgt taaattagcc ccaggaactt ataatgttaa tggttttgat       180
gtaggtgaag acaggttgtt ttccactact ccacttttt tgtttgaagg gtctaacagt       240
acttatgact ttacagatgt aaagcttaac atcaatacgg ttgtgttaac caagtttgga       300
aataatgagg ttaatgaaat tcagatttta ggaaataaca atgttcttaa aaacttaaaa       360
ctagaagata ttggaacaac agctccttct aacagagctc agtctattgt tatagatggg       420
```

-continued

| | |
|---|---|
| cgagacaata gaatagaagg ttttcattta accattagag gatcttaccc ttatggatat | 480 |
| ggagatgctt ttggaaaagg aggaggttcc gtaattaatc accgaaaaca ttcaggtgtt | 540 |
| ttaataagag gattacgtaa tcacctaaaa gattgtacca ttatttctcg ttcttatggg | 600 |
| catatagtat tcatgcaagc agcaagttac ccaactgtgg aaggttgtta tattgaaggt | 660 |
| gaaatgcgtt caaccgatga tatgttggca gaagaaggaa caggttctcc agcagataaa | 720 |
| gtagatttta tgacggtttg gggatataag ttaccagctg gttatatgat gagtttacaa | 780 |
| gaaggaggaa ttagagcata taatgcagga accacttata ttgatggagt agagattcaa | 840 |
| cgagcaacag acaaccctac cgttctaaat tgtactatta aaaatgcaag aacaggagta | 900 |
| acattagcac atgcaaatgg aacaaaatat gttgagggtt gtactgtttt aggatgtgaa | 960 |
| aatggatact ccataggaag tggaactgta gtaaactgtg gagcagatgc tatttatgga | 1020 |
| cctgtattta aaaatacata cggaagcgat aaagggtaca atgcagacat taccattttg | 1080 |
| ccacctagtg atgcttacta caacggacat gatgctgtag catacattgg aggatcaaat | 1140 |
| cataacctta cttttagaag tgaaataaca gaaattccaa gcaatttaaa aattatggtc | 1200 |
| tctggagatt tacaaggatt aagagtattg catggaagta atcctagtca gaataatttt | 1260 |
| gctggaacca acattgtttt aagaaattta acaaactttc ctgtagactt acattcagac | 1320 |
| agttctaata taactgttac ttcttgtgat acggataata ttacagacaa tggtacaaat | 1380 |
| aatagtattg aagctataga ttgcgattcg gataatttag ctttaaaagg agaagctagt | 1440 |
| caatcatcct ctcgtccaag tgatggtttt gcagcaaatg ccattgatgg aaatacaaat | 1500 |
| ggggcatggt caaacaattc tgtttctcat acgggtacag aagaaaatcc atggtggcaa | 1560 |
| gtagatttag gaacagatgc tattataggt agcatcaata ttttttaacag aacagatggt | 1620 |
| tgttgtaaag gtagattaga taattttact gtttacgtga tagataaaga tgataaggtt | 1680 |
| acattttcta aaacctatgt taccgttcca gatccgtcta taactgttga tgcaggtggt | 1740 |
| gtgaatggaa aaattgtaaa aattgttttg aataacagtt cacaggcttt ggctttagca | 1800 |
| gaggtagaag tgtacggaac gtctttgtct aataaagaaa ctataaagaa tcctattcat | 1860 |
| ttttatccta acccggtaga agatgaggta actatttctt tagagtcagc cgatttaaat | 1920 |
| ttaaacgaga ctcgagttgt tatttataat ataaaaggtc aaaaaatact agaaacaact | 1980 |
| ccaagtaatt ccacggaagt taatttaaac ttatctcact taccaacagg agtttattta | 2040 |
| ataagagtaa gcgatcaaaa taaaaatatc ataaataaaa ttgtaaaatt a | 2091 |

<210> SEQ ID NO 8
<211> LENGTH: 2112
<212> TYPE: DNA
<213> ORGANISM: Bacteria

<400> SEQUENCE: 8

| | |
|---|---|
| atgaaaaaat atrctatcct aaaaatagga attatagctg ttataatgtt gtttgttcag | 60 |
| cagtcttacg cacaaacaac cacagtatat tctttagaag acttactacc ctatttaaaa | 120 |
| caggataatg tagatgttaa attagcccca ggaacttata atatcaatgc atttgacatt | 180 |
| actcaaggaa aattttcgaa ccccttattt ctttttgaag ggtctaataa tacttttgat | 240 |
| tttacagatg ttaaaataaa catcaatact ctggtgttaa caaagtttgg gaataatgaa | 300 |
| gtcaatgaaa ttcagatttt aggaaataac aatgttctta aaaacttaaa actagaagat | 360 |

-continued

```
attggaacaa cagctccttc taacagagcc cagtcaatta taatggatgg gcgagacaat    420
agaatagaag gctttcattt aaccattaga ggatcttatc cttatggata tggagatgct    480
tttgaaaaag gaggaggttc cgtaattaat caccgaaaac attcaggtgt tttaataaga    540
ggattacgta atcacctaaa agattgtact attatttctc gttcttatgg gcatatagta    600
tttatgcaag cagcaagtta cccaactgta gaaggttgtt atattgaagg tgaaatgcgt    660
tcaaccgatg atatgttggc agaagaagga acaggttctc cagcggataa tgtagatttt    720
atgacggttt ggggatataa gttaccagct ggttatatga tgagtttaca agaaggagga    780
attagagctt atgatgctgg taccacttat attgatggag aagtaatcca agagcaaca    840
gataacccta ccgttctaaa ttgtaccatt aaaaatgcaa gaacaggagt gactttagca    900
catgctaaag gaacaaaaca cgtagaaaat gttaaggcta ttgggtgtga gcaaggatat    960
tcaattggta gtggtacagt gagtaattgt agtggtgatg ctcagtatgg tccgttgtta   1020
agttttgctt attctagtga taaaaatacg aatatagaca tagaagtttt gcctgcagaa   1080
aattattata acggtagtga aactgctgct tacgttggag gacattctca taatattaca   1140
ctaagaggag gtgatcctaa tgcggatctt agagttcagg taggggagaa aaaaaataac   1200
gttaggttgc ttggagttac ttctaatcaa aatccacttt ctgcttcaaa tttggaactg   1260
aataatttaa ctaattttcc tgtagtgtta gatgaaatga gttctaatat tattgtggag   1320
tcatgtgggg aggttaccaa taacggaagt aataatagta ttactgactg cccagatgga   1380
ccaattagct ttccagattc aagcaaagcg tatcgtttag gaataatag atttacattt     1440
tgggttgcgg ccaatggagg agatcatgct tattctataa agtataatga tggtattagt   1500
ggtaacatta atgattatga ggatttgttt ccagaaggag aagagtcttt ttgggttttt   1560
actccagtag agggaagaga cggatacttt tttgttgatt gtgttggtgg tggtgataaa   1620
caaagattgt cagctactac agatagtggc ttgccagtaa tggtgtcaaa aaccattaca   1680
agtgcatctg ttcaatggtc tgtagtgcaa ccagaaggaa gagatacttt ccatataacg   1740
aatgattatg ctagaatggt aggagctaat acaactacta atcaaaccat tttgtctact   1800
gttgggaaca cctcaaacca atctcgtttt gaagttcttg aagtttctaa ctattcttta   1860
agtattaaaa acgacatctt aaacaataat attacggttt ttcctattcc aacatctgac   1920
attcttaata taaatttaaa aaatatggag tctgttactg ttgaattata caactcaata   1980
ggtcaaaaaa tattatcaaa agaaattaaa caaggtgaaa ataccctaaa cttgtctggt   2040
atttatacag gagtttattt gttaaaattg aacgatggac aaaattctta tacaaaagaa   2100
attattatga aa                                                       2112
```

<210> SEQ ID NO 9
<211> LENGTH: 7
<212> TYPE: PRT
<213> ORGANISM: Bacteria

<400> SEQUENCE: 9

Thr Thr Met Ala Trp Ile Lys
 1               5

<210> SEQ ID NO 10
<211> LENGTH: 18
<212> TYPE: PRT
<213> ORGANISM: Bacteria

```
<400> SEQUENCE: 10

Gly Thr Thr Ser Ile Asn Asp Gly Glu Glu His His His Ala Val Val
 1               5                  10                  15

Ser Pro

<210> SEQ ID NO 11
<211> LENGTH: 15
<212> TYPE: PRT
<213> ORGANISM: Bacteria
<220> FEATURE:
<221> NAME/KEY: VARIANT
<222> LOCATION: (1)...(15)
<223> OTHER INFORMATION: Xaa = Any Amino Acid

<400> SEQUENCE: 11

Gly Pro Asn Leu Thr Gly Thr Thr Thr Leu Asn Asp Xaa Gln Thr
 1               5                  10                  15

<210> SEQ ID NO 12
<211> LENGTH: 24
<212> TYPE: PRT
<213> ORGANISM: Bacteria
<220> FEATURE:
<221> NAME/KEY: VARIANT
<222> LOCATION: (1)...(24)
<223> OTHER INFORMATION: Xaa = Any Amino Acid

<400> SEQUENCE: 12

Ala Asp Ile Met Xaa Gly Xaa Xaa Gly Ile Ser Tyr Arg Ile Pro Gly
 1               5                  10                  15

Xaa Asp Ile Asn Tyr Ser Gly Ser
            20

<210> SEQ ID NO 13
<211> LENGTH: 17
<212> TYPE: DNA
<213> ORGANISM: Bacteria
<220> FEATURE:
<221> NAME/KEY: misc_feature
<222> LOCATION: (1)...(17)
<223> OTHER INFORMATION: n = A,T,C or G

<400> SEQUENCE: 13
acnatggcnt ggathaa                                                17

<210> SEQ ID NO 14
<211> LENGTH: 15
<212> TYPE: DNA
<213> ORGANISM: Bacteria

<400> SEQUENCE: 14
catgaaaata cgtag                                                  15

<210> SEQ ID NO 15
<211> LENGTH: 15
<212> TYPE: DNA
<213> ORGANISM: Bacteria

<400> SEQUENCE: 15
gatcctacgt atttt                                                  15

<210> SEQ ID NO 16
<211> LENGTH: 30
<212> TYPE: PRT
<213> ORGANISM: Bacteria
```

```
<220> FEATURE:
<221> NAME/KEY: VARIANT
<222> LOCATION: (1)...(30)
<223> OTHER INFORMATION: Xaa = Any Amino Acid

<400> SEQUENCE: 16

Xaa Pro Ala Gly Tyr Met Met Ser Leu Gln Glu Gly Gly Ile Arg Ala
 1               5                  10                  15

Tyr Asn Ala Gly Thr Thr Tyr Ile Xaa Gly Val Glu Ile Gln
            20                  25                  30

<210> SEQ ID NO 17
<211> LENGTH: 22
<212> TYPE: PRT
<213> ORGANISM: Bacteria

<400> SEQUENCE: 17

Gly Glu Ala Ser Gln Ser Ser Ser Arg Pro Ser Asp Gly Phe Ala Ala
 1               5                  10                  15

Asn Ala Ile Asp Gly Asn
            20

<210> SEQ ID NO 18
<211> LENGTH: 19
<212> TYPE: PRT
<213> ORGANISM: Bacteria
<220> FEATURE:
<221> NAME/KEY: VARIANT
<222> LOCATION: (1)...(19)
<223> OTHER INFORMATION: Xaa = Any Amino Acid

<400> SEQUENCE: 18

Xaa Tyr Val Thr Val Pro Asp Pro Ser Ile Thr Val Asp Ala Gly Gly
 1               5                  10                  15

Val Asn Gly

<210> SEQ ID NO 19
<211> LENGTH: 18
<212> TYPE: PRT
<213> ORGANISM: Bacteria

<400> SEQUENCE: 19

Phe Gly Asn Asn Glu Val Asn Glu Ile Gln Ile Leu Gly Asn Asn
 1               5                  10                  15

Val Leu

<210> SEQ ID NO 20
<211> LENGTH: 17
<212> TYPE: PRT
<213> ORGANISM: Bacteria
<220> FEATURE:
<221> NAME/KEY: VARIANT
<222> LOCATION: (1)...(17)
<223> OTHER INFORMATION: Xaa = Any Amino Acid

<400> SEQUENCE: 20

Tyr Val Glu Gly Cys Thr Val Leu Gly Cys Xaa Xaa Gly Tyr Ser Ile
 1               5                  10                  15

Gly
```

<210> SEQ ID NO 21
<211> LENGTH: 17
<212> TYPE: DNA
<213> ORGANISM: Bacteria
<220> FEATURE:
<221> NAME/KEY: misc_feature
<222> LOCATION: (1)...(17)
<223> OTHER INFORMATION: n = A,T,C or G

<400> SEQUENCE: 21
ttyggnaaya aygargt                                                       17

<210> SEQ ID NO 22
<211> LENGTH: 26
<212> TYPE: DNA
<213> ORGANISM: Bacteria
<220> FEATURE:
<221> NAME/KEY: misc_feature
<222> LOCATION: (1)...(26)
<223> OTHER INFORMATION: n = A,T,C or G

<400> SEQUENCE: 22
aayaaygarg tnaaygarat hcarat                                             26

<210> SEQ ID NO 23
<211> LENGTH: 675
<212> TYPE: DNA
<213> ORGANISM: Bacteria

<400> SEQUENCE: 23
aataatgagg ttaatgaaat tcagatttta ggaaataaca atgttcttaa aaacttaaaa         60
ctagaagata ttggaacaac agctccttct aacagagccc agtcaattat aatggatggg        120
cgagacaata gaatagaagg ctttcattta accattagag gatcttatcc ttatggatat        180
ggagatgctt ttggaaaagg aggaggttcc gtaattaatc accgaaaaca ttcaggtgtt        240
ttaataagag gattacgtaa tcacctaaaa gattgtacta ttatttctcg ttcttatggg        300
catatagtat ttatgcaagc agcaagttac ccaactgtag aaggttgtta tattgaaggt        360
gaaatgcgtt caaccgatga tatgttggca gaagaaggaa caggttctcc agcggataat        420
gtagatttta tgacggtttg gggatataag ttaccagctg gttatatgat gagtttacaa        480
gaaggaggaa ttagagctta tgatgctggt accacttata ttgatggaga agtaatccaa        540
agagcaacag ataaccctac cgttctaaat tgtaccatta aaaatgcaag aacaggagtg        600
actttagcac atgctaaagg aacaaaacac gtagaaaatg ttaaggctat tgggtgtgag        660
caaggatatt caatt                                                        675

<210> SEQ ID NO 24
<211> LENGTH: 14
<212> TYPE: PRT
<213> ORGANISM: Bacteria

<400> SEQUENCE: 24

His Ser Gly Val Leu Ile Arg Gly Leu Arg Asn His Leu Lys
 1               5                  10

-continued

```
<210> SEQ ID NO 25
<211> LENGTH: 10
<212> TYPE: PRT
<213> ORGANISM: Bacteria

<400> SEQUENCE: 25

Leu Asn Ile Asn Thr Val Val Leu Thr Lys
 1               5                  10

<210> SEQ ID NO 26
<211> LENGTH: 21
<212> TYPE: DNA
<213> ORGANISM: Bacteria

<400> SEQUENCE: 26
gttcaatagt aacagcaaac c                                             21

<210> SEQ ID NO 27
<211> LENGTH: 28
<212> TYPE: DNA
<213> ORGANISM: Bacteria

<400> SEQUENCE: 27
ccggatccca aacaaccaca gtatattc                                      28

<210> SEQ ID NO 28
<211> LENGTH: 21
<212> TYPE: DNA
<213> ORGANISM: Bacteria

<400> SEQUENCE: 28
tccatcaatg gcatttgctg c                                             21

<210> SEQ ID NO 29
<211> LENGTH: 14
<212> TYPE: PRT
<213> ORGANISM: Bacteria

<400> SEQUENCE: 29

Met Ala Ser Met Thr Gly Gly Gln Gln Met Gly Arg Gly Ser
 1               5                  10

<210> SEQ ID NO 30
<211> LENGTH: 20
<212> TYPE: DNA
<213> ORGANISM: Bacteria

<400> SEQUENCE: 30
atgttaccac taataccatc                                               20
```